(12) United States Patent
Deng et al.

(10) Patent No.: US 12,338,480 B2
(45) Date of Patent: Jun. 24, 2025

(54) ACONITIC ACID EXPORTER (aexA) INCREASES ORGANIC ACID PRODUCTION IN ASPERGILLUS

(71) Applicant: Battelle Memorial Institute, Richland, WA (US)

(72) Inventors: Shuang Deng, Richland, WA (US); Jon K. Magnuson, Richland, WA (US); Joonhoon Kim, Berkeley, CA (US); Kyle R. Pomraning, Richland, WA (US); Ziyu Dai, Richland, WA (US); Beth A. Hofstad, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 18/493,590

(22) Filed: Oct. 24, 2023

(65) Prior Publication Data
US 2024/0076700 A1    Mar. 7, 2024

Related U.S. Application Data

(62) Division of application No. 17/347,109, filed on Jun. 14, 2021, now Pat. No. 11,873,523.
(Continued)

(51) Int. Cl.
*C12P 7/46*  (2006.01)
*C12N 1/14*  (2006.01)
*C12R 1/69*  (2006.01)

(52) U.S. Cl.
CPC ............... *C12P 7/46* (2013.01); *C12N 1/145* (2021.05); *C12R 2001/69* (2021.05)

(58) Field of Classification Search
CPC ........ C12P 7/46; C12N 1/145; C12R 2001/69
See application file for complete search history.

(56) References Cited

U.S. PATENT DOCUMENTS

| 4,123,459 A | 10/1978 | Gutierrez et al. |
| 4,740,464 A | 4/1988 | Holdom et al. |

(Continued)

FOREIGN PATENT DOCUMENTS

| CN | 110527637 A | 12/2019 |
| WO | WO 2018/213349 A1 | 11/2018 |

OTHER PUBLICATIONS

Quistgaard, Esben M., et al. "Understanding transport by the major facilitator superfamily (MFS): structures pave the way." Nature Reviews Molecular Cell Biology 17.2 (2016): 123-132. (Year: 2016).*

(Continued)

*Primary Examiner* — Louise W Humphrey
*Assistant Examiner* — Candice Lee Swift
(74) *Attorney, Agent, or Firm* — Klarquist Sparkman, LLP

(57) ABSTRACT

Recombinant *Aspergillus* genetically modified to increase expression of g8846, renamed herein as aconitic acid exporter (aexA), are provided, which in some examples are also genetically inactivated for an endogenous cis-aconitic acid decarboxylase (cadA) gene. Such recombinant *Aspergillus* produce more aconitic acid as compared to native *Aspergillus*. Also provided are methods of using such recombinant *Aspergillus* to increase production of aconitic acid and other organic acids, such as citric acid, itaconic acid, and 3-hydroxypropionic acid (3-HP).

16 Claims, 6 Drawing Sheets
(2 of 6 Drawing Sheet(s) Filed in Color)
Specification includes a Sequence Listing.

Related U.S. Application Data

(60) Provisional application No. 63/039,241, filed on Jun. 15, 2020.

(56) References Cited

U.S. PATENT DOCUMENTS

| | | |
|---|---|---|
| 10,947,548 B2 | 3/2021 | Deng et al. |
| 2008/0199926 A1 | 8/2008 | Burgard et al. |
| 2015/0267228 A1 | 9/2015 | Borodina et al. |
| 2021/0163966 A1 | 6/2021 | Deng et al. |
| 2021/0388399 A1 | 12/2021 | Deng et al. |

OTHER PUBLICATIONS

Bruce, W.F, in Organic Syntheses (Ed.: H. A. Blatt), John Wiley and Sons, Inc., New York, 1943, pp. 12-14.

Cao et al., "A novel hyperbranched polyester made from aconitic acid (B3) and di(ethylene glycol) (A2)," *Polym Int. 60*:630-634, 2011.

Clustal Omega; https://www.ebi.ac.uk/Tools/msa/clustalo/; accessed Jul. 18, 2023 (Year: 2022).

Deng et al., "Deletion analysis of the itaconic acid biosynthesis gene cluster components in *Aspergillus pseudoterreus* ATCC32359," *Appl Microbiol Biotechnol. 104*:3981-3992, 2020.

Deng et al., "Deletion Analysis of the Itaconic Acid Production Gene Cluster Components in *Aspergillus pseudoterreus* ATCC32359," Poster presented at 40th Symposium on Biotechnology for Fuels and Chemicals, Apr. 29-May 2, 2018, Clearwater, Florida.

GenBank Database Accession No. AB326105, Aug. 2008 (2 pages).

Kobayashi et al., "Bioproduction of trans-Aconitic Acid from Citric Acid by Whole-Cell Reaction of *Escherichia coli* Heterologously Expressing the Aconitate Isomerase Gene from *Pseudomonas* sp. WU-0701," *ChemistrySelect 1*:1467-1471, 2016.

Kumar and Raveendiran, "Synthesis, Characterisation, Biological and Molecular Docking Studies of Aconitic Acid Based Co-Polyester," *Asian J Research Chem. 11*:723-730, 2018.

Li et al., "A clone-based transcriptomics approach for the identification of genes relevant for itaconic acid production in Aspergillus," *Fungal Genetics and Biology 48*:602-611, 2011.

Nielsen, J., "Metabolic Engineering," *Appl Microbial Biotechnol. 55*:263-283, 2001.

Quistgaard et al., "Understanding Transport by the Major Facilitator Superfamily (MFS): Structures Pave the Way," *Nat Rev. 17*:123-132, 2016.

Rodrigues et al., "Exploring the Brazilian diversity of *Aspergillus* sp. strains for lovastatin and itaconic acid production," *Fungal Genet Biol. 138*:103367, 2020 (11 pages).

Samson et al., "New species in *Aspergillus* section *Terrei*," *Stud Mycol. 69*:39-55, 2011.

Samson et al., "Phylogeny, identification and nomenclature of the genus *Aspergillus*," *Stud Mycol. 78*:141-173, 2014.

Steiger et al., "Biochemistry of microbial Itaconlc acid production," *Frontiers Microbial. 4*:23, 2013 (5 pages).

Tao, L., "Engineering the Production of Itaconic Acid in *Escherichia coli*," Dissertation, Rice University, 2011 (75 pages).

UniProt Database Accession No. B3IUN8, Oct. 2017 (2 pages).

Van der Straat et al., "Expression of the Aspergillus terreus itaconic acid biosynthesis cluster in *Aspergillus niger*," Microb. Cell Fae. 13:11, 2014 (9 pages).

\* cited by examiner

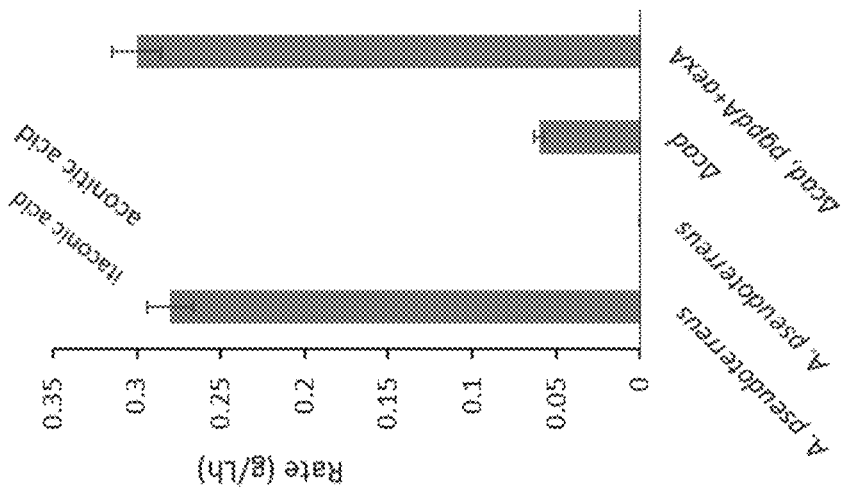
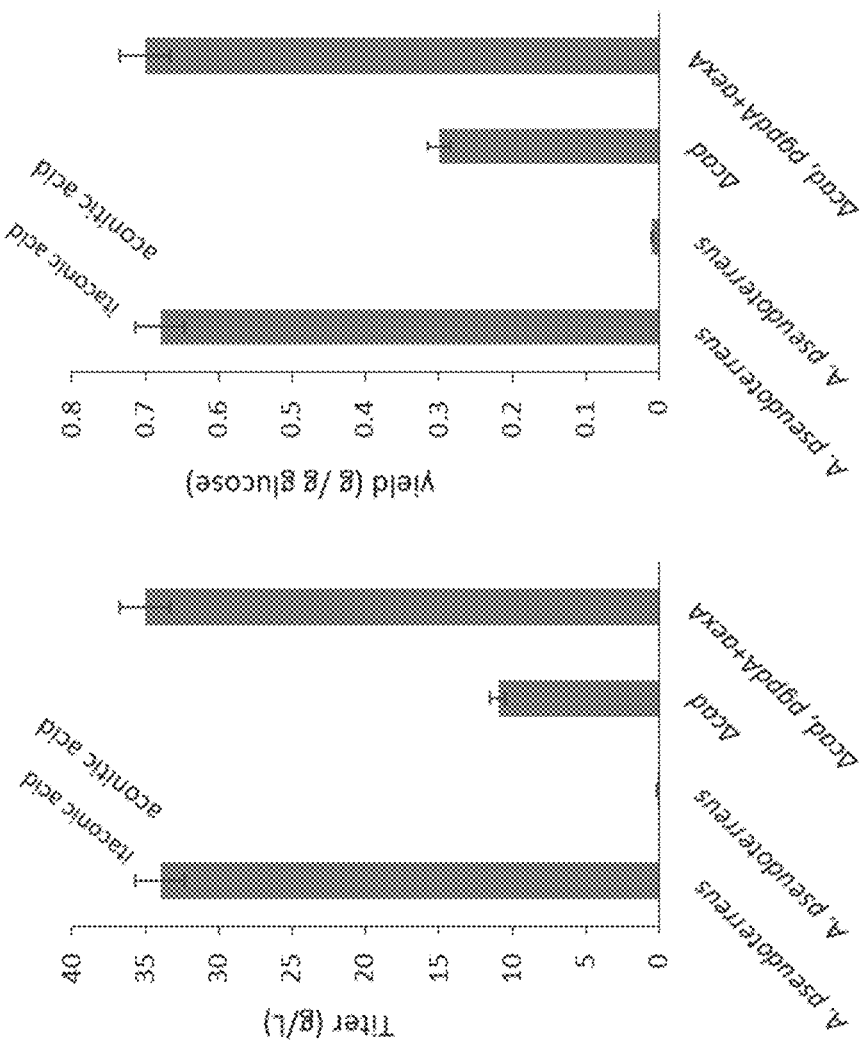
FIG. 4A  FIG. 4B  FIG. 4C

FIG. 5

ACONITIC ACID EXPORTER (aexA) INCREASES ORGANIC ACID PRODUCTION IN ASPERGILLUS

CROSS REFERENCE TO RELATED APPLICATIONS

This application is a divisional of U.S. application Ser. No. 17/347,109 filed Jun. 14, 2021, which claims priority to U.S. Provisional Application No. 63/039,241 filed Jun. 15, 2020, both of which are herein incorporated by reference in their entireties.

ACKNOWLEDGMENT OF GOVERNMENT SUPPORT

This disclosure was made with Government support under Contract DE-AC05-76RL0 1830 awarded by the U.S. Department of Energy. The Government has certain rights in the invention.

FIELD

Recombinant *Aspergillus* genetically modified to increase expression of aconitic acid exporter (aexA) are provided, which in some examples are also genetically inactivated for an endogenous cis-aconitic acid decarboxylase (cadA) gene. Also provided are methods of using such recombinant *Aspergillus* to increase production of aconitic acid and other organic acid products such as citric acid, itaconic acid, and 3-hydroxypropionic acid (3-HP).

INCORPORATION OF ELECTRONIC SEQUENCE LISTING

The Sequence Listing is submitted as an XML file in the form of the file named Sequence.xml, which was created on Oct. 24, 2023, and is 139,039 bytes, which is incorporated by reference herein.

BACKGROUND

Aconitic acid (AA) is one of the top 30 potential building block candidates (Werpy and Petersen 2004). It is a 6-carbon unsaturated tricarboxylic acid and there are two isomer, cis- and trans-. In nature, it can be extracted from plants such as sugar cane, beet root and sorghum. It is used as artificial flavor in the food industry. It can also be used as plasticizer to increase flexibility in making polymer. Trans-AA can be used to make polymers (Cao et al. 2011), especially the biomaterials in biomedical field (Kumar and Raveendiran 2018).

However, industrial processes proposed for aconitic acid synthesis give low yields, require energy intensive high temperatures, utilize harmful reagents and generate hazardous byproducts (Gutierrez; Eddie N. 1978), which is not a sustainable approach. Recently, the first bio-based trans-AA was produced by metabolic engineering aconitase isomerase from *Pseudomonas* sp. WU-0701 into *E. coli* (Kobayashi 2016). However, the substrate for the recombinant *E. coli* to produce trans-AA is citric acid, which has to be first generated from other fermentation processes.

Previously, a fungal platform was produced for the production of AA from lingocellulosic biomass by deleting cis-aconitate decarboxylase (cadA) gene in *Aspergillus pseudoterreus* (Deng et al. 2020). *Aspergillus pseudoterreus* naturally produces large amount of itaconic acid (see FIGS. 4A-4C). cis aconitic acid is converted to itaconic acid with the presence of cadA. By deleting the cadA gene, the new strain no longer produced itaconic acid, instead producing AA at about 10 g/L at day 7 (see FIG. 4A). However, compared with wild type, AA yield is only ⅕ of itaconic acid (see FIGS. 4A-4C).

SUMMARY

Using comparative proteomics analysis of an *Aspergillus pseudoterreus* cadA wild type strain vs an *Aspergillus pseudoterreus* cadA mutant strain, a specific aconitic acid exporter (aexA, g8846 gene in *Aspergillus pseudoterreus*) was identified. It is shown herein that overexpression of aexA in *Aspergillus* results in high production of aconitic acid.

Based on this discovery, provided herein are isolated recombinant *Aspergillus* fungi having at least one exogenous nucleic acid molecule that encodes aconitic acid exporter (aexA) operably linked to an exogenous promoter (such as a strong promoter), thereby overexpressing the aexA in the *Aspergillus*. The sequence encoding aexA (as well as the aexA protein produced) may be native to the particular strain or species of *Aspergillus*, but it is operably linked to a non-native promoter, making the resulting construct (which may be a vector) non-native to the recombinant *Aspergillus*. The recombinant *Aspergillus* can further include other genetic modifications, such as a genetically inactivated endogenous cis-aconitic acid decarboxylase (cadA) gene. In some examples, the recombinant *Aspergillus* furthers includes one or more additional exogenous nucleic acid molecules that encode proteins that allow the *Aspergillus* to produce other products. For example, the recombinant *Aspergillus* can include exogenous nucleic acid molecules encoding aspartate 1-decarboxylase (panD), a β-alanine-pyruvate aminotransferase (BAPAT), and 3-hydroxypropionate dehydrogenase (3-HPDH), thereby permitting the *Aspergillus* to produce 3-HP.

Also provided are isolated nucleic acid molecules encoding an aexA protein operably linked to a heterologous promoter. Such isolated nucleic acid molecules can be part of a vector, such as a plasmid.

Compositions that include one or more disclosed recombinant *Aspergillus* are provided, as are compositions that include one or more disclosed isolated nucleic acid molecules encoding an aexA protein operably linked to a heterologous promoter. In some examples the compositions include other materials, such as a growth media or a pharmaceutically acceptable carrier, such as water or saline.

Kits are also provided that include one or more disclosed recombinant *Aspergillus* and a growth media for culturing or growing the *Aspergillus*. In some examples the *Aspergillus* is in a container, such as a glass or plastic vial, which may also include growth media. Kits are also provided that include disclosed isolated nucleic acid molecules encoding an aexA protein operably linked to a heterologous promoter. In some examples, a kit also includes one or more reagents to allow transformation of *Aspergillus*, such as protoplast isolation buffer, osmotic wash buffer, polyethylene glycol, filtration material (such as miracloth), antibiotic (e.g., hygromicin), or combinations thereof.

Also provided are methods of making AA. Such methods can include culturing a recombinant *Aspergillus* fungus provided herein that overexpresses aexA (and in some examples also has a genetically inactivated endogenous cadA gene) under conditions that permit the fungus to make AA, thereby producing AA. Similar methods can be used to produce citric acid and itaconic acid. Also provided are methods of making 3-hydroxypropionic acid (3-HP). Such methods can include culturing a recombinant *Aspergillus* fungus provided herein that overexpresses aexA (and in some examples also has a genetically inactivated endogenous cadA gene), along with panD, BAPAT, and 3-HPDH, under conditions that permit the fungus to produce 3-HP, thereby making 3-HP.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4C are bar graphs showing the effect of aexA (g8846) overexpression using SEQ ID NO: 21 on titer, yield and rate of aconitic acid in *A. pseudoterreus*. The first bar shows itaconic acid production in wild type *A. pseudoterreus*. The three other bars show aconitic acid production in *A. pseudoterreus* with wild type cadA (cadA+), with endogenous cadA deleted (ΔcadA), and with endogenous cadA deleted and aexA overexpressed from a gpdA promoter (ΔcadA+pgpdA+aexA).

Figure 5:
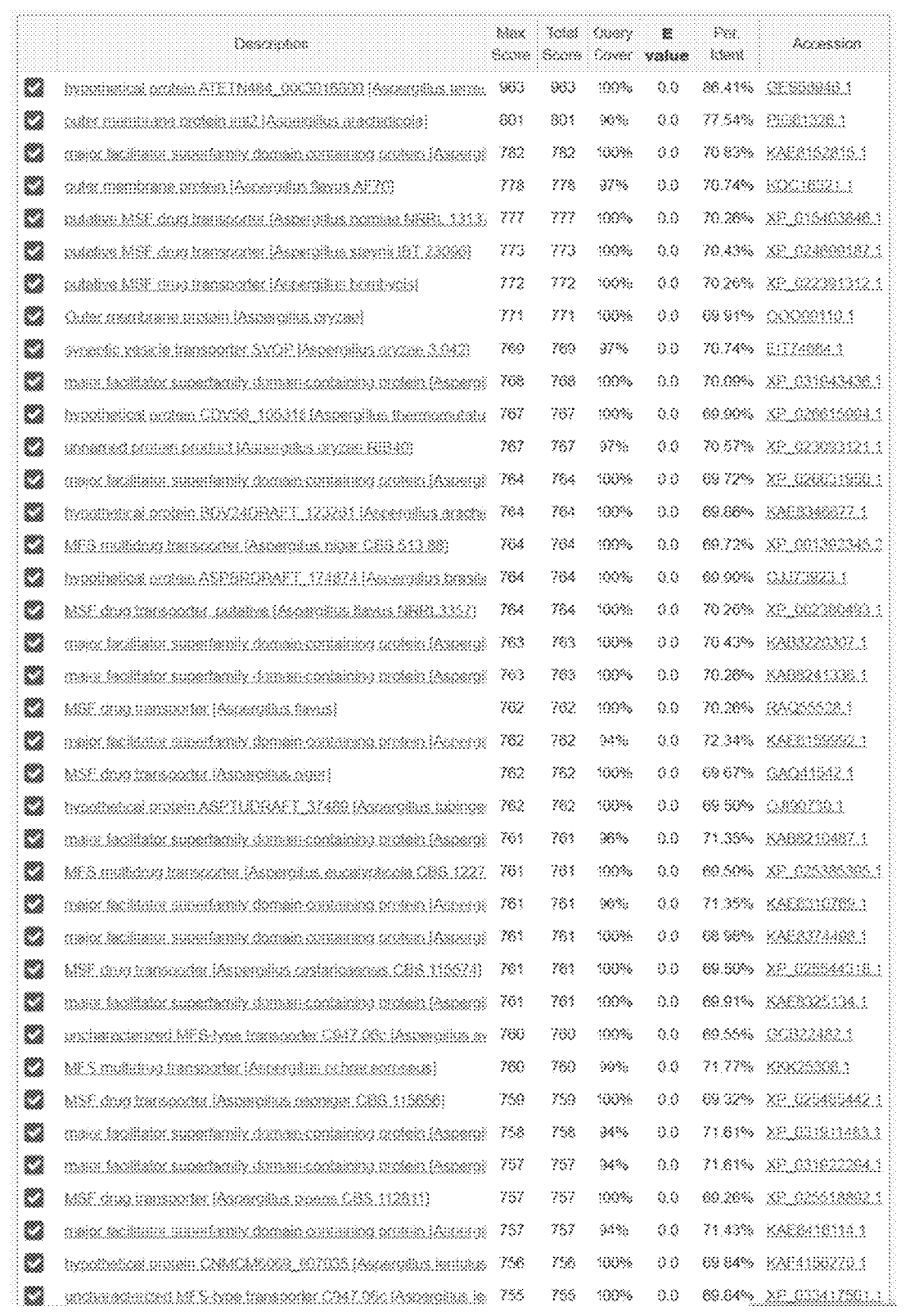

FIG. 5 shows the results of the blastp program to identify homologs of SEQ ID NO: 2. Thus, the GenBank accession nos. provided disclosed aexA sequences that can be overexpressed in *Aspergillus*, for example in combination endogenous cad deleted (Δcad).

SEQUENCE LISTING

Figure 1:
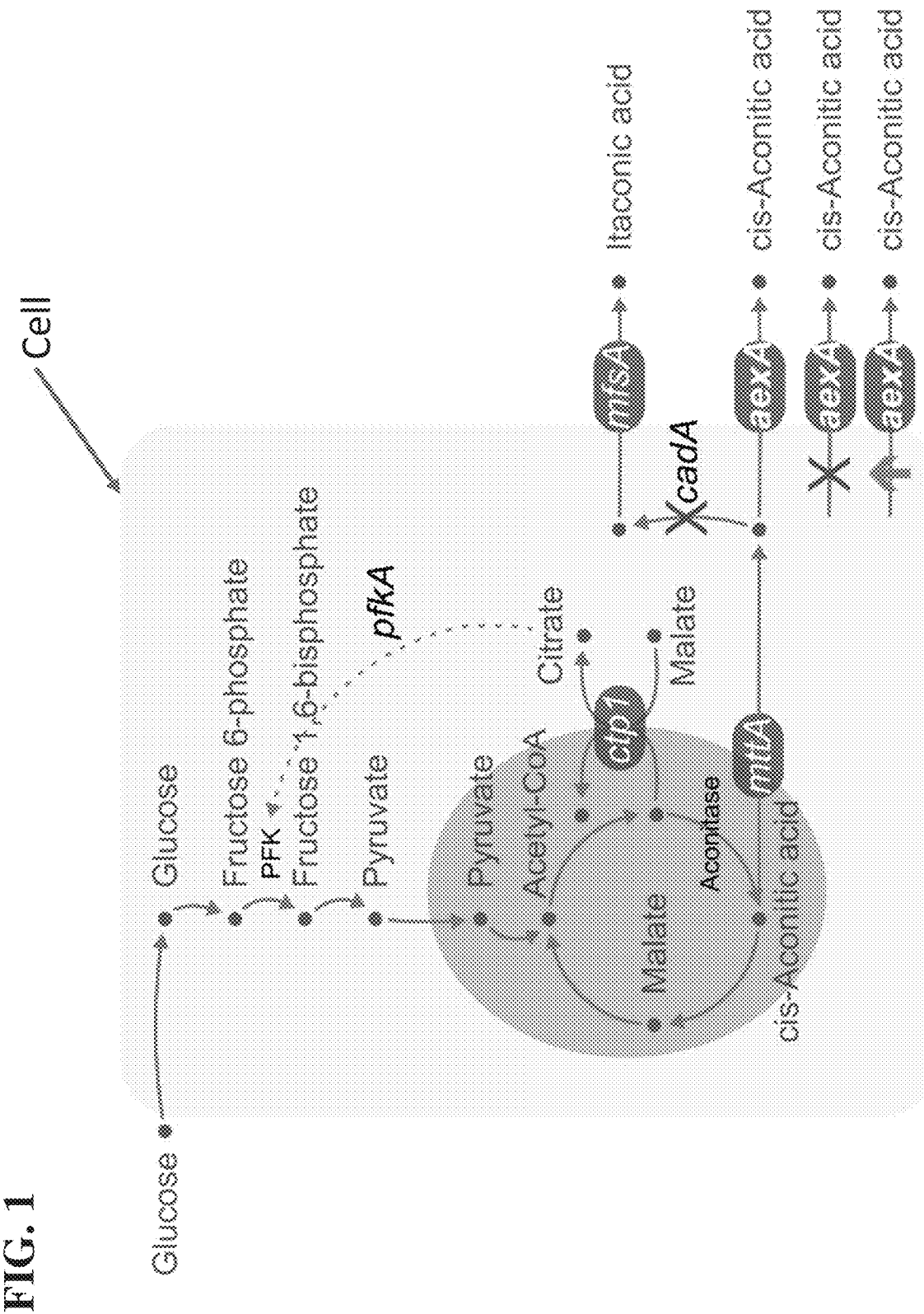
FIG. 1 is a schematic drawing of the aconitic acid biosynthetic and transport pathway. Aconitic acid and itaconic acid share the same biosynthesis pathway, but use different transporters to export outside the cell. Itaconic acid is secreted through mfsA transporter. Deletion of cadA results in accumulation of aconitic acid, which is secreted from the cell via a specific aexA transporter.

The nucleic acid sequences listed in the accompanying sequence listing are shown using standard abbreviations for nucleotide bases and amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1-2 are exemplary aexA coding and protein sequences, respectively, from *A. pseudoterreus*.

SEQ ID NO: 3 is an exemplary aexA protein sequence from *A. terreus* (GenBank® Accession No. GES58946.1). Corresponding coding sequence GenBank Accession No. BKZMO2000003.1: 443944.445205

SEQ ID NO: 4 is an exemplary aexA protein sequence from *A. arachidicola* (GenBank Accession No. PIG81326.1). Corresponding coding sequence GenBank Accession No. join (NEXV01000567.1: 39009.39417, NEXV01000567.1:39519.39862, NEXV01000567.1:39922.40253, NEXV01000567.1: 40314.40405, NEXV01000567.1:40461.40482, NEXV01000567.1:40546.40889, NEXV01000567.1: 41917.42713, NEXV01000567.1:42769.43772, NEXV01000567.1:43830.43896, NEXV01000567.1: 43997.44073, NEXV01000567.1:44145.44162, NEXV01000567.1:44241.44331)

SEQ ID NO: 5 is an exemplary g8846 (aexA) protein sequence from *A. avenaceus* (GenBank Accession No. KAE8152815.1). Corresponding coding sequence GenBank Accession No. join (ML742047.1: 79398.80261, ML742047.1:80313.80644, ML742047.1:80695.80786, ML742047.1: 80840.80861, ML742047.1:80918.81275

SEQ ID NOS: 6 and 7 are exemplary cadA nucleic acid and protein sequences, respectively, from *A. terreus* (GenBank Accession Nos. AB326105.1 and BAG49047.1).

SEQ ID NOS: 8 and 9 are exemplary cadA nucleic acid and protein sequences, respectively, from *A. vadensis* CBS 113365 (GenBank® Accession Nos. XM_025706777.1 and XP_025563141.1).

SEQ ID NO: 10 is an *A. pseudoterreus* 5'-cadA nucleic acid sequence.

SEQ ID NO: 11 is an *A. pseudoterreus* 3'-cadA gene.

SEQ ID NOS: 12 and 13 are exemplary aspartate 1-decarboxylase (panD) nucleic acid and protein sequences, respectively, from *Tribolium castaneum* (GenBank® Accession Nos. NM_001102585.1 and NP_001096055.1). Coding sequence nt 41-1663.

SEQ ID NO: 14 is panD cDNA of *Tribolium castaneum* with codon optimization for *A. pseudoterreus*.

SEQ ID NOS: 15 and 16 are exemplary β-alanine-pyruvate aminotransferase (BAPAT) nucleic acid and protein sequences, respectively, from *Bacillus cereus* AH1272 (GenBank® Accession Nos. ACMS01000158.1 (complement (10606.11961)) and EEL86940.1).

SEQ ID NO: 17 is BAPAT codon optimized synthetic cDNA for *A. pseudoterreus* from *Bacillus cereus*.

SEQ ID NOS: 18 and 19 are exemplary 3-hydroxypropionate dehydrogenase (3-HPDH) nucleic acid and protein sequences (GenBank® Accession No. WP_000636571), respectively.

SEQ ID NO: 20 is the 3-HPDH codon optimized synthetic cDNA for *A. pseudoterreus* from *E. coli*.

SEQ ID NO: 21 is a vector that can be used to overexpresses aexA. nt 1-2951 pBSK vector backbone; nt 2952-3932 gpdA promoter from *Aspergillus nidulans*; nt 3933-5678 aconitic acid exporter aexA coding sequence; nt 5679-6465 TrpC terminator from *A. nidulans*, and nt 6466-8478 pyrithiamine selection marker (ptrA) selection marker from *A. oryzae*.

SEQ ID NOS: 22-29 are primers that can be used to delete an endogenous cadA gene in *A. pseudoterreus*.

SEQ ID NO: 30 is an *A. niger* gpdA promoter nucleic acid sequence.

SEQ ID NO: 31 is a bidirectional terminator from *A. niger* elf3/multifunctional chaperone.

SEQ ID NO: 32 is an *A. niger* eno1 promoter.

SEQ ID NO: 33 is an *A. nidulans* gpdA promoter.

SEQ ID NOS: 34-39 are primers used to delete endogenous mfsA from *A. pseudoterreus*.

SEQ ID NOS: 40-45 are primers used to delete endogenous g2022 from *A. pseudoterreus*.

SEQ ID NOS: 46-51 are primers used to delete endogenous g2739 from *A. pseudoterreus*.

SEQ ID NOS: 52-57 are primers used to delete endogenous g2945 from *A. pseudoterreus*.

SEQ ID NOS: 58-64 are primers used to delete endogenous g8846 (aexA) from *A. pseudoterreus*.

SEQ ID NOS: 65-69 are primers used to delete endogenous g9513 from *A. pseudoterreus*.

SEQ ID NOS: 70-75 are primers used to delete endogenous g9885 from *A. pseudoterreus*.

SEQ ID NOS: 76-81 are primers used to delete endogenous g9935 from *A. pseudoterreus*.

SEQ ID NOS: 82-89 are primers used to overexpress g8846 (aexA) from gpdA promoter in *A. pseudoterreus*.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, references and Genbank® Accession numbers (the sequence available on Jun. 15, 2020) mentioned herein are incorporated by reference in their entireties. The materials, methods, and examples are illustrative only and not intended to be limiting.

In order to facilitate review of the various embodiments of the disclosure, the following explanations of specific terms are provided:

3-hydroxypropionate dehydrogenase (3-HPDH): EC 1.1.1.59 An enzyme that catalyzes the chemical reaction: 3-hydroxypropanoate+NAD$^+$⇌3-oxopropanoate+NADH+H$^+$. The term 3-HPDH includes any 3-HPDH gene (such as a bacterial or fungal panD sequence), cDNA, mRNA, or protein, which is a 3-HPDH that can covert 3-hydroxypropanoate and NAD$^+$ into 3-oxopropanoate, NADH, and H$^+$ and vice versa. Expression or increased expression of 3-HPDH, for example in an *Aspergillus* also expressing BAPAT and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

3-HPDH sequences are publicly available. For example, SEQ ID NO: 18 discloses a 3-HPDH coding sequence and GenBank® Accession No: WP_000636571 discloses a 3-HPDH protein sequence (SEQ ID NO: 19); GenBank® Accession Nos. FR729477.2 (nt 1005136.1005885) and CBY27203.1 disclose exemplary *Yersinia enterocolitica* subsp. *palearctica* Y11 3-HPDH nucleic acid and protein sequences, respectively; and GenBank® Accession Nos: CP004083.1 (complement(1399227.1399973) and AJQ99264.1 disclose exemplary Enterobacteriaceae bacterium bta3-1 3-HPDH nucleic acid and protein sequences, respectively. However, one skilled in the art will appreciate that in some examples, a 3-HPDH sequence can include variant sequences (such as allelic variants and homologs) that retain 3-HPDH activity and when expressed in an *Aspergillus* also expressing BAPAT and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

Aconitic acid (AA): An organic acid with two isomers, cis- and trans-aconitic acid. The recombinant *Aspergillus* fungi provided herein that overexpress aexA (e.g., from an exogenous nucleic acid molecule), and in some examples also having a genetically inactivated cadA gene (ΔcadA), can be used to produce cis- and/or trans-aconitic acid.

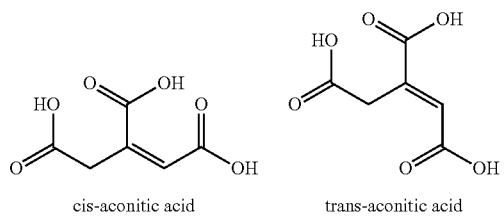 [SMILES: O=C(O)/C=C(/CC(=O)O)C(=O)O ; O=C(O)/C=C(\CC(=O)O)C(=O)O]

cis-aconitic acid     trans-aconitic acid

Aconitic acid exporter (aexA, g8846): The aexA gene encodes a cell membrane protein responsible for the transport of aconitic acid from a cell, such as from *Aspergillus*. The term aexA (or aexA or g8846) includes any aexA gene (such as an endogenous fungal aexA sequence), cDNA, mRNA, or protein, that is a aexA that can export AA from a cell, and when genetically overexpressed results in an *Aspergillus* that secretes more AA than a strain without a (1) genetically overexpressed aexA gene and (2) endogenous cadA expression (ΔcadA) (see FIGS. 4A-4C, such as at least 2-fold, at least 3-fold, at least 4-fold, or at least 5-fold more than a strain without (1) a genetically overexpressed aexA gene and (2) endogenous cadA expression (ΔcadA) under the same growing conditions, for example at day 7 of production).

aexA sequences are publicly available for many species of *Aspergillus*. For example, using the aexA sequences shown in SEQ ID NOS: 1 and 2 for *A. pseudoterreus*, additional aexA sequences can be identified from publicly available databases (for example using blastp, see FIG. 5 for exemplary GenBank® Accession Nos: identified). GenBank® Accession Nos: GES58946.1 (SEQ ID NO: 3) and BKZM02000003.1:443944.445205 disclose *Aspergillus terreus* aexA protein and nucleic acid sequences, respectively; GenBank® Accession Nos: NEXV01000567.1 and PIG81326.1 (SEQ ID NO: 4) disclose *Aspergillus arachidicola* aexA nucleic acid and protein sequences, respectively; and GenBank® Accession Nos: KAE8152815.1 (SEQ ID NO: 5) and ML742047.1 disclose *Aspergillus avenaceus* aexA protein and nucleic acid sequences, respectively. However, one skilled in the art will appreciate that in some examples, an aexA sequence can include variant sequences (such as allelic variants and homologs) that retain aexA activity but when overexpressed in *Aspergillus* results in a fungus that produces more aconitic acid than an *Aspergillus* fungus (1) without genetically overexpressed aexA gene and (2) without endogenous cadA expression (ΔcadA) (see FIGS. 4A-4C, such as at least 2-fold, at least 3-fold, at least 4-fold, or at least 5-fold more than a strain (1) without a genetically overexpressed aexA gene and (2) without endogenous cadA expression (ΔcadA) under the same growing conditions, for example at day 7 of production.

Aspartate 1-decarboxylase (panD): EC 4.1.1.11. An enzyme that catalyzes the chemical reaction: L-aspartate ⇌ beta-alanine+$CO_2$. The term panD includes any panD gene (such as a bacterial or fungal panD sequence), cDNA, mRNA, or protein, that is a panD that can covert L-aspartate into beta-alanine+$CO_2$ and vice versa. Expression or increased expression of panD, for example in an *Aspergillus* also expressing BAPAT and 3-HPDH and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

panD sequences are publicly available. For example, GenBank® Accession Nos: NM_001102585.1 and NP_001096055.1 disclose *Tribolium castaneum* panD nucleic acid and protein sequences, respectively (SEQ ID NOS: 12 and 13); GenBank® Accession Nos. CP002745.1 (complement(4249351.4249824)) and AEK63458.1 disclose exemplary *Collimonas fungivorans* Ter331 panD nucleic acid and protein sequences, respectively; and GenBank® Accession Nos: CP029034.1 (nt 1201611.1201994) and AWE15802.1 disclose exemplary *Bacillus velezensis* panD nucleic acid and protein sequences, respectively. However, one skilled in the art will appreciate that in some examples, a panD sequence can include variant sequences (such as allelic variants and homologs) that retain panD activity and when expressed in an *Aspergillus* also expressing BAPAT and 3-HPDH and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

β-alanine-pyruvate aminotransferase (BAPAT): EC 2.6.1.18. An enzyme that can catalyze the reaction L-alanine+3-oxopropanoate⇌beta-alanine+pyruvate. The term BAPAT includes any BAPAT gene (such as a bacterial or fungal panD sequence), cDNA, mRNA, or protein, that is a BAPAT that can convert beta-alanine and pyuvate to L-alanine and 3-oxopropanoate [or malonic semialdehyde], and vice versa. Expression or increased expression of BAPAT, for example in an *Aspergillus* also expressing 3-HPDH and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

BAPAT sequences are publicly available. For example, GenBank® Accession Nos: ACMS01000158.1 (complement(10606.11961)) and EEL86940.1 disclose *Bacillus cereus* AH1272 BAPAT nucleic acid and protein sequences, respectively (SEQ ID NOS: 15 and 16); GenBank® Accession Nos. DF820429.1 (complement (241627.242967)) and GAK28710.1 disclose exemplary *Serratia liquefaciens* FK01 BAPAT nucleic acid and protein sequences, respectively; and GenBank Accession Nos: LGUJ01000001.1 complement (92812.94140) and KOY12524.1 disclose exemplary *Bradyrhizobium diazoefficiens* BAPAT nucleic acid and protein sequences, respectively. However, one skilled in the art will appreciate that in some examples, a BAPAT sequence can include variant sequences (such as allelic variants and homologs) that retain BAPAT activity and when expressed in an *Aspergillus* also expressing 3-HPDH and panD and overexpressing aexA (e.g., from an exogenous nucleic acid molecule), and in some examples also having a genetically inactivated cadA gene (ΔcadA), results in a fungus that has an ability to produce more 3-HP than the parent strain (such as at least 20%, at least 30%, at least 40%, at least 50%, at least 60% at least 70%, at least 100%, at least 200%, at least 300%, or at least 400% more than a parent strain under the same growing conditions, such as about 20-50%, about 30-50%, or about 40-50% more).

cadA (cis-aconitic acid decarboxylase): The cadA gene encodes an enzyme (EC 4.1.1.6) that catalyzes the chemical reaction cis-aconitate⇌itaconate+$CO_2$. The term cadA (or cadA) includes any cadA gene (such as an endogenous fungal cadA sequence), cDNA, mRNA, or protein, that is a cadA that can catalyze the decarboxylation of cis-aconitate to itaconate and $CO_2$ and vice versa, and when genetically inactivated results in a fungus that produces more aconitic acid than the parent strain without a genetically inactivated cadA gene (see FIGS. 4A-4C, such as at least 20%, at least 30%, at least 50%, at least 60%, at least 75%, at least 100%, at least 200%, at least 500%, or 1000% more than a parent strain under the same growing conditions, for example at day 5 of production). In some examples, a parental strain containing a functional native cadA sequence does not produce detectable aconitic acid (see FIGS. 4A-4C). In some examples, genetic inactivation of cadA results in an *Aspergillus* that produces more trans-aconitic acid than cis-aconitic acid at day 10 of production, (such as at least 2-fold, at least 3-fold, at least 4-fold, or at least 5-fold more at day 10 of production).

cadA sequences are publicly available for many species of *Aspergillus*. For example, GenBank® Accession Nos: AB326105.1 and BAG49047.1 disclose *Aspergillus terreus* cadA nucleic acid and protein sequences, respectively (SEQ ID NOS: 6 and 7); GenBank® Accession Nos: XM_025706777.1 and XP_025563141.1 disclose *Aspergillus vadensis* CBS 113365 cadA nucleic acid and protein sequences, respectively (SEQ ID NOS: 8 and 9); and GenBank® Accession Nos: XM_025663103.1 and XP_025520527.1 disclose *Aspergillus piperis* CBS 112811 cadA nucleic acid and protein sequences, respectively. However, one skilled in the art will appreciate that in some examples, a cadA sequence can include variant sequences (such as allelic variants and homologs) that retain cadA activity but when genetically inactivated in *Aspergillus* results in a fungus that has an ability to produce more aconitic acid than the parent strain without a genetically inactivated cadA gene (such as at least 20%, at least 30%, at least 50%, at least 60%, at least 75%, at least 100%, at least 200%, at least 500%, or 1000% more than a parent strain under the same growing conditions, for example at day 5 of production).

Detectable: Capable of having an existence or presence ascertained. For example, production of aconitic acid, citric acid, or 3-HP is detectable if the signal generated is strong enough to be measurable.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. A nucleic acid that is naturally-occurring also can be exogenous to a particular cell. For example, an entire chromosome isolated from cell X is an exogenous nucleic acid with respect to cell Y once that chromosome is introduced into cell Y, even if X and Y are the same cell type.

In some examples, a nucleic acid molecule used to overexpress aexA is exogenous to the *Aspergillus* into which it is introduced, as even if the aexA sequence is endogenous, it is operably linked to a non-endogenous promoter, making the entire nucleic acid molecule exogenous as it does not naturally occur in the *Aspergillus* fungi.

In some examples, the panD, BAPAT, and 3-HPDH nucleic acid or protein expressed in *Aspergillus* does not naturally occur in that strain or species of *Aspergillus* and is therefore exogenous to that fungi. For example, panD, BAPAT, and 3-HPDH nucleic acid molecule introduced into an *Aspergillus terreus* or *Aspergillus pseudoterreus* fungi can be from another organism, such as a bacterial panD, BAPAT, and 3-HPDH sequence.

Genetic enhancement or up-regulation: When used in reference to the expression of a nucleic acid molecule, such as a gene, refers to any process which results in an increase in production of a gene product (such as an aexA protein). A gene product can be RNA (such as mRNA, rRNA, tRNA, and structural RNA) or protein. Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene up-regulation can include inhibition of repression as well as expression above an existing level. Examples of processes that increase translation include those that increase translational initiation, those that increase translational elongation and those that increase mRNA stability. In one example, additional copies of genes are introduced into a cell in order to increase expression of that gene in the resulting transgenic cell.

Gene up-regulation includes any detectable increase in the production of a gene product. In certain examples, production of a gene product increases by at least 1.5-fold, at least 2-fold, at least 3-fold, at least 4-fold, or at least 5-fold), such as aexA, aspartate decarboxylase (panD), β-alanine-pyruvate aminotransferase (BAPAT), and/or 3-HPDH. In one example, expression of an aexA gene in *Aspergillus* (e.g., *A. terreus*) results in an *Aspergillus* strain having an increased amount of aexA protein, relative to the parent strain, which can permit the recombinant fungus to export greater amounts of AA. Genetic enhancement is also referred to herein as "enhancing or increasing expression."

Genetic inactivation or down-regulation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of an endogenous cadA gene in *Aspergillus* (e.g., *A. pseudoterreus*) results in the *Aspergillus* having a non-functional or non-detectable cadA protein, which results in the recombinant fungus producing more aconitic acid than the parent strain with a native/non-mutated/non-deleted cadA sequence (see FIGS. 4A-4C, Δcad vs cad+). Genetic inactivation is also referred to herein as "functional deletion".

Isolated: To be significantly separated from other agents. An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as a *Aspergillus* over-expressing aexA, and in some examples also ΔcadA) has been substantially separated or purified away from microorganisms of different types, strains, or species. Microorganisms can be isolated by a variety of techniques, including serial dilution and culturing and resistance to certain chemicals, such as antibiotics. In some examples, an isolated *Aspergillus* strain overexpres sing aexA (and in some examples is also ΔcadA) is at least 90% (for example, at least 95%, as at least 98%, at least 99%, or at least 99.99%) pure.

Mutation: A change in a nucleic acid sequence (such as a gene sequence) or amino acid sequence, for example as compared to a nucleic acid or amino acid sequence present in a wild-type or native organism. In particular examples, a mutation is introduced into an endogenous cadA gene in *Aspergillus*, thereby rendering it non-functional. Mutations can be introduced, for example using molecular biology methods (e.g., thereby generating a recombinant or transformed cell or microorganism). In particular examples, a mutation includes one or more nucleotide substitutions, deletions, insertions, or combinations thereof. In particular examples, the presence of one or more mutations in a gene can significantly inactivate and reduce expression of that gene (such as an endogenous cadA gene).

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In some examples, a promoter is bi-directional. Native and non-native promoters (i.e., endogenous and exogenous) can be used to drive expression of a gene, such as aexA, panD, BAPAT, and 3-HPDH. Exemplary promoters that can be used include but are not limited to: eno1 promoter from *A. niger*, and dth1 from *A. nidulans* or *A. niger*.

Additional examples of promoters that can be used include, but are not limited to the SV40 promoter, the CMV enhancer-promoter, and the CMV enhancer/β-actin promoter. Both constitutive and inducible promoters can be used in the fungi and methods provided herein (see e.g., Bitter et al., *Methods in Enzymology* 153: 516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid molecule or protein is one that has a sequence that is not naturally occurring (such as an exogenous promoter operably linked to a native aexA coding sequence) or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 3d ed., vol. 1-3, Cold Spring Harbor Laboratory Press, Cold Spring Harbor, NY, 2001. The term recombinant includes nucleic acid molecules that have been altered solely by addition, substitution, or deletion of a portion of the nucleic acid molecule. A recombinant or transformed organism or cell, such as a recombinant *Aspergillus*, is one that includes at least one exogenous nucleic acid molecule, such as one used to overexpress aexA, one used to genetically inactivate an endogenous cadA gene, or one used to express a non-native protein such as exogenous panD, BAPAT, and 3-HPDH nucleic acid coding sequences.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, Gene, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq-i c:\seq1.txt-j c:\seq2.txt-p blastn-o c:\output.txt-q-1-r 2.

To compare two amino acid sequences, the options of B12seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided. Thus, a variant aexA, cadA, panD, BAPAT, or 3-HPDH protein or nucleic acid molecule that can be used with the organisms and methods of the present disclosure can have at least 80%, at least 85%, at least 90%, at least 91%, at least 92%, at least 93%, at least 94%, at least 95%, at least 96%, at least 97%, at least 98% or at least 99% sequence identity to the SEQ ID NOs: and GenB ank® Accession Nos. provided herein.

Transformed: A cell, such as a fungal cell, into which a nucleic acid molecule has been introduced, for example by molecular biology methods. As used herein, the term transformation encompasses all techniques by which a nucleic acid molecule might be introduced into such a cell, including, but not limited to chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses. In one example, a protoplast transformation method is used, such as the on described in Example 1.

Vector: A nucleic acid molecule as introduced into a host cell, thereby producing a transformed or recombinant host cell. A vector may include nucleic acid sequences that permit it to replicate in the host cell, such as an origin of replication. A vector may also include an aexA, panD, BAPAT, and/or 3-HPDH coding sequence, and/or a sequence used to genetically inactivate cadA, for example in combination with a promoter, and/or selectable marker genes, and other genetic elements. A vector can transduce, transform or infect a cell, thereby causing the cell to express nucleic acids and/or proteins. A vector optionally includes materials to aid in achieving entry of the nucleic acid into the cell, such as a viral particle, liposome, protein coating or the like. In one example, a vector is a plasmid, such as a plasmid exogenous to the cell or organism into which it is introduced.

Overview

Currently, trans-aconitc acid is produced by chemical synthesis and requires high temperature and harmful solvents. Generation of trans-aconitic acid has been achieved by metabolic engineering aconitase isomerase from *Pseudomonas* sp. WU-0701 into *E. coli*. However, the substrate for the recombinant *E. coli* to produce trans-aconitic acid is citric acid, which is generated first from fermentation. In contrast, the disclosed recombinant fungi can produce trans-aconitic acid directly from renewable biomass substrates.

*A. pseudoterreus* naturally produces a large amount of itaconic acid (see FIGS. 4A-4C, cad+, Deng et al. 2020, Li et al. 2011). As shown in FIG. 1, glucose is utilized by *A. pseudoterreus* to form pyruvate and is subsequently converted to citric acid in the TCA cycle in the mitochondria. Citric acid is dehydrated to cis-AA, which then is transported from the mitochondria into the cytosol via transporter. In the cytosol, cis-AA is decarboxylated into itaconic acid and $CO_2$ by CAD. Genetic deletion of cadA results in cis-AA that cannot be converted into itaconic acid. As a result, AA accumulates in the cell, and then is exported outside the cell. However, AA production is much lower than itaconic acid in the parent strain (compare first and third bars in FIGS. 4A-4C).

Figure 3:
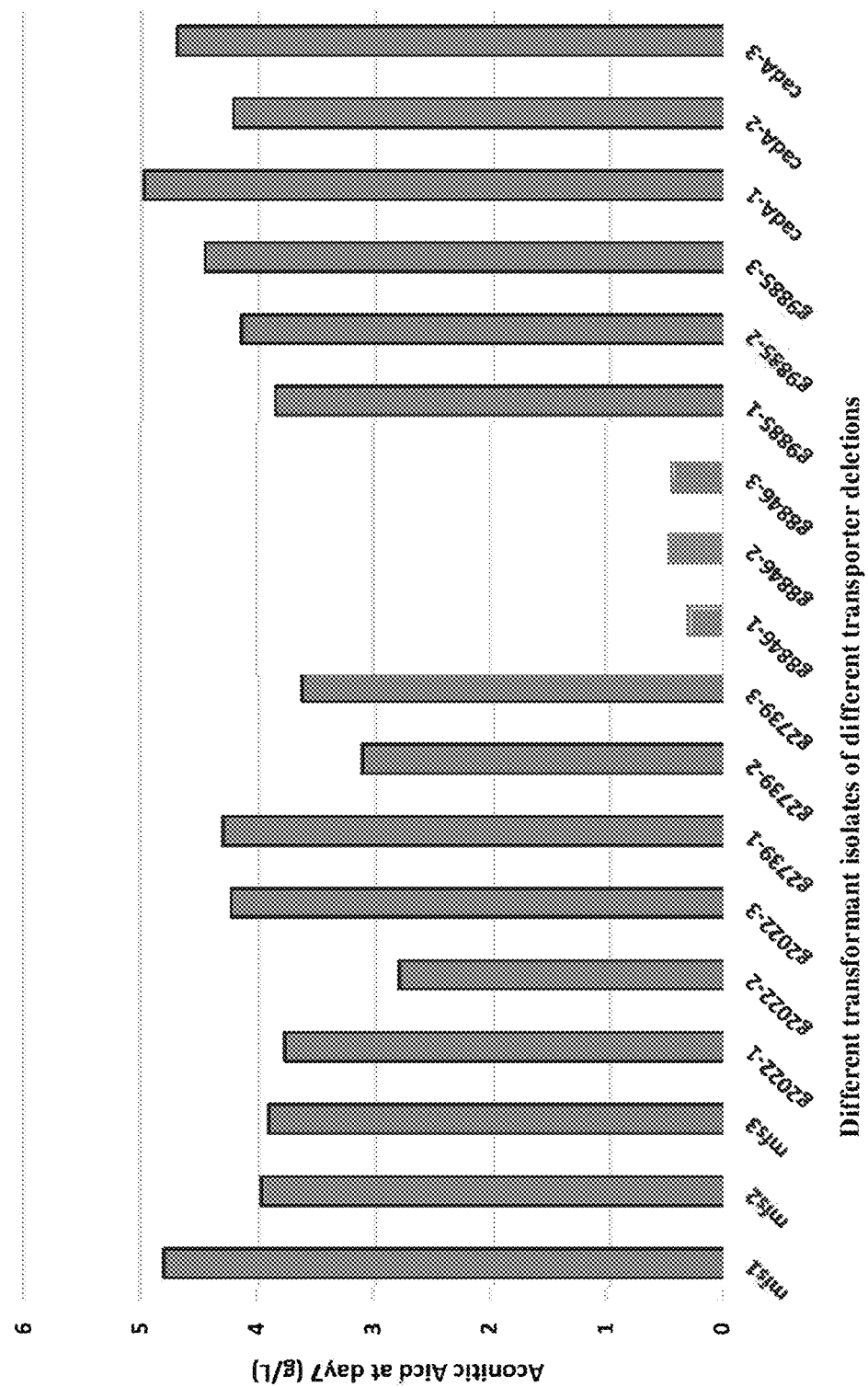
FIG. 3 is a bar graph showing the production of AA from different transporter gene deletions (g2022, g2739, g8846, and g9885). mfs is an itaconic acid transporter. Results for *A. pseudoterreus* with a cadA deletion are also shown (cadA-1, cadA-2 and cadA-3).

It was investigated whether the specific AA exporter on the cell membrane was a limiting factor. The inventors performed comparative proteomics analysis on membrane proteins in both wild type *A. pseudoterreus* and cadA deletion (ΔcadA) stains to identify aconitic acid transporter candidates. Deletion assay results demonstrated that an aexA deletion dramatically decreased aconitic acid production (FIG. 3, g8846 clones). In contrast, overexpression of aexA resulted in a significant increase in secreted aconitic acid. The yield of AA is as high as itaconic acid in parent (native aexA, cad+) itaconic acid producing strain (FIGS. 4A-4C). The exporter aexA for aconitic acid was saturated at low level in a ΔcadA strain (10 g/L). However, when overexpressed, export of AA increased to 50 g/L. Thus, the recombinant *Aspergillus* and methods provided herein can be used for industry-scale production of AA since it shares same industry process and infrastructure as itaconic acid.

Provided herein are isolated recombinant *Aspergillus* fungi that include one or more exogenous nucleic acid molecules encoding aconitic acid exporter (aexA or g8846) operably linked to an exogenous promoter, thereby overexpressing the aexA in the fungus. Introduction of the one or more exogenous nucleic acid molecules encoding aexA operably linked to an exogenous promoter results in integration of at least the exogenous promoter and the operably linked aexA coding sequence into the genome of the recombinant *Aspergillus*. Such recombinant *Aspergillus* fungi are referred to herein as aexA+. The aexA exporter protein is expressed at the cell membrane. The coding sequence of aexA may be endogenous to the particular *Aspergillus*, but is operably linked to an exogenous/heterologous promoter, that is one in nature that does not drive expression of aexA in the particular strain or species of *Aspergillus*. Exemplary promoters include gpdA (for example from *A. niger*, see SEQ ID NO: 30 or *A. nidulans*, see SEQ ID NO: 33), and eno1 (for example from *A. niger*, see SEQ ID NO: 32). The one or more exogenous nucleic acid molecules can be part of a vector, such as a plasmid. In some examples, the nucleic acid molecule encoding aexA overexpressed in *Aspergillus* has at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 1 (or any sequence referred to in FIG. 5). In some examples, the nucleic acid molecule encoding aexA overexpressed in *Aspergillus* encodes a protein having at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 2, 3, 4, or 5 (or any sequence referred to in FIG. 5). In some examples, the *Aspergillus* is *Aspergillus pseudoterreus*, *Aspergillus terreus*, *Aspergillus niger*, or *Aspergillus oryzae*. In some examples, overexpression of aexA is determined by measuring AA production by the recombinant *Aspergillus*.

In some examples, such a recombinant *Aspergillus* fungi includes other genetic alterations, such as a genetically inactivated endogenous cis-aconitic acid decarboxylase (cadA) gene. Such recombinant *Aspergillus* fungi are referred to herein as aexA+/ΔcadA. In some examples, the endogenous cadA gene is genetically inactivated by mutation (such as a complete or partial deletion of the cadA gene) or by insertional mutation (such as by insertion of another nucleic acid molecule into the cadA gene, such as an antibiotic resistance marker). In one example, the endogenous cadA gene in the strain or species of *Aspergillus* is genetically inactivated by complete deletion. Exemplary cadA gene sequences that can be genetically inactivated are provided herein. In some examples, the cadA gene, prior to its genetic inactivation, encodes a protein having at least 80%, at least 85%, at least 90%, at least 95%, at least 96%, at least 97%, at least 98%, at least 99%, or 100% sequence identity to SEQ ID NO: 7 or 9. In some examples, the cadA gene, prior to its genetic inactivation, has a coding sequence having at least 80%, at least 85%, at least 90%, at least 95%, at least 96%, at least 97%, at least 98%, at least 99%, or 100% sequence identity to SEQ ID NO: 6, 8, 10 or 11. In one example, decreased or elimination of cadA activity by a particular recombinant *Aspergillus* strain is determined by measuring decarboxylation of cis-aconitic acid into itaconic acid and carbon dioxide (Bentley & Thiessen, 1955, Science, 122(3164), 330).

The disclosed recombinant *Aspergillus* fungi can express other genes/proteins (endogenous or exogenous) needed to permit the fungi to produce other organic acids. For example, the disclosed aexA+ and aexA+/ΔcadA fungi can further include an endogenous or exogenous nucleic acid molecule encoding aspartate 1-decarboxylase (panD), an endogenous or exogenous nucleic acid molecule encoding β-alanine-pyruvate aminotransferase (BAPAT), and an endogenous or exogenous nucleic acid molecule encoding 3-hydroxypropionate dehydrogenase (3-HPDH). panD, BAPAT, and 3-HPDH coding sequences can be part of a one or more nucleic acid molecules, such as a vector. In addition, expression of the panD, BAPAT, and 3-HPDH coding sequences can be driven by one or more promoters, such as a bi-directional promoter. In some examples, the promoter is native to the gene it is expressing. In some examples, the promoter is from *A. niger*. In some examples, the panD, BAPAT, and/or 3-HPDH coding sequences are inserted into the cadA gene, genetically inactivating cadA. In some examples, the nucleic acid molecule encoding panD has at least 80%, at least 90%, at least 95%, at least 98%, at least 99%, or 100% sequence identity to SEQ ID NO: 12 or 14, and/or encodes a panD protein comprising at least 80%, at least 90%, at least 95%, at least 98%, at least 99%, or 100% sequence identity to SEQ ID NO: 13. In some examples, the nucleic acid molecule encoding BAPAT has at least 80%, at least 90%, at least 95%, at least 98%, at least 99%, or 100% sequence identity to SEQ ID NO: 15 or 17, and/or encodes a BAPAT protein having at least 80%, at least 90%, at least 95%, at least 98%, at least 99%, or 100% sequence identity to SEQ ID NO: 16. In some examples, the nucleic acid molecule encoding 3-HPDH has at least 80%, at least 90%, at least 95%, at least 98%, at least 99%, or 100% sequence identity to SEQ ID NO: 18 or 20, and/or encodes a 3-HPDH protein having at least 80%, at least 90%, at least 95%, at least 98%, at least 99%, or 100% sequence identity to SEQ ID NO: 19.

Also provided are isolated nucleic acid molecules that include a heterologous promoter operably linked to an aexA coding sequence, wherein the promoter is not endogenous to the aexA coding sequence. The one or more exogenous nucleic acid molecules can be part of a vector, such as a plasmid. In some examples, the aexA coding sequence s has at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 1 (or any sequence referred to in FIG. 5). In some examples, the aexA coding sequence encodes a protein having at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 2, 3, 4, or 5 (or any sequence referred to in FIG. 5). Exemplary promoters include gpdA (for example from *A. niger*, see SEQ ID NO: 30 or *A. nidulans*, see SEQ ID NO: 33), and eno1 (for example from *A. niger*, see SEQ ID NO: 32). In some examples, the promoter has at least 80%, at least 90%, at least 95%, at least 98%, at least 99%, or 100% sequence identity to SEQ ID NO: 30, 32, or 33, wherein the promoter does not have a native or endogenous sequence to the aexA coding sequence. In some examples, the nucleic acid molecule further includes a terminator sequence following the aexA coding sequence, such as TrpC (e.g., from *A. nidulans*, see nt 5679-6465 of SEQ ID NO: 21) or elf3/multifunctional chaperone (e.g., from *A. niger*, see SEQ ID NO: 31). In some examples, the terminal sequence has at least 80%, at least 90%, at least 95%, at least 98%, at least 99%, or 100% sequence identity to nt 5679-6465 of SEQ ID NO: 21 or to SEQ ID NO: 31. In some examples, the nucleic acid molecule has at least 80%, at least 90%, at least 95%, at least 98%, at least 99%, or 100% sequence identity to nt 2952-6678 or nt 2952-6465 of SEQ ID NO: 21. In some examples, such a nucleic acid molecule is part of a vector, such as a plasmid. In some examples, such a plasmid has at least 80%, at least 90%, at least 95%, at least 98%, at least 99%, or 100% sequence identity to SEQ ID NO: 21. Also provided are compositions and kits that include such nucleic acid molecules and plasmids. Such a composition can include a pharmaceutically acceptable carrier, such as water or saline. Such a kit can further include reagents for transforming *Aspergillus*, such as protoplast isolation buffer, osmotic wash buffer, polyethylene glycol, filtration material (such as miracloth), antibiotic (e.g., hygromicin), or combinations thereof, growth media (such as complete media, minimal media, Riscaldati medium, modified Riscaldati medium with 20× trace elements)), or combinations thereof. Such reagents can be in separate containers of the kit.

The disclosure also provides compositions that include the disclosed aexA+ and aexA+/ΔcadA recombinant *Aspergillus* that express or overexpress other genes (such as panD, BAPAT, and 3-HPDH). Such a composition can include a solid or liquid culture or growth media, such as complete media, minimal media, or Riscaldati medium (such as modified Riscaldati medium with 20× trace elements).

The disclosure also provides kits that include the disclosed aexA+ and aexA+/ΔcadA fungi, and such *Aspergillus* that express or overexpress other genes (such as panD, BAPAT, and 3-HPDH). Such kits can include a solid or liquid culture or growth media, such as complete media, minimal media, or Riscaldati medium (such as modified Riscaldati medium with 20× trace elements). In some examples, a kit also includes one or more reagents to allow transformation of *Aspergillus*, such as protoplast isolation buffer, osmotic wash buffer, polyethylene glycol, filtration material (such as miracloth), antibiotic (e.g., hygromicin), or combinations thereof.

Also provided are methods of using the disclosed aexA+ and aexA+/ΔcadA fungi to make aconitic acid. Such a method can include culturing the recombinant *Aspergillus* fungi under conditions that permit the fungus to make aconitic acid, such as growth in Riscaldati medium, thereby making aconitic acid. In some examples, the aconitic acid generated is cis-aconitic acid, trans-aconitic acid, or both. In some examples, the disclosed aexA+ and aexA+/ΔcadA fungi produce at least 2-fold, at least 3-fold, at least 4-fold, at least 5-fold, at least 10-fold, at least 20-fold, at least 30-fold, at least 40-fold, or at least 50-fold more AA than an amount of AA produced by an *Aspergillus* fungus of the same species and strain with native aexA expression (and in some examples also native cadA expression). In some examples, the fungi are cultured at room temperature (e.g., 20-35° C., such as about 30° C.) at normal atmospheric pressure (e.g., 1 atm). In some examples, the method includes purifying or isolating the aconitic acid, for example from the culture media or from the cultured fungus. In some examples, the aconitic acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing. Thus, in some examples, the disclosed aexA+ and aexA+/ΔcadA fungi work as biocatalyst that converts biomass into aconitic acid through bioproduction method at room temperature (such as about 20-35° C.) and ordinary pressure (such as about 1 atm). Current processes of aconitic acid production include chemical synthesis that require high temperatures and harmful reagents.

Also provided are methods of using the disclosed aexA+ fungi to make citric acid. Such a method can include culturing a recombinant *Aspergillus niger* fungi that overexpresses aexA under conditions that permit the fungus to make citric acid, such as growth in citric acid production medium, thereby making citric acid. In some examples, the disclosed recombinant *Aspergillus niger* that overexpress aexA produce at least 5%, at least 10%, at least 12%, or at least 14% more (such as 5-20%, 5-15%, or 5-14% more) citric acid than an amount of citric acid produced by an *Aspergillus niger* of the same strain with native aexA expression. In some examples, the fungi are cultured at room temperature (e.g., 20-35° C., such as about 30° C.) at normal atmospheric pressure (e.g., 1 atm). In some examples, the method includes purifying or isolating the citric acid, for example from the culture media or from the cultured fungus. In some examples, the citric acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Also provided are methods of using the disclosed recombinant *Aspergillus* that overexpress aexA to make itaconic acid. Such a method can include culturing a recombinant *Aspergillus pseudoterrus* fungi that overexpresses aexA under conditions that permit the fungus to make itaconic acid, such as growth in Riscaldati medium, thereby making itaconic acid. In some examples, the fungi are cultured at room temperature (e.g., 20-35° C., such as about 30° C.) at normal atmospheric pressure (e.g., 1 atm). In some examples, the method includes purifying or isolating the itaconic acid, for example from the culture media or from the cultured fungus. In some examples, the itaconic acid is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Also provided are methods of using the disclosed aexA+ and aexA+/ΔcadA fungi, and which also express or overexpress panD, BAPAT, and 3-HPDH, to make 3-HP. Such a method can include culturing the disclosed recombinant *Aspergillus* fungi expressing panD, BAPAT, and 3-HPDH under conditions that permit the fungus to make 3-HP, such as growth in Riscaldati medium (such as modified Riscaldati medium with 20× trace elements), thereby making 3-HP. In some examples, the disclosed recombinant *Aspergillus* (such as *A. niger*) that overexpress aexA produce at least 10%, at least 20%, at least 30%, at least 40%, or at least 50% more (such as 10-75%, 10-60%, 10-50%, or 25-50% more, such as about 50% more) 3-HP than an amount of 3-HP produced by an *Aspergillus* (such as *A. niger*) of the same strain with native aexA expression. In some examples, the fungi are cultured at room temperature (e.g., 20-35° C., such as about 30° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Recombinant Fungi

The present disclosure provides isolated recombinant *Aspergillus* fungi expressing one or more exogenous nucleic acid molecules that overexpress aexA from a heterologous (i.e., non-native) promoter. Such recombinant *Aspergillus* fungi are referred to herein as aexA+ fungi or aexA+ *Aspergillus*. In some examples, the recombinant *Aspergillus* fungi overexpressing aexA also have their cadA gene genetically inactivated (e.g., functionally deleted, ΔcadA). Such recombinant *Aspergillus* fungi are referred to herein as aexA+/ΔcadA fungi or aexA+/ΔcadA *Aspergillus*. It is shown herein that *Aspergillus* strains overexpressing aexA have increased aconitic acid (AA) production as compared to *Aspergillus* having native levels of aexA expression.

Any variety or strain of *Aspergillus* can be used. In particular examples, the *Aspergillus* fungus is *A. terreus* or *A. pseudoterreus*, as well as particular strains thereof (for example *A. terreus* NRRL 1960, *A. pseudoterreus* ATCC 32359). In some examples, the *Aspergillus* is *Aspergillus niger* or *Aspergillus oryzae*.

Any method for increasing expression of aexA can be used, as long as the expression of the aexA gene is significantly increased, or the function of the aexA protein is significantly increased. In particular examples, expression of an aexA gene is genetically enhanced by introducing a transgene that includes aexA coding or gene sequence operably linked to a heterologous promoter sequence. In some embodiments, increased expression refers to an increase of at least 20%, at least 30%, at least 40%, at least 50%, at least 60%, at least 70%, at least 80%, at least 90%, at least 100%, at least 200%, at least 300% at least 400%, or at least 500%. The term "increased" as used herein with respect to a cell and aexA gene or protein activity refers to a higher level of activity than that measured in a comparable cell of the same species without the transgene. For example, a particular *Aspergillus* expressing a recombinant aexA from a heterologous promoter sequence has increased aexA activity/expression if a comparable *Aspergillus* not having the transgene has lower aexA activity.

aexA sequences are disclosed herein and others are publicly available, for example from GenBank or EMBL. In some examples, the aexA gene overexpressed encodes a protein having at least 80%, at least 90%, at least 95%, at least 96%, at least 97%, at least 98%, at least 99%, or 100% sequence identity to SEQ ID NO: 2, 3, 4 or 5. In some examples, the endogenous aexA gene overexpressed has at least 80%, at least 90%, at least 95%, at least 96%, at least 97%, at least 98%, at least 99% or 100% sequence identity to SEQ ID NO: 1.

Similarly, any method of genetic inactivation of cadA can be used, as long as the expression of the endogenous cadA gene is significantly reduced or eliminated, or the function of the cadA protein is significantly reduced or eliminated. In particular examples, the cadA gene is genetically inactivated by complete or partial deletion mutation or by insertional mutation. In some examples genetic inactivation need not be 100%. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular *Aspergillus* lacking cadA activity has reduced cadA activity if a comparable *Aspergillus* not having a cadA genetic inactivation has detectable cadA activity.

cadA sequences are disclosed herein and others are publicly available, for example from GenBank or EMBL. In some examples, the cadA gene functionally deleted encoded a protein having at least 80%, at least 90%, at least 95%, at least 97%, at least 98%, at least 99%, or 100% sequence identity to SEQ ID NO: 7 or 9 prior to its genetic inactivation. In some examples, the endogenous cadA gene functionally deleted has at least 80%, at least 90%, at least 95%, at least 96%, at least 97%, at least 98%, at least 99% or 100% sequence identity to SEQ ID NO: 6, 8, 10, or 11 prior to its genetic inactivation.

Increased expression of aexA results in many phenotypes in a recombinant *Aspergillus*, such as *A. terreus* or *A. pseudoterreus*. For example, aexA+ or aexA+/ΔcadA mutants can produce at least 2-fold, at least 3-fold, at least 3.5 fold, at least 5-fold, at least 8-fold, at least 10-fold, at least 20-fold, at least 30-fold, at least 40-fold, or at least 50-fold more total aconitic acid than a wild-type *Aspergillus* (for example at day 3, 4, 5, 6, 7, 8, 9 or 10 of production). In some examples, such increases are relative to *Aspergillus terreus* strain ATCC 32359 grown under the same conditions as the aexA+ or aexA+/ΔcadA mutant. In some examples, an increased total aconitic acid production by aexA+ or aexA+/ΔcadA fungi occurs at least 3 days (such as at least 4, 5, 6, 7, 8, 9, or 10 days) after inoculation in Riscaldati medium (such as at least 0.5 g/L aconitic acid or at least 1 g/L aconitic acid), as compared to no detectable aconitic acid produced by *Aspergillus terreus* strain ATCC 32359 at the same time point.

Additional genes can also be upregulated or inactivated in the disclosed aexA+ and aexA+/ΔcadA fungi, wherein the additional genes may or may not provide additional enhancement of aconitic acid production to the fungus.

In some examples, the disclosed aexA+ and aexA+/ΔcadA fungi include one or more additional exogenous nucleic acid molecules, for example to permit production of other organic acids by the recombinant fungi. In one example, the disclosed aexA+ and aexA+/ΔcadA fungi includes an endogenous or exogenous nucleic acid molecule encoding aspartate decarboxylase (panD), an endogenous or exogenous nucleic acid molecule encoding β-alanine-pyruvate aminotransferase (BAPAT), and an endogenous or exogenous nucleic acid molecule encoding 3-hydroxypropironate dehydrogenase (3-HPDH). Exogenous nucleic acid molecules can be part of one or more exogenous nucleic acid molecules (such as 1, 2 or 3 exogenous nucleic acid molecules). In some examples, exogenous nucleic acid molecules can be part of a vector, such as a plasmid or viral vector. In some examples, expression of the exogenous nucleic acid molecules is driven by one or more promoters, such as a constitutive or inducible promoter, or a bi-directional promoter. In some examples, the promoter used to drive expression of panD, BAPAT, and 3-HPDH is a native promoter (e.g., native to the panD, BAPAT, and 3-HPDH gene expressed). In other examples, the promoter used to drive expression of panD, BAPAT, and 3-HPDH is a non-native promoter (e.g., exogenous to the panD, BAPAT, and 3-HPDH gene expressed). In some examples, such a ΔcadA fungi expressing panD, BAPAT, and 3-HPDH are used to produce 3-HP.

A. Methods of Increasing aexA, panD, BAPAT, and/or 3-HPDH Expression

Methods of increasing native aexA expression in *Aspergillus* are provided. Similar methods can be used to increase expression of other genes, such as panD, BAPAT, and/or 3-HPDH nucleic acid sequences in an *Aspergillus* that does not have such sequences, or where increased expression is desired. In some examples, expression of aexA, panD, BAPAT, and/or 3-HPDH is increased by introducing aexA, panD, BAPAT, and/or 3-HPDH nucleic acid coding sequences (such may be codon optimized) into *Aspergillus*, such as *A. pseudoterreus*, *A. terreus*, or *A. niger*.

In some examples, expression of these genes is upregulated by introducing additional copies of aexA, panD, BAPAT, and/or 3-HPDH nucleic acid coding sequences (such may be codon optimized) into *Aspergillus* fungi. As used herein, "up-regulated" gene means that expression of the gene or gene product (e.g., protein) has been up-regulated, for example by introduction of additional copies of the appropriate gene or coding sequence into the fungus (or other molecular biology methods), such that the introduced nucleic acid sequence is expressed, resulting in increased expression or biological activity of the encoded gene product. In some embodiments, introduction of one or more transgenes including aexA, panD, BAPAT, and/or 3-HPDH coding sequences into *Aspergillus* increases expression of aexA, panD, BAPAT, and/or 3-HPDH by at least 20%, at least 40%, at least 50%, at least 100%, at least 150%, at least 200%, at least 300%, or at least 500%, for example relative to the parental *Aspergillus* strain without the introduced aexA, panD, BAPAT, and/or 3-HPDH coding sequences. The term "increased" or "up-regulated" as used herein with respect to a cell and a particular gene or protein activity refers to a higher level of activity than that measured in a comparable cell of the same species or strain. For example, a particular *Aspergillus* having increased or up-regulated aexA, panD, BAPAT, and/or 3-HPDH activity has increased panD, BAPAT, and/or 3-HPDH activity if a comparable *Aspergillus* having native aexA, panD, BAPAT, and/or 3-HPDH activity has less detectable aexA, panD, BAPAT, and/or 3-HPDH activity (for example as measured by gene or protein expression).

In one example, a strain of *Aspergillus* is transformed with a vector which has the effect of up-regulating a aexA, panD, BAPAT, and/or 3-HPDH gene (such as a native or non-native aexA, panD, BAPAT, and/or 3-HPDH gene). This can be done by introducing one or more aexA, panD, BAPAT, and/or 3-HPDH coding sequences (such as a gene sequence), whose expression is controlled by elements such as promoters and the like which control gene expression, by introducing a nucleic acid sequence which itself (or its encoded protein) can increase aexA, panD, BAPAT, and/or 3-HPDH protein activity in the fungus, or by introducing another molecule (such as a protein or antibody) increases aexA, panD, BAPAT, and/or 3-HPDH protein activity in the fungus. For example, a aexA, panD, BAPAT, and/or 3-HPDH gene can be up-regulated by introduction of a vector that includes one or more aexA, panD, BAPAT, and/or 3-HPDH coding sequences (such as 1, 2, 3, 4, 5, 6, 7, 8, 9 or 10 aexA, panD, BAPAT, and/or 3-HPDH sequences or copies of such sequences) into the desired fungus. In some examples, such aexA, panD, BAPAT, and/or 3-HPDH sequences are from different fungal species, can be multiple copies from a single species, or combinations thereof, such as aexA, panD, BAPAT, and/or 3-HPDH sequences from at least 2, 3, 4, 5, 6, 7, 8, 9, or 10 different fungal species. In some examples, the aexA, panD, BAPAT, and/or 3-HPDH sequence(s) introduced into the fungus is optimized for codon usage. Thus, the disclosure in some examples provides transformed fungi that include at least one exogenous nucleic acid molecule which includes a aexA, panD, BAPAT, and/or 3-HPDH gene or coding sequence (such as a nucleic acid sequence encoding SEQ ID NO: 2, 54, 56, or 58, respectively), for example in combination with ΔcadA. In one example, such transformed cells produce more AA, citric acid, or 3HP, for example relative to a comparable fungus with native aexA expression.

In one example, the cre-lox system is used for site specific recombination of DNA (for example see Steiger et al., *Appl. Environ. Microbiol.* 77(1):114, 2011). Using recombination techniques, a targeted gene of interest (e.g., cadA) can be deleted in the *Aspergillus* genome and replaced with one or more copies of an aexA, panD, BAPAT, and/or 3-HPDH sequence (for example in *A. terreus*, replacing one or both *A. terreus* cadA sequences with aexA, panD, BAPAT, and/or 3-HPDH sequences from *A. nidulans* or *A. flavus*) flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a fungus containing the desired insertion mutation and one copy of the lox sequence.

In one example, a transgene is generated and expressed in the desired fungal cell, such as a native or ΔcadA fungal cell, to increase aexA, panD, BAPAT, and 3-HPDH expression. For example, one or more transgenes can include an aexA, panD, BAPAT, and 3-HPDH genomic or cDNA sequence (such as one having at least 80%, at least 85%, at least 90%, at least 95%, at least 96%, at least 97%, at least 98%, at least 99%, or 100% sequence identity to any panD, BAPAT, and 3-HPDH sequence provided herein), for example operably linked to one or more promoters, such as gpdA and eno1. In one example, the promoter has at least 80%, at least 85%, at least 90%, at least 95%, at least 96%, at least 97%, at least 98%, at least 99%, or 100% sequence identity to SEQ ID NO: 32 and/or 33. In some examples, the transgene further includes a trpC transcriptional terminator sequence of *A. nidulans*, for example downstream of the panD, BAPAT, and/or 3-HPDH sequence. As an alternative to trpC, other transcriptional terminators can be used, such as promoters which include a transcriptional terminators (e.g., ArsA7, Arsa-37, polyubiquitin (ubi4)). In one example, the trpC transcriptional terminator has at least 80%, at least 85%, at least 90%, at least 95%, at least 96%, at least 97%, at least 98%, at least 99%, or 100% sequence identity to nt 5679-6465 of SEQ ID NO: 21. In one example, the trpC transcriptional terminator comprises or consists of nt 5679-6465 of SEQ ID NO: 21. In some examples, the transgene further includes a selection marker, such as a ptrA sequence, for example downstream of the trpC transcriptional terminator sequence. As an alternative to ptrA, the bleomycin gene or bar gene can be used. In one example, the ptrA sequence has at least 80%, at least 85%, at least 90%, at least 95%, at least 96%, at least 97%, at least 98%, or at least 99% sequence identity to nt 6466-8478 of SEQ ID NO: 21. In one example, the ptrA sequence comprises or consists of nt 6466-8478 of SEQ ID NO: 21.

In one example, the transgene used to increase expression of aexA in *Aspergillus* includes a sequence having at least 80%, at least 85%, at least 90%, at least 95%, at least 96%, at least 97%, at least 98%, at least 99%, or 100% sequence identity to SEQ ID NO: 1, SEQ ID NO: 21, nt 3933-5678 of SEQ ID NO: 21; nt 2952-5678 of SEQ ID NO: 21, nt 2952-6465 of SEQ ID NO: 21, nt 2952-8478 of SEQ ID NO: 21, nt 3933-6465 of SEQ ID NO: 21, or nt 3933-8478 of SEQ ID NO: 21. In one example, the transgene used to increase expression of aexA includes a sequence having at least 80%, at least 85%, at least 90%, at least 95%, at least 97%, at least 98%, at least 99%, or 100% sequence identity to SEQ ID NO: 30, 31, 32, and/or 33.

In one example, the vector used to increase expression of aexA in *Aspergillus* includes a sequence having at least 80%, at least 85%, at least 90%, at least 95%, at least 96%, at least 97%, at least 98%, at least 99%, or 100% sequence identity to SEQ ID NO: 1, SEQ ID NO: 21, nt 3933-5678 of SEQ ID NO: 21; nt 2952-5678 of SEQ ID NO: 21, nt 2952-6465 of SEQ ID NO: 21, nt 2952-8478 of SEQ ID NO: 21, nt 3933-6465 of SEQ ID NO: 21, or nt 3933-8478 of SEQ ID NO: 21. In one example, the vector used to increase expression of aexA includes a sequence having at least 80%, at least 85%, at least 90%, at least 95%, at least 97%, at least 98%, at least 99%, or 100% sequence identity to SEQ ID NO: 30, 31, 32, and/or 33.

In one example, the transgene used to express panD includes a sequence having at least 80%, at least 85%, at least 90%, at least 95%, at least 97%, at least 98%, at least 99%, or 100% sequence identity to SEQ ID NO: 12, 14, 30, 31, 32, and/or 33. In one example, the transgene comprises or consists of the sequence shown in SEQ ID NO: 12, 14, 30, 31, 32, and/or 33.

In one example, the transgene used to express BAPAT includes a sequence having at least 80%, at least 85%, at least 90%, at least 95%, at least 97%, at least 98%, at least 99%, or 100% sequence identity to SEQ ID NO: 15, 17, 30, 31, 32, and/or 33. In one example, the transgene comprises or consists of the sequence shown in SEQ ID NO: 15, 17, 30, 31, 32, and/or 33.

In one example, the transgene used to express 3-HPDH includes a sequence having at least 80%, at least 85%, at least 90%, at least 95%, at least 97%, at least 98%, at least 99%, or 100% sequence identity to SEQ ID NO: 18, 20, 30, 31, 32, and/or 33. In one example, the transgene comprises or consists of the sequence shown in SEQ ID NO: 18, 20, 30, 31, 32, and/or 33.

B. aexA Sequences aexA protein and nucleic acid sequences are publicly available and specific examples are provided herein. In addition, aexA sequences can be identified using molecular biology methods and using publicly available databases.

An exemplary aexA nucleic acid sequence is shown in SEQ ID NO: 1. However, the disclosure also encompasses variants of SEQ ID NO: 1 which encode a functional aexA protein. One skilled in the art will understand variants of the aexA nucleic acid sequences provided herein can be overexpressed. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Such variant aexA nucleic acid molecules can share at least 60%, at least 70%, at least 80%, at least 85%, at least 90%, at least 95%, at least 96%, at least 97%, at least 98%, or at least 99% sequence identity to any aexA nucleic acid sequence, such as SEQ ID NO: 1.

Examples of aexA protein sequences are shown in SEQ ID NOS: 2, 3, 4 and 5. However, the disclosure also encompasses variants SEQ ID NOS: 2, 3, 4 and 5 which retain aexA activity. One skilled in the art will understand that variants of these aexA sequences can be overexpressed. Variant sequences can be identified, for example by aligning known aexA sequences (e.g., see FIG. 5). Variant sequences may contain a single insertion, a single deletion, a single substitution, multiple insertions, multiple deletions, multiple substitutions, or any combination thereof (e.g., single deletion together with multiple insertions). Such aexA proteins share at least 60%, at least 65%, at least 69%, at least 70%, at least 71%, at least 75%, at least 80%, at least 85%, at least 90%, at least 95%, at least 96%, at least 97%, at least 98%, or at least 99% sequence identity to a aexA protein sequence, such as SEQ ID NO: 2, 3, 4 and 5.

In some examples, an aexA sequence that is to be overexpressed encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, an aexA protein sequence (such as SEQ ID NO: 2, 3, 4, or 5) includes one or more amino acid substitutions, such as conservative substitutions (for example at 1, 2, 5 or 10 residues). Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

The aexA gene overexpressed in a fungus, in particular examples, includes a sequence that encodes an aexA protein having at least 60%, at least 65%, at least 69%, at least 70%, at least 71%, at least 75%, at least 80%, at least 85%, at least 90%, at least 95%, at least 96%, at least 97%, at least 98%, at least 99%, or 100% sequence identity to a aexA protein sequence, such as SEQ ID NO: 2, 3, 4 and 5, wherein the protein can export aconitic acid from a cell. In a specific example, the aexA gene inactivated in a fungus encodes an aexA protein shown in SEQ ID NO: 2, 3, 4 and 5.

The aexA gene that is to be overexpressed in a fungus, in particular examples, includes a sequence (such as a coding sequence) having at least 60%, at least 65%, at least 69%, at least 70%, at least 71%, at least 75%, at least 80%, at least 85%, at least 90%, at least 95%, at least 96%, at least 97%, at least 98%, at least 99%, or 100% sequence identity to a aexA nucleic acid sequence, such as SEQ ID NO: 1, and encodes an aexA protein that can export aconitic acid from a cell. In a specific example, the aexA gene overexpressed in a fungus is the sequence of SEQ ID NO: 1.

One skilled in the art will appreciate that additional aexA sequences can be identified. For example, aexA nucleic acid molecules that encode an aexA protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known aexA sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes an aexA protein. Briefly, any known aexA nucleic acid molecule (e.g., SEQ ID NO: 1), or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is an aexA protein.

C. Methods of Functionally Deleting cadA

As used herein, an "inactivated" or "functionally deleted" cadA gene means that the cadA gene has been mutated, for example by insertion, deletion, or substitution (or combinations thereof) of one or more nucleotides such that the mutation substantially reduces (and in some cases abolishes) expression or biological activity of the encoded cadA gene product. The mutation can act through affecting transcription or translation of the cadA gene or its mRNA, or the mutation can affect the cadA polypeptide product itself in such a way as to render it substantially inactive.

In one example, a strain of *Aspergillus* (such as one that is aexA+) is transformed with a vector which has the effect of down-regulating or otherwise inactivating a cadA gene. This can be done by mutating control elements such as promoters and the like which control gene expression, by mutating the coding region of the gene so that any protein expressed is substantially inactive, or by deleting the cadA gene entirely. For example, a cadA gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). In one example, the cadA gene is genetically inactivated by inserting coding sequences for aexA, panD, BAPAT, and/or 3-HPDH. Thus, the disclosure provides transformed fungi that include at least one exogenous nucleic acid molecule which genetically inactivates an endogenous cadA gene. In one example, aexA+/ΔcadA cell produces more aconitic acid, for example relative to a comparable fungus with native or wild-type aexA expression.

In particular examples, an insertional mutation includes introduction of a sequence that is in multiples of three bases (e.g., a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded cadA polypeptide or expression of a substantially inactive polypeptide. Mutations can also be generated through insertion of foreign gene sequences, for example the insertion of a gene encoding antibiotic resistance (such as hygromycin or bleomycin), or aexA, panD, BAPAT, and/or 3-HPDH coding sequences.

In one example, genetic inactivation is achieved by deletion of a portion of the coding region of an endogenous cadA gene. For example, some, most (such as at least 50%) or virtually the entire endogenous coding region can be deleted. In particular examples, about 5% to about 100% of the endogenous gene is deleted, such as at least 20% of the gene, at least 40% of the gene, at least 75% of the gene, or at least 90% of the endogenous cadA gene.

Deletion mutants can be constructed using any of a number of techniques. In one example, homologous double crossover with fusion PCR products is employed to genetically inactivate cadA in Aspergillus.

In one example, counterselectable markers are employed to delete genes (see Reyrat et al., Infec. Immun. 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselecteable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., Appl. Environ. Microbiol. 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., cadA) can be deleted in the Aspergillus genome and to replace it with a selectable marker (for example a gene coding for kanamycin resistance) that is flanked by the lox sites. Transient expression (by electroporation of a suicide plasmid containing the cre gene under control of a promoter that functions in Aspergillus) of the cre recombinase should result in efficient elimination of the lox flanked marker. This process will produce a mutant containing the desired deletion mutation and one copy of the lox sequence.

In another method, an endogenous cadA gene sequence in the Aspergillus genome is replaced with a marker gene, such as green fluorescent protein, β-galactosidase, or luciferase. In this technique, DNA segments flanking a desired deletion are prepared by PCR and cloned into a suicide (non-replicating) vector for Aspergillus. An expression cassette, containing a promoter active in Aspergillus and the appropriate marker gene, is cloned between the flanking sequences. The plasmid is introduced into wild-type Aspergillus. Fungi that incorporate and express the marker gene are isolated and examined for the appropriate recombination event (replacement of the wild type cadA gene with the marker gene).

Thus, for example, a fungal cell can be engineered to have a disrupted cadA gene using mutagenesis or knock-out technology. (Methods in Yeast Genetics (1997 edition), Adams, Gottschling, Kaiser, and Sterns, Cold Spring Harbor Press, 1998; Datsenko and Wanner, Proc. Natl. Acad. Sci. USA 97: 6640-5, 2000; and Dai et al., Appl. Environ. Microbiol. 70(4):2474-85, 2004). Alternatively, antisense technology can be used to reduce or eliminate the activity of cadA. For example, a fungal cell can be engineered to contain a cDNA that encodes an antisense molecule that prevents cadA from being translated. The term "antisense molecule" encompasses any nucleic acid molecule or nucleic acid analog (e.g., peptide nucleic acids) that contains a sequence that corresponds to the coding strand of an endogenous cadA gene. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of cadA.

In one example, to genetically inactivate cadA in A. pseudoterreus or A. terreus, protoplast transformation is used, for example as described in Example 1. For example, conidia of Aspergillus are grown in liquid complete medium at room temperature (e.g., about 20-35° C., such as 30° C.) and grown for at least 12 hours (such as at least 16 hours, or at least 18 hours, such as 12-24 hours, or 16-18 hours), at least 100 rpm, such as at least 150 rpm, at least 200 rpm for example 100 to 200 rpm. The resulting mycelia are subsequently harvested, for example by filtration. Protoplasts are prepared, for example by treating the harvested mycelia with a lysing enzyme (for example in an osmotic wash buffer for at least 30 min, at least 60 min, at least 120 min, or at least 240 min, such as 2 h). The resulting protoplasts are collected (e.g., by filtering). Protoplasts can be washed, for example with a Washing Solution (0.6M KCl, 0.1M Tris/HCl, pH 7.0) and Conditioning Solution (0.6M KCl, 50 mM $CaCl_2$, 10 mM Tris/HCl, pH 7.5). The protoplasts are transformed, for example in the conditioning solution. In some examples, at least 0.5 ug, at least 1 ug, or at least 2 ug of DNA (such as 1-2 ug DNA) is added to at least $10^6$ protoplasts (such as at least $10^7$ or $2\times10^7$ protoplasts). Polyethylene glycol (PEG), such as PEG8000 is added (such as 25% PEG8000, 0.6M KCl, 50 mM $CaCl_2$, 10 mM Tris/HCl, and pH 7.5) and the reaction incubated for at least 5 min (such as at least 10 min, at least 20 min, or at least 30 min, such as 10-30 min, 15-20 min, or 20 min) on ice. Additional PEG solution can be added and the reaction incubated for at least 1 min, at least 3 min, or at least 5 min, on ice. Conditioning Solution is added to the reaction, and the protoplast suspension mixed with warm selection agar (Minimal media+0.6M KCl+1.5% Agar+100 ug/ml hygromycin) (such as at 50° C.), and poured directly onto petri dish plates and allowed to solidify. Solidified plates can be inverted and incubated overnight at room temperature (e.g., about 20-35° C., such as 30° C.). The following day, the plates can be overlaid with Minimal Medium containing a selection antibiotic, such as hygromycin. Colonies appear after 3-4 days. Transformants can be excised and transferred to MM plate containing the selection antibiotic.

D. Measuring cadA Gene Inactivation

A fungus having an inactivated endogenous cadA gene can be identified using known methods. For example, PCR and nucleic acid hybridization techniques, such as Northern and Southern analysis, can be used to confirm that a fungus has a genetically inactivated cadA gene. In one example, real-time reverse transcription PCR (qRT-PCR) is used for detection and quantification of targeted messenger RNA, such as mRNA of cadA gene in the parent and mutant strains as grown at the same culture conditions. Immunohistochemical and biochemical techniques can also be used to determine if a cell expresses cadA by detecting the expression of the cadA peptide encoded by cadA. For example, an antibody having specificity for cadA can be used to determine whether or not a particular fungus contains a functional nucleic acid encoding cadA protein. Further, biochemical techniques can be used to determine if a cell contains a cadA gene inactivation by detecting a product produced as a result of the lack of expression of the peptide. For example, production of aconitic acid by *A. terreus* or *A. pseudoterreus* can indicate that such a fungus contains an inactivated cadA gene.

E. Measuring Aconitic Acid Production

Methods of determining whether a overexpression of aexA and/or genetic inactivation of cadA in *Aspergillus*, such as *A. terreus* or *A. pseudoterreus*, increases aconitic acid production, for example relative to the same strain of *A. terreus* or *A. pseudoterreus* with native aexA expression and/or a native cadA sequence (such as a parental strain), are provided herein. Although particular examples are disclosed herein, the methods are not limiting.

For example, production of aconitic acid by *Aspergillus* (such as an aexA+ or aexA+/ΔcadA strain) can be measured using a spectrophotometric assay, by liquid chromatography (LC), or high-pressure liquid chromatography (HPLC) methods. In some examples, the supernatant of the fungus is analyzed for the presence of aconitic acid. In some examples, the culture media containing the aexA+ or aexA+/ΔcadA strain is filtered prior to measuring aconitic acid in the culture media (supernatant).

F. cadA Sequences cadA protein and nucleic acid sequences are publicly available and specific examples are provided herein. In addition, cadA sequences can be identified using molecular biology methods.

Examples of cadA nucleic acid sequences are shown in SEQ ID NOS: 6, 8, 10 and 11. However, the disclosure also encompasses variants of SEQ ID NOS: 6, 8, 10 and 11 which encode a functional cadA protein. One skilled in the art will understand variants of the cadA nucleic acid sequences provided herein can be genetically inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Such variant cadA nucleic acid molecules can share at least 60%, at least 70%, at least 80%, at least 85%, at least 90%, at least 95%, at least 96%, at least 97%, at least 98%, or at least 99% sequence identity to any cadA nucleic acid sequence, such as SEQ ID NO: 6, 8, 10 or 11.

Examples of cadA protein sequences are shown in SEQ ID NOS: 7 and 9. However, the disclosure also encompasses variants SEQ ID NOS: 7 and 9 which retain cadA activity. One skilled in the art will understand that variants of these cadA enzyme sequences can be inactivated. Variant sequences can be identified, for example by aligning known cadA sequences. Variant sequences may contain a single insertion, a single deletion, a single substitution, multiple insertions, multiple deletions, multiple substitutions, or any combination thereof (e.g., single deletion together with multiple insertions). Such cadA peptides share at least 80%, at least 85%, at least 90%, at least 95%, at least 97%, at least 98%, or at least 99% sequence identity to a cadA protein sequence, such as SEQ ID NO: 7 or 9.

In some examples, a cadA sequence that is to be genetically inactivated encodes or includes one or more conservative amino acid substitutions. In one example, a cadA protein sequence (such as SEQ ID NO: 7 or 9) includes one or more amino acid substitutions, such as conservative substitutions (for example at 1, 2, 5 or 10 residues). Examples of amino acids which may be substituted for an original amino acid in a protein and which are regarded as conservative substitutions are provided above.

The cadA gene inactivated in a fungus, in particular examples, includes a sequence that encodes a cadA protein having at least 60%, at least 70% at least 80%, at least 85%, at least 90%, at least 95%, at least 96%, at least 97%, at least 98%, at least 99%, or 100% sequence identity to a cadA protein sequence, such as SEQ ID NO: 7 or 9, wherein the protein can catalyze the decarboxylation of cis-aconitate to itaconate and $CO_2$ and vice versa. In a specific example, the cadA gene prior to its inactivation encoded a cadA protein shown in SEQ ID NO: 7 or 9.

The cadA gene that is to be inactivated in a fungus, in particular examples, includes a sequence (such as a coding sequence) having at least 60%, at least 70%, at least 80%, at least 85%, at least 90%, at least 95%, at least 97%, at least 98%, at least 99%, or 100% sequence identity to a cadA nucleic acid sequence, such as SEQ ID NO: 6, 8, 10, or 11, and encodes a cadA protein that can catalyze the decarboxylation of cis-aconitate to itaconate and $CO_2$ and vice versa. In a specific example, the cadA gene inactivated in a fungus is the sequence of SEQ ID NO: 6 or 8.

One skilled in the art will appreciate that additional cadA sequences can be identified. For example, cadA nucleic acid molecules that encode a cadA protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known cadA sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes a cadA protein. Briefly, any known cadA nucleic acid molecule (such as SEQ ID NO: 6, 8, 10, or 11), or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a cadA protein.

G. panD, BAPAT, and 3-HPDH Sequences panD, BAPAT, and 3-HPDH protein and nucleic acid sequences are publicly available and specific examples are provided herein. In addition, panD, BAPAT, and 3-HPDH sequences can be identified using molecular biology methods.

Exemplary of panD coding sequences are shown in SEQ ID NO: 12 and 14. However, the disclosure also encompasses variants of SEQ ID NO: 12 and 14 which encode a functional panD protein. Exemplary of BAPAT coding sequences are shown in SEQ ID NO: 15 and 17. However, the disclosure also encompasses variants of SEQ ID NO: 15 and 17 which encode a functional BAPAT protein. Exemplary of 3-HPDH coding sequences are shown in SEQ ID NO: 18 and 20. However, the disclosure also encompasses variants of SEQ ID NO: 18 and 20 which encode a functional 3-HPDH protein.

One skilled in the art will understand variants of the panD, BAPAT, and 3-HPDH nucleic acid sequences provided herein can be introduced into (or be endogenous to) an Aspergillus fungus, such as a aexA+ or aexA+/ΔcadA Aspergillus, such as inserting panD, BAPAT, and 3-HPDH expression sequences into the native cadA gene to inactivate it. Variant panD, BAPAT, and 3-HPDH sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. In some examples, a panD, BAPAT, and 3-HPDH sequence expressed in an Aspergillus fungus is codon optimized for expression in Aspergillus, such as Aspergillus terreus or pseudoterreus. Such variant panD, BAPAT, and 3-HPDH nucleic acid molecules in some examples share at least 60%, at least 70%, at least 75%, at least 80%, at least 85%, at least 90%, at least 95%, at least 96%, at least 97%, at least 98%, at least 99%, or 100% sequence identity to any panD, BAPAT, and 3-HPDH nucleic acid sequence, such as SEQ ID NO: 12, 15, or 18, respectively, or SEQ ID NO: 14, 17, or 20, respectively.

Exemplary panD, BAPAT, and 3-HPDH protein sequences are shown in SEQ ID NOS: 13, 16, and 19, respectively. However, the disclosure also encompasses variants SEQ ID NOS: 13, 16, and 19 which retain panD, BAPAT, and 3-HPDH activity, respectively. One skilled in the art will understand that variants of these panD, BAPAT, and 3-HPDH sequences can be expressed in an Aspergillus fungus, such as aexA+ or aexA+/ΔcadA Aspergillus, Variant sequences can be identified, for example by aligning known panD, BAPAT, and 3-HPDH sequences. Variant sequences may contain a single insertion, a single deletion, a single substitution, multiple insertions, multiple deletions, multiple substitutions, or any combination thereof (e.g., single deletion together with multiple insertions). Such panD, BAPAT, and 3-HPDH peptides expressed in a aexA+ or aexA+/ΔcadA Aspergillus in some examples share at least 60%, at least 70%, at least 75%, at least 80%, at least 85%, at least 90%, at least 95%, at least 96%, at least 97%, at least 98%, at least 99%, or 100% sequence identity to a panD, BAPAT, and 3-HPDH protein sequence, such as SEQ ID NO: 13, 16, or 19, respectively.

In some examples, a panD, BAPAT, and 3-HPDH sequence that is to be expressed in an aexA+ or aexA+/ΔcadA Aspergillus fungus encodes or includes one or more conservative amino acid substitutions. In one example, a panD, BAPAT, or 3-HPDH sequence (such as SEQ ID NO: 13, 16, and 19, respectively) includes one or more amino acid substitutions, such as conservative substitutions (for example at 1, 2, 5, or 10 residues). Examples of conservative substitutions are provided above.

The panD, BAPAT, and 3-HPDH gene expressed in a aexA+ or aexA+/ΔcadA fungus, in particular examples, includes a sequence that encodes a panD, BAPAT, and 3-HPDH protein having at least 60%, at least 70%, at least 75%, at least 80%, at least 85%, at least 90%, at least 95%, at least 96%, at least 97%, at least 98%, at least 99%, or 100% sequence identity to a panD, BAPAT, and 3-HPDH protein sequence, such as SEQ ID NO: 13, 16, and 19, respectively, wherein the variant protein has the biological activity of panD, BAPAT, or 3-HPDH, respectively. In a specific example, the panD, BAPAT, and 3-HPDH gene expressed in an aexA+ or aexA+/ΔcadA fungus encodes the protein shown in SEQ ID NO: 13, 16, or 19, respectively.

One skilled in the art will appreciate that additional panD, BAPAT, and 3-HPDH sequences can be identified. For example, panD, BAPAT, and 3-HPDH nucleic acid molecules that encode a panD, BAPAT, and 3-HPDH protein, respectively can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with panD, BAPAT, or 3-HPDH sequences. Sequence alignment software such as MEGALIGN (DNASTAR, Madison, WI, 1997) can be used to compare various sequences.

In addition, nucleic acid hybridization techniques can be used to identify and obtain a nucleic acid molecule that encodes a panD, BAPAT, or 3-HPDH protein. Briefly, any known panD, BAPAT, or 3-HPDH nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a panD, BAPAT, or 3-HPDH protein.

In one example, exogenous panD, BAPAT, and/or 3-HPDH nucleic acid sequences are introduced into Aspergillus using protoplast transformation, for example as described in Example 1 (and described above).

H. Measuring Gene Expression

An aexA+ or aexA+/ΔcadA fungus expressing aexA, panD, BAPAT, and/or 3-HPDH can be identified using known methods. For example, PCR and nucleic acid hybridization techniques, such as Northern, RT-PCR, and Southern analysis, can be used to confirm that a fungus expresses (such as overexpresses) aexA, panD, BAPAT, and/or 3-HPDH such as an increase in the aexA, panD, BAPAT, and/or 3-HPDH copy number. Immunohisto-chemical and biochemical techniques can also be used to determine if a cell expresses or overexpresses aexA, panD, BAPAT, and/or 3-HPDH by detecting the expression of the aexA, panD, BAPAT, and/or 3-HPDH peptide encoded by aexA, panD, BAPAT, and/or 3-HPDH, respectively. For example, an antibody having specificity for aexA, panD, BAPAT, and/or 3-HPDH can be used to determine whether or not a particular fungus has increased aexA, panD, BAPAT, and/or 3-HPDH protein expression, respectively. Further, biochemical techniques can be used to determine if a cell has increased aexA, panD, BAPAT, and/or 3-HPDH expression by detecting a product produced as a result of the expression of the peptide. For example, production of 3-HP by aexA+ or aexA+/ΔcadA *Aspergillus* can indicate that such a fungus expresses or overexpresses aexA, panD, BAPAT, and 3-HPDH.

I. Measuring 3-HP Production

Methods of determining whether an aexA+ or aexA+/ΔcadA fungus that also expresses panD, BAPAT, and 3-HPDH has increased 3-HP production, for example relative to the same strain with a native aexA sequence, (such as a parental strain) include HPLC.

Methods of Producing Aconitic Acid (AA)

The recombinant *Aspergillus* fungi provided herein (aexA+ or aexA+/ΔcadA), can be used to produce AA (for example for as a building block for other materials, such as polymers). Such fungi can be from any *Aspergillus* species, such as *Aspergillus terreus* or *pseudoterreus*. For example, the disclosure provides methods of making AA (such as cis-aconitic acid, trans-aconitic acid, or both), which can include culturing the disclosed fungi under conditions that permit the fungus to make AA, for example in Riscaldati medium.

In some examples, the aexA+ or aexA+/ΔcadA fungi are cultured at room temperature (e.g., 20-35° C., such as about 30° C.) at normal atmospheric pressure (e.g., 1 atm). In some examples, the method includes purifying or isolating the AA, for example from the culture media or from the cultured fungus. In some examples, the AA is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making AA include culturing the aexA+ or aexA+/ΔcadA *Aspergillus* provided herein t, under conditions that permit the fungus to make AA. In general, the culture media and/or culture conditions can be such that the fungi grow to an adequate density and produce AA efficiently. In one example the ΔcadA fungi are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$). In one example the aexA+ or aexA+/ΔcadA *Aspergillus* fungi provided herein are cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the aexA+ or aexA+/ΔcadA *Aspergillus* fungi are cultured or grown in a liquid Riscaldati medium at about 20 to 35° C. (such as 20° C. to 30° C., 25° C. to 30° C., 28 to 32° C., or 30° C.) with rotation (such as at least 100 rpm, at least 120 rpm, at least 150 rpm, at least 170 rpm, or at least 200 rpm, such as 200 rpm) at normal pressure.

In one example, the aexA+ or aexA+/ΔcadA fungi are grown in culture containers (such as baffled flasks, and in some examples are silanized (5% solution of dichlorodimethylsilane in heptane (Sigma, St. Louis, MO)). Each culture container is inoculated with spores (such as at least $2 \times 10^6$ spores/ml) and incubated for at least 3 days, at least 4 days, at least 5 days, at least 7 days, or at least 10 days at 30° C. and 100 to 250 rpm to obtain AA.

In one example, the aexA+ or aexA+/ΔcadA *Aspergillus*, produce more AA than a corresponding fungus with wild-type or native levels of aexA (and in some examples also native levels of cadA). In specific examples, the disclosed fungi produce at least 20 g/l of total AA after 7 days, for example at least 25 g/l, at least 30 g/l, at least 40 g/l, at least 45 g/l, at least 46 g/l, at least 47 g/l, at least 48 g/l, at least 49 g/l or at least 50 g/l after at least 7 days, at least 8 days, or at least 10 days, such as after 5 to 8 days, 5 to 10 days, or 6 to 7 days) when grown in Riscaldati medium at 30° C. with 200 rpm shaking. In specific examples, the aexA+ or aexA+/ΔcadA fungi yield at least 0.5 g/g of total AA after 7 days, for example at least 0.6 g/g or at least 0.7 g/g after at least 7 days, at least 8 days, or at least 10 days, such as after 5 to 8 days, 5 to 10 days, or 6 to 7 days when grown in Riscaldati medium at 30° C. with 200 rpm shaking. In specific examples, the aexA+ or aexA+/ΔcadA fungi produce AA at a rate of at least 0.1 g/L/hr after at least 7 days, for example at least 0.2 g/L/hr, at least 0.25 g/L/hr, or at least 0.3 g/L/hr, after at least 7 days, at least 8 days, or at least 10 days, such as after 5 to 8 days, 5 to 10 days, or 6 to 7 days) when grown in Riscaldati medium at 30° C. with 200 rpm shaking.

In some examples, the method further includes isolating the AA made by the aexA+ or aexA+/ΔcadA *Aspergillus*. Once produced, any method can be used to isolate the AA. For example, separation techniques (such as filtration) can be used to remove the fungal biomass from the culture medium, and isolation procedures (e.g., filtration, distillation, precipitation, electrodialysis, and ion-exchange procedures) can be used to obtain the AA from the broth (such as a fungi-free broth). In addition, the AA can be isolated from the culture medium after the AA production phase has been terminated.

Methods of Producing 3-HP

The aexA+ or aexA+/ΔcadA *Aspergillus*), can further express endogenous or exogenous panD, BAPAT, and 3-HPDH, and thus be used to produce 3-HP

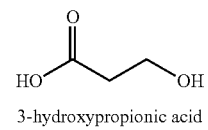

3-hydroxypropionic acid (for example for as a building block for other materials, such as acrylonitrile, acrylic acid by dehydration, malonic acid by oxidation, esters by esterification reactions with alcohols, and reduction to 1,3 propanediol). Such fungi can be from any *Aspergillus* species, such as *Aspergillus terreus*, *Aspergillus niger*, or *Aspergillus pseudoterreus*. For example, the disclosure provides methods of making 3-HP, which can include culturing the disclosed fungi that also express panD, BAPAT, and 3-HPDH under conditions that permit the fungus to make 3-HP, for example in Riscaldati medium (such as modified Riscaldati medium with 20× trace elements).

In some examples, the aexA+ or aexA+/ΔcadA *Aspergillus* provided herein, and further express endogenous or exogenous panD, BAPAT, and 3-HPDH, are cultured at room temperature (e.g., 20-35° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making 3-HP include culturing aexA+ or aexA+/ΔcadA *Aspergillus* fungi provided herein, and further express endogenous or exogenous panD, BAPAT, and 3-HPDH, under conditions that permit the fungus to make 3-HP. In general, the culture media and/or culture conditions can be such that the fungi grow to an adequate density and produce 3-HP efficiently. In one example the aexA+ or aexA+/ΔcadA fungi that further express panD, BAPAT, and 3-HPDH are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$, which may include 20× trace elements). In one example such fungi are 20 cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the aexA+ or aexA+/ΔcadA fungi that also express panD, BAPAT, and 3-HPDH are cultured or grown in a liquid modified Riscaldati medium with 20× trace elements at about 20 to 35° C. (such as 20° C. to 30° C., 25° C. to 30° C., 28 to 32° C., or 30° C.) with rotation (such as at least 100 rpm, at least 120 rpm, such as 150 or 200 rpm) at normal pressure.

In one example, the aexA+ or aexA+/ΔcadA fungi are grown in culture containers (such as baffled flasks, and in some examples are silanized (5% solution of dichlorodimethylsilane in heptane (Sigma, St. Louis, MO)). Each culture container is inoculated with spores (such as at least $10^6$ spores/ml) and incubated for at least 3 days, at least 4 days, at least 5 days, or at least 10 days at 30° C. and 100 to 300 rpm (such as 150 or 200 rpm) to obtain 3-HP.

In one example, the aexA+ or aexA+/ΔcadA *Aspergillus* can further express endogenous or exogenous panD, BAPAT, and 3-HPDH produce more 3-HP than a corresponding fungus with wild-type levels of axeA (and in some examples wild-type levels of cadA), either with or without panD, BAPAT, and 3-HPDH expression. In specific examples, the aexA+ or aexA+/ΔcadA *Aspergillus* can further express endogenous or exogenous panD, BAPAT, and 3-HPDH produce at least 0.1 g/l of 3-HP after at least 4 days, for example at least 0.2 g/l, at least 0.25 g/l, at least 0.3 g/l, at least 0.4 g/l, at least 0.5 g/l, at least 0.6 g/l, at least 0.7 g/l, at least 0.8 g/l, at least 0.9 g/l, at least 1.1 g/l, at least 1.2 g/l, at least 1.5 g/l, 1.6 g/l, at least 2 g/l, at least 3 g/l, at least 4 g/l, at least 5 g/l, at least 6 g/l, at least 7 g/l, or at least 8 g/l, after at least 5 days, at least 6 days, at least 7 days, at least 8 days, or at least 10 days, such as after 4 to 6 days, 8 to 10 days, or 4 to 5 days (such as at least 6.5 g/l, at least 7 g/l, at least 7.5 g/l, at least 8 g/l, or at least 8.5 g/l after at least 7 days), when grown in Riscaldati medium (such as modified Riscaldati medium with 20× trace elements) at 30° C. with 150 or 200 rpm shaking.

In some examples, the method further includes isolating the 3-HP made by the disclosed fungi. Once produced, any method can be used to isolate the 3-HP. For example, separation techniques (such as filtration) can be used to remove the fungal biomass from the culture medium, and isolation procedures (e.g., filtration, distillation, precipitation, electrodialysis, and ion-exchange procedures) can be used to obtain the 3-HP from the broth (such as a fungi-free broth). In addition, the 3-HP can be isolated from the culture medium after the 3-HP production phase has been terminated.

Compositions and Kits

Also provided by the present disclosure are compositions that include isolated aexA+ or aexA+/ΔcadA fungi (which in some examples also express panD, BAPAT, and 3-HPDH, such as exogenous panD, BAPAT, and 3-HPDH proteins), such as a medium for culturing, storing, or growing the fungus. In some examples, the *Aspergillus* in the composition are freeze dried or lyophilized.

Also provided by the present disclosure are kits that include isolated aexA+ or aexA+/ΔcadA fungi (which in some examples also express panD, BAPAT, and 3-HPDH, such as exogenous panD, BAPAT, and 3-HPDH proteins), such as a kit that includes a medium for culturing, storing, or growing the fungus. In some examples, the fungi in the kit are freeze dried or lyophilized. In some examples, the kit further includes one or more reagents for transforming *Aspergillus*, such as protoplast isolation buffer, osmotic wash buffer, polyethylene glycol, filtration material (such as miracloth), antibiotic (e.g., hygromycin), or combinations thereof.

Exemplary mediums include that can be in the disclosed compositions and kits include solid medium (such as those containing agar, for example complete medium (CM) or minimal medium (MM)) and liquid media (such as a fermentation broth, such as CM, MM, or CAP medium). In one example, the kit or composition includes Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$), for example

| | Conc. (g/L) | Amount | Notes |
|---|---|---|---|
| Glucose | 100 | 100 g | |
| $KH_2PO_4$ | 0.11 | 0.11 g | |
| $(NH_4)_2SO_4$ | 2.36 | 2.36 g | |
| $MgSO_4 * 7H_2O$ | 2.08 | 2.08 g | |
| NaCl | 0.074 | 0.074 g | |
| $CaCl_2 * 2H_2O$ | 0.13 | 0.13 g | |
| $ZnSO_4 * 7H_2O$ | 0.0013 | 0.0013 g | Use 1000 X soln. |
| $FeSO_4 * 7H_2O$ | 0.0055 | 0.0055 g | " |
| $CuSO_4 * 5H_2O$ | 0.0002 | 0.0002 g | " |
| $MnCl_2 * 4H_2O$ | 0.0007 | 0.0007 g | " |
| DI Water (L) | | 1 L | |
| Autoclave Time | | 15 min for small flasks 30 min for large flasks 30-60 for fermenter | |
| Comments: | | Adjust to pH = 3.4 with $H_2SO_4$ | |

In one example, the kit or composition includes a modified Riscaldati medium with 20× trace elements, for example 20 times of the following

| | | | |
|---|---|---|---|
| ZnSO$_4$ * 7H$_2$O | 0.0013 | 0.0013 g | Use 1000 X soln. |
| FeSO$_4$ * 7H$_2$O | 0.0055 | 0.0055 g | " |
| CuSO$_4$ * 5H$_2$O | 0.0002 | 0.0002 g | " |
| MnCl$_2$ * 4H$_2$O | 0.0007 | 0.0007 g | " |

Example 1

Materials and Methods

This example describes methods used in the experiments described in Examples 2-4 below.
Strains and Vectors The parental *A. pseudoterreus* strain ATCC 32359 was obtained from American Type Culture Collection (ATCC). The hygromycin phosphotransferase (hph) marker cassette was amplified from vector pCB1003 (Carroll et al., 1994). The Pyrithiamine resistance (ptrA) marker cassette was amplified from vector pRTR1 (Kubodera et al. 2000).
Growth Conditiona All strains were maintained on complete medium agar. The complete medium contained 10 g glucose, 2 g triptase peptone, 1 g yeast extract, 1 g casamino acid, 50 mL 20×NO$_3$ salts, 1 mL of 1000× trace elements, and 1 mL of 1000× vitamin stock in 1 L deionized water with pH adjusted to 6.5 with 1M NaOH. One liter of the 20×NO$_3$ salts contained: 120 g Na$_2$NO$_3$, 10.4 g KCl, 10.4 g MgSO$_4$.7H$_2$O, and 30.4 g KH$_2$PO$_4$. The 1000× vitamin stock solution contained in per 100 ml H$_2$O: 0.01 g biotin, 0.01 g pyridoxine-HCl, 0.01 g thiamine-HCl, 0.01 g riboflavin, 0.01 g para-aminobenzoic acid, and 0.01 g nicotinic acid. The vitamin stock solution was filtered and stored at 4° C. The 1000× trace element contained in per 100 ml de-ionized H$_2$O: 2.2 g ZnSO$_4$.7H$_2$O, 1.1 g H$_3$BO$_3$, 0.5 g MnCl$_2$.4H$_2$O, 0.5 g FeSO$_4$.7H$_2$O, 0.17 g CoCl$_2$.6H$_2$O, 0.16 g CuSO$_4$.5H$_2$O, 0.15 g Na$_2$MoO$_4$.2H$_2$O, and 5 g Na$_2$EDTA. The trace element constituents were added in the listed order and mixed. Then the pH was adjusted to 6.5 with KOH and the de-ionized H$_2$O was added to the final volume of 100 ml. The trace elements stock solution was filtered and stored at 4° C.

The transformants were selected for hygromycin resistance on the agar plates of minimum media (10 g glucose, 50 mL 20×NO$_3$ salts, 1 mL 1000× trace elements, and 1 mL 1000× vitamin stock in 1 L de-ionized H$_2$O with pH adjusted to 6.5 with 1M NaOH, 100 mg/L hygromycin B). The IA production medium is Riscaldati medium as described previously (Riscaldati et al., 2000), which contained 100 g glucose, 0.11 g KH$_2$PO$_4$, 2.36 g (NH$_4$)$_2$SO$_4$, 2.08 g MgSO$_4$.7H$_2$O, 0.074 g NaCl, 0.13 g CaCl$_2$.2H$_2$O, and 1 mL 1000× trace elements in 1 L de-ionized water with the pH adjusted to 3.4 with 1M H$_2$SO$_4$. One liter of the 1000× trace element solution contained 1.3 g ZnSO$_4$.7H$_2$O, 5.5 g FeSO$_4$.7H$_2$O, 0.2 g CuSO$_4$.5H$_2$O, and 0.7 g MnCl$_2$.4H$_2$O.

Conidia of spore were grown on the agar plate of complete medium for five days and then harvested by washing them with sterile 0.4% Tween 80 solution. Samples for EST analysis were collected from *A. pseudoterreus* ATCC32359 grown in a 20 L Riscaldati medium in a 30 L stirred tank bioreactor. Other experiments were performed in shake flasks. In shake flasks experiments, approximately 2×10$^6$ conidia/mL were inoculated into 30 mL of Riscaldati medium in a 125 ml Erlenmeyer flask. Cultivation was performed at 30° C. on a rotary shaker at 200 rpm. At intervals during the incubation period, three single flasks were harvested for high-performance liquid chromatography (HPLC) analysis, biomass measurement, and RNA extraction. All experiments were carried out in triplicate, and the standard deviation of the IA concentration or dry weight was always less than 10% of the mean.
Construction of Deletion and Overexpression Mutants The deletion and overexpression mutants were constructed by Gibson assembly (Gibson et al. 2010, Gibson et al. 2009) as described in the Gibson Assembly master mix protocol from NEB (Cat #E2611S). Synthetic oligos used for each construct are provided in Tables 1 and 2.

TABLE 1

Oligo sequences for making deletion constructs

| name | sequence | Seq id no |
|---|---|---|
| mfsA up_fwd | aggtcgacggtatcgatagtttaaacgtgaaagagattgaggatc | 34 |
| mfsA up_rev | gtctgtcagaccaatagataccaatgagg | 35 |
| mfsA ptrA_fwd | tatctattggtctgacagacgggcaattg | 36 |
| mfsA ptrA_rev | cattgcagaggagccgctcttgcatctttg | 37 |
| mfsA down_fwd | agagcggctcctctgcaatggatggccttc | 38 |
| mfsA down_rev | gatccccgggctgcagtttaaacgtggcgaggtgaacatctc | 39 |
| 2022 up_fwd | aggtcgacggtatcgatagtttaaaccagttccaacagtggagtg | 40 |
| 2022 up_rev | gtctgtcagaggatacccatcgtgggatg | 41 |
| 2022 ptrA_fwd | atgggtatcctctgacagacgggcaattg | 42 |
| 2022 ptrA_rev | catcccgcacgagccgctcttgcatctttg | 43 |
| 2022 down_fwd | agagcggctcgtgcgggatggggtgtga | 44 |
| 2022 down_rev | ggatccccgggctgcagtttaaacactgtcccagaggtccgtc | 45 |
| 2739 up_fwd | aggtcgacggtatcgatagtttaaacggtaatctcggaattcgc | 46 |
| 2739 up_rev | gtctgtcagaaggaggacattgtgagtag | 47 |

TABLE 1-continued

Oligo sequences for making deletion constructs

| name | sequence | Seq id no |
| --- | --- | --- |
| 2739 ptrA_fwd | atgtcctccttctgacagacgggcaattg | 48 |
| 2739 ptrA_rev | tgaaccagacgagccgctcttgcatctttg | 49 |
| 2739 down_fwd | agagcggctcgtctggttcaagtgaagcttg | 50 |
| 2739 down_rev | ggatccccgggctgcagtttaaacctcctcgagagctggagaac | 51 |
| 2945 up_fwd | aggtcgacggtatcgatagtttaaacgcacgacacaacacagtc | 52 |
| 2945 up_rev | gtctgtcagatcgacggcatgttcaagttg | 53 |
| 2945 ptrA_fwd | atgccgtcgatctgacagacgggcaattg | 54 |
| 2945 ptrA_rev | aacgcaccaggagccgctcttgcatctttg | 55 |
| 2945 down_fwd | agagcggctcctggtgcgttgatggagc | 56 |
| 2945 down_rev | gatccccgggctgcagtttaaacctcttgactatcgcgtatcac | 57 |
| 8846t1 up_fwd | aggtcgacggtatcgatagtttaaacagacgcattgctgttctac | 58 |
| 8846t1 up_rev | gtctgtcagatcgtgctcgtctctcgtc | 59 |
| 8846t1 ptrA_fwd | acgagcacgatctgacagacgggcaattg | 60 |
| 8846t1 ptrA_rev | caacatgctcgagccgctcttgcatctttg | 61 |
| 8846t1 down_fwd | agagcggctcgagcatgttgaatgttgc | 62 |
| 8846t1 down_rev | ggatccccgggctgcagtttaaacaagtcctcgacatggtctg | 63 |
| 9513 up_fwd | ggtcgacggtatcgatagtttaaaccctggtgatcttgtaagcag | 64 |
| 9513 up_rev | gtctgtcagagggagatcatggtctggatg | 65 |
| 9513 ptrA_fwd | atgatctccctctgacagacgggcaattg | 66 |
| 9513 ptrA_rev | tccccgatgggagccgctcttgcatctttg | 67 |
| 9513 down_fwd | agagcggctcccatcggggatggcctaag | 68 |
| 9513 down_rev | ggatccccgggctgcagtttaaactccacacgactgtcgaag | 69 |
| 9885 up_fwd | aggtcgacggtatcgatagtttaaacgcgagagactagtcgttg | 70 |
| 9885 up_rev | gtgatgccattacacggtag | 71 |
| 9885 ptrA_fwd | ctaccgtgtaatggcatcactctgacagacgggcaattg | 72 |
| 9885 ptrA_rev | cggcagtcctgagccgctcttgcatctttg | 73 |
| 9885 down_fwd | agagcggctcaggactgccggagttgttg | 74 |
| 9885 down_rev | ggatccccgggctgcagtttaaacctcatccaacgcaacggc | 75 |
| 9935 up_fwd | aggtcgacggtatcgatagtttaaacccgggtattagatgtgcg | 76 |
| 9935 up_rev | gtctgtcagactgtggacattgtgcggg | 77 |
| 9935 ptrA_fwd | atgtccacagtctgacagacgggcaattg | 78 |
| 9935 ptrA_rev | ggacatggaagagccgctcttgcatctttg | 79 |
| 9935 down_fwd | agagcggctcttccatgtccatctatcatg | 80 |
| 9935 down_rev | ggatccccgggctgcagtttaaacggttcatgacaatggatg | 81 |

TABLE 2

Oligo sequences for g8846 overexpression under the A. nidulus gpdA promoter

| name | sequence | Seq id no |
|---|---|---|
| pBSK + pgpdA_fwd | cgaggtcgacggtatcgatagtttaaacgttgacctagctg | 82 |
| g8846 + pgpdA_rev | ctctcgtcatggtgatgtctgctcaagc | 83 |
| g8846_fwd | agacatcaccatgacgagagacgagcac | 84 |
| g8846_rev | ggcatctacttcagtagccgtaaacagaag | 85 |
| tTrpC_fwd | cggctactgaagtagatgccgaccgcgg | 86 |
| tTrpC_rev | gtctgtcagatcgagtggagatgtggagtg | 87 |
| ptrA_fwd | ctccactcgatctgacagacgggcaattg | 88 |
| ptrA_rev + pBSK | agtggatcccccgggctgcagtttaaacgagccgctcttgcatc | 89 |

Oligonucleotides were from IDT (Coraville, Iowa). ExTaq polymerase (TaKaRa Bio USA, Mountain View, California) was used to generate DNA constructs for making gene knockouts. The final PCR product contains a hygromycin or pyrithiamine marker cassette flanked by sequences homologous to the upstream and the downstream regions of the target gene. Approximately 1~2 µg of the final product was used to transform the A. pseudoterreus strain.

Transformation of A. pseudoterreus Protoplasts

Approximately $2\times10^8$ conidia of A. pseudoterreus were added to 100 mL of complete medium in a 300 mL Erlenmeyer flask. The cultures were grown overnight (16 to 18 hours) at 30° C. on the rotary shaker at 200 rpm. The mycelia were harvested by filtering the culture through Miracloth and rinsed with 50 mL sterile water. Mycelia (mass of approximately 1 to 2 beans) were transferred into a 50 mL centrifuge tube containing 20 mL of protoplast isolation buffer (400 mg lysing enzyme (L1412, Sigma) dissolved in 20 mL of osmotic wash buffer (0.5 M KCl, and 10 mM sodium phosphate at pH 5.8) and incubated on the rotary shaker at 30° C. with gentle shaking at 70 rpm for 2 hours. Protoplasts were collected by filtering protoplasts through a sterile Miracloth into a 50 mL centrifuge tube and centrifuging at 1000 g for 10 minutes at 4° C. Protoplasts then were washed twice with 20 mL washing solution (0.6M KCl and 0.1M Tris/HCl at pH 7.0) and a third time in 10 mL conditioning solution (0.6M KCl, 50 mM $CaCl_2$, and 10 mM Tris/HCl and pH 7.5).

For transformation, 1 to 2 µg DNA was added to $2\times10^7$ protoplasts in 0.1 mL conditioning solution. A control reaction with no DNA was performed at the same time. Approximately 25 µL of polyethylene glycol (PEG) solution (25% PEG8000, 0.6 M KCl, 50 mM $CaCl_2$, and 10 mM Tris/HCl at pH 7.5) was added, and the protoplasts were incubated for 20 minutes on ice. An additional 500 µL of the PEG solution was added using a wide bore pipette tip and carefully mixed with the protoplasts by gently pipetting up and down one to two times. The protoplast solution then was incubated for 5 minutes on ice. One milliliter of cold conditioning solution was added and mixed by gently inverting the tube several times. The protoplast suspension was mixed with 12 mL of 50° C. selection agar (minimum media+0.6M KCl+1.5% Agar+100 µg/mL hygromycin B) in a 15 ml screwcap centrifuge tube. The mixtures were mixed by inverting the tubes three to four times and then poured directly onto the petri dish plates.

The control reaction was divided into a positive control plate (agar solution with no antibiotics) and a negative control (agar solution with 100 µg/mL hygromycin B). The solidified plates were incubated overnight at 30° C. The next day, the plates were overlaid with 12 mL of minimum media containing 150 µg/mL hygromycin B. Colonies started to appear after incubating for 3 to 4 days at 30° C. The transformants were excised and transferred onto minimum media slant containing 100 µg/mL hygromycin B. Correct transformants were confirmed by PCR approaches and Southern blotting analysis. The southern blotting procedure was done according to the previous description (Dai et al. 2013).

Mycelial Dry Cell Weight (DCW) Measurement

Mycelia dry cell weight at each time point was determined by harvesting the mycelia from a 30 ml culture onto a pre-weighed filter by suction filtration and washed once with 50 mL distilled water. Subsequently, the dry weight was determined after freeze-drying in a lyophilizer overnight in pre-weighed tubes with filters.

High-Performance Liquid Chromatography Analysis

Supernatant samples were passed through 0.22 µm filter and analyzed for IA, AA and glucose using high/performance liquid chromatography (HPLC) equipped with a Waters 2414 refractive index detector and a Waters 2489 UV/VIS detector. A Bio-Rad Aminex HPX-87H ion exclusion column (300 mm×7.8 mm) at 65° C. was used for analyte separation. Sulfuric acid (0.005 M) was used as eluent at a flow rate of 0.55 mL/min. IA was detected at 210 nm with a Waters 2414 refractive index detector (Waters, Milford, Massachusetts). Run time of each sample was 40 minutes.

Proteomics

Protein extractions were based on a previously established protocol (Kim and Heyman 2018, Nakayasu et al. 2016). Extracted proteins were dissolved in 100 mM $NH_4HCO_3$ containing 8 M urea and the protein concentration was measured by BCA assay. Disulfide bonds were reduced by adding dithiothreitol to a final concentration of 5 mM and incubating at 60° C. for 30 min. Samples were alkylated with a final concentration of 40 mM iodoacetamide for 1 h at 37° C. The reaction was then diluted 10-fold with 100 mM $NH_4HCO_3$ followed by the addition of $CaCl_2$ to 1 mM final concentration. Digestion was carried out for 3 h at 37° C. with 1:50 (wt:wt) trypsin-to-protein ratio. Salts and reagents were removed by solid-phase extraction using C18 cartridges according to the manufacturer instructions and the resulting peptides were dried in a vacuum centrifuge. The peptides were then resuspended in milliQ water and 500 ng of material was loaded onto in-house packed reversed-phase capillary columns (70-cm×75 μm i.d.) with 3-μm Jupiter C18.

The separation was carried out using a nanoAcquity HPLC system (Waters Corporation) at room temperature. The mobile phase A is 0.1% formic acid in water while mobile phase B is 0.1% formic acid in acetonitrile. The elution was carried out at 300 nL/min with the following gradient: 0-2 min 1% B; 2-20 min 8% B; 20-75 min 12% B; 75-97 min 30% B; 97-100 min 45%; 100-105 95%; 105-110 min 95%; 110-140 min 1%. MS analysis was carried out using a Q Exactive Plus (Thermo Fisher Scientific) in data dependent mode. Mass spectrometer settings were as following: full MS (AGC, 1×106; resolution, 30000; m/z range, 350-2000; maximum ion time, 20 ms); MS/MS (AGC, 1×105; resolution, 15000; m/z range, 200-2000; maximum ion time, 200 ms; minimum signal threshold, 2.5×104; isolation width, 2 Da; dynamic exclusion time setting, 45 s; collision energy, nce 30).

All mass spectrometry data were searched using MS-GF+ (Kim Sangtae and Pevzner 2014) and MASIC (Monroe et al. 2008) software. MS-GF+ software was used to identify peptides by scoring MS/MS spectra against peptides derived from the whole protein sequence database. MASIC software was used to generate the selected ion chromatographs (SICs) of all the precursors in MSMS datasets and calculate their peak areas as abundance. MASICResultsMerger (omics.pnl.gov/software/masic-results-merger) was used to append the relevant MASIC stats for each peptide hit result in MS-GF+. The MS-GF+ data were then filtered based on 1% false discovery rate (FDR) and less than 5-ppm mass accuracy to generate a list of qualified peptide hit results. The abundance of peptides was determined as the highest peak area identified for the peptide within a sample. Normalization of the data was performed with median centering based on the rank invariant peptides (Callister et al. 2006). Protein quantification was performed with standard reference-based median averages (Matzke et al. 2013). Statistics were performed with established standard methods (Webb-Robertson et al. 2017). For this specific dataset a t-test was utilized to evaluate comparisons of interest as well as a G-test to evaluate significance of presence/absence. Since only a subset of all possible comparisons are being made the p-values are adjusted via a Bonferroni.

Example 2

Identification of Cis-Aconitic Acid Transporters using Multi-Omics Analysis

AA and itaconic acid share the same biosynthesis pathway in the cell (FIG. 1). However, production level of AA is much lower than itaconic acid, which is 10 g/L versus 50 g/L. The only difference between AA and itaconic acid biosynthesis pathway is the transport across the plasma membrane. It was hypothesized AA uses a different transporter than itaconic acid, and that transport across the cell plasma membrane may be a limiting factor. The AA transporter was already saturated at 10 g/L.

Figure 2:
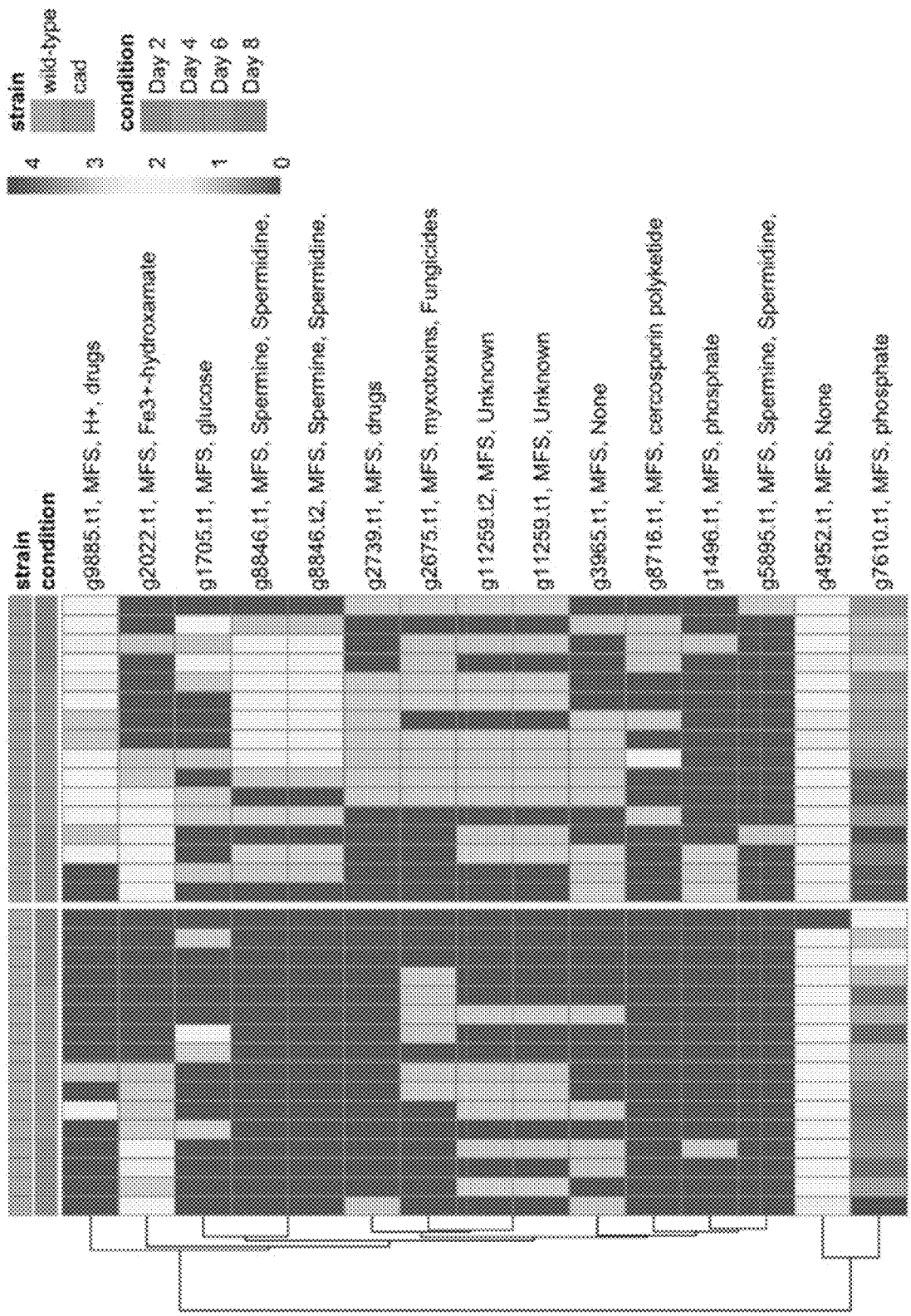
FIG. 2 is a digital heat map showing potential cis-aconitic acid transporters and their expression values from global proteomics of *A. pseudoterreus* wild-type and cadA deletion strains at 2, 4, 6, and 8 days of growth. Log2 of normalized spectral counts are shown as a clustered heatmap (blue—low, yellow—medium, and red—high expression). Row names show protein id, TCDB classification, and predicted substrates.

Global proteomics of *A. pseudoterreus* wild-type and cadA deletion strains were performed to identify potential transporters. First, proteins whose expression levels were responsive to cis-AA production were identified. Proteomics samples were taken at 2, 4, 6, and 8 days of the growth in four biological replicates. The potential transporters in *A. pseudoterreus* were annotated using the Transporter Classification Database (ncbi.nlm.nih.gov/pubmed/26546518). Global proteomics detected 7178 proteins out of 13430 annotated proteins, and 123 detected proteins were annotated as the Major Facilitator Superfamily (MFS) by TCDB. The MFS transporters were sorted by the difference of the log 2 normalized spectral counts between the wild-type and cad deletion strains, and the expression patterns of top 15 MFS transporters upregulated in the cadA deletion strain were visually inspected (FIG. 2). Four MFS transporters (g2022, g2739, g8846, and g9885) had higher expression in the cadA deletion strain versus the wild-type strain, and they were selected for further examination.

Example 3

Functional Deletion of Potential Transport Genes

The four potential transporters identified were g2022, g2739, g8846, and g9885. The deletion constructs were built using Gibson assembly (Table 1). mfs is the known itaconic acid transporter on the membrane. For every deletion three individual transformants was picked and single spore isolated. The gene deletions were confirmed by PCR analysis. Three transformants were cultured in Riscaldati medium for 7 days. The AA in the supernatant was measured.

As shown in FIG. 3, only deletion of g8864 had a dramatic effect on reducing AA production. g8846, referred to herein as aconitic acid exporter (aexA) is annotated as a transporter and belongs to MFS family.

Example 4

Overexpression of aexA

To confirm that the g8846 gene is the transporter for AA, it was overexpressed to determine if would increase AA production. An overexpression aexA construct driven by strong promoter pgpdA was built (SEQ ID NO: 21) and transferred into *A. pseudoterreus* cadA minus background. A 7 day culture was grown for three strains, *A. pseudoterreus* with wild type cadA, cadA minus, and cadA minus with g8846/aexA overexpression from the gpdA promoter.

As shown in FIGS. 4A-C, the first column is itaconic acid production in wild type *A. pseudoterreus*, and remaining three columns are AA production in three different strains: *A. pseudoterreus* with wild type cad, cad minus or cad minus with g8846/aexA overexpression. *A. pseudoterreus* with wild type cad (cad+) produced about 35 g/L itaconic acid at day 7 (column 1), but no AA was detected (column 2). However, about 10 g/L AA was detected in *A. pseudoterreus* with a deleted endogenous cadA (Δcad, column 3). Furthermore, the combination of deleting endogenous cadA and overexpressing g8846/aexA from the gpdA promoter, dramatically increased AA production to about 35 g/L (column 4). Its titer, yield and rate are at similarly high level as itaconic acid from wild type *A. pseudoterreus*. This observed overexpression further demonstrates that g8846 is the cell plasma exporter for AA, herein named as aexA (aconitic acid exporter).

Example 5

Production of Organic Acids

To demonstrate that overexpression of aexA can be used to increase production of organic acids in different fungi, the following methods were used. An overexpression aexA construct driven by strong promoter pgpdA was built (SEQ ID NO: 21) and transferred into wild-type *A. pseudoterreus* background or *A. niger* background.

Figure 6A:
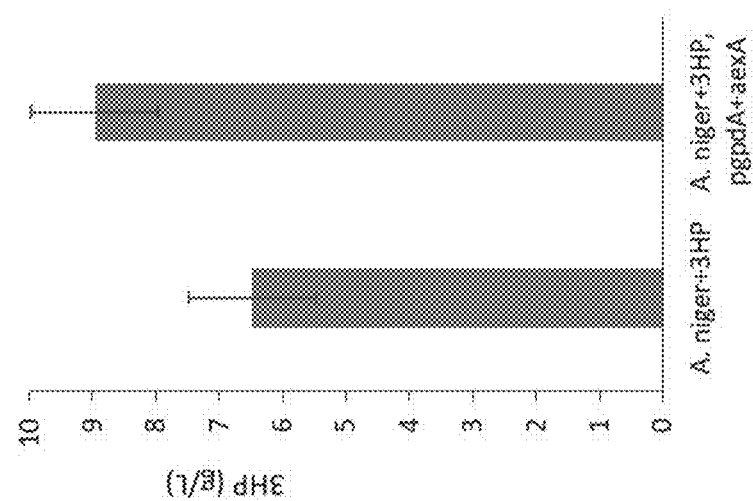
FIGS. 6A-6C are bar graphs showing the effect of aexA (g8846) overexpression using SEQ ID NO: 21 for 7 days on production of (A) itaconic acid in *A. pseudoterreus*, (B) citric acid in *A. niger*, and (C) 3-HP in engineered *A. niger* strain with 3HP pathway.

As shown in FIG. 6A, production of itaconitic acid in *A. pseudoterreus* overexpres sing aexA (g8846) did not significantly increase as compared to native *A. pseudoterreus*.

Figure 6B:
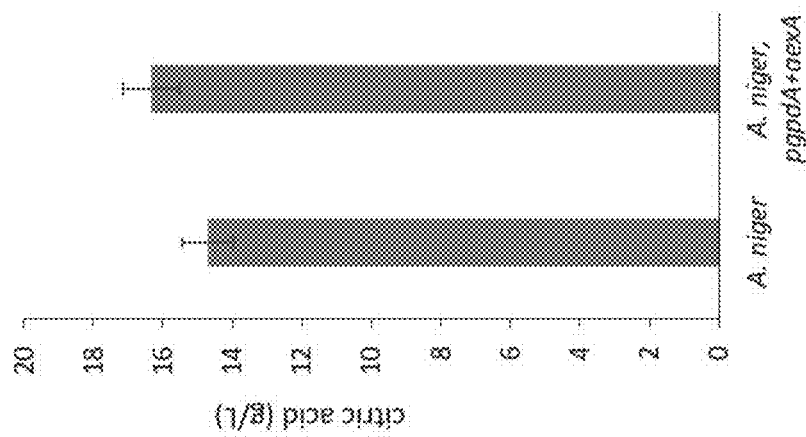

As shown in FIG. 6B, production of citric acid in *A. niger* overexpressing aexA (g8846) was increased by about 14% as compared to native *A. niger*.

Figure 6C:
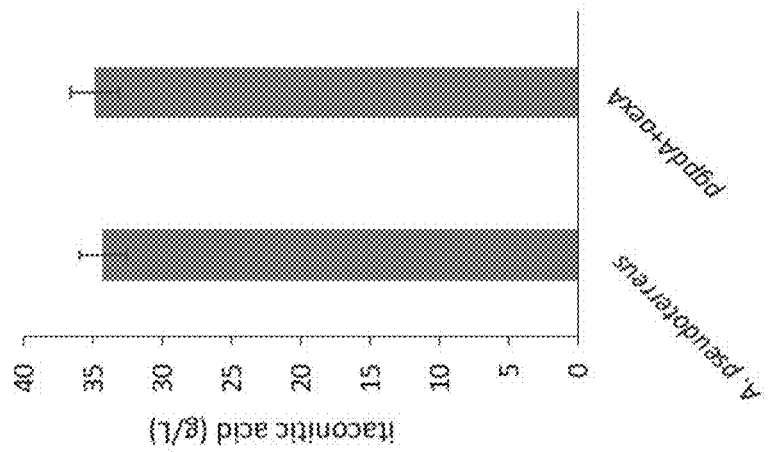

As shown in FIG. 6C, production of 3HP in *A. niger* overexpres sing aexA (g8846) and further expressing a transgene expression cassette that allowed for expression of panD, BAPAT, and HPDH (e.g., see U.S. Pat. No. 10,947, 548 and sequences provided herein), increased by about 50% as compared to native *A. niger*.

REFERENCES

Callister et al., 2006. Journal of Proteome Research 5:277-286.
Cao et al., 2011. A novel hyperbranched polyester made from aconitic acid (B3) and di(ethylene glycol) (A2). Polymer International 60:630-634.
Carroll et al., 1994. Fungal Genet. Newsl. 41:22.
Dai et al., 2013. Fungal Genetics and Biology 61:120-132.
Deng et al., 2020. Applied Microbiology and Biotechnology 104:3981-3992.
Gibson et al., 2010. Science 329:52-56.
Gibson et al., 2009. Nature Methods 6:343-345.
Gutierrez, 1978. Preparation of aconitic acid. U.S. Pat. No. 4,123,459.
Kim S, Pevzner P A. 2014. Nature Communications 5:5277.
Kim et al., 2018. Methods Mol Biol 1775:107-118.
Kobayashi et al., 2016. ChemistrySelect:1467-1471.
Kubodera et al., 2000. Bioscience, Biotechnology, and Biochemistry 64:1416-1421.
Kumar V, Raveendiran N. 2018. Synthesis, Characterisation, Biological and Molecular Docking Studies of Aconitic Acid Based Co-Polyester.
Li et al., 2011. A clone-based transcriptomics approach for the identification of genes relevant for itaconic acid production in *Aspergillus*. Fungal Genetics and Biology 48:602-611.
Matzke M M, et al. 2013. A comparative analysis of computational approaches to relative protein quantification using peptide peak intensities in label-free LC-MS proteomics experiments. 13:493-503.
Monroe et al., 2008. Computational Biology and Chemistry 32:215-217.
Nakayasu et al. 2016. mSystems 1:e00043-00016.
Riscaldati et al., 2000. Journal of Biotechnology 83:219-230.
Webb-Robertson et al., 2017. P-MartCancer—Interactive Online Software to Enable Analysis of Shotgun Cancer Proteomic Datasets. Cancer Research 77:e47-e50.
Werpy T, Petersen G. 2004. Top Value Added Chemicals from Biomass: Volume I—Results of Screening for Potential Candidates from Sugars and Synthesis Gas. Office of Scientific and Technical Information (OSTI). Report no.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. A method of producing 3-hydroxypropionic acid (3-HP), comprising: culturing an isolated recombinant *Aspergillus* fungus in Riscaldati medium, or modified Riscaldati medium under conditions that permit the fungus to produce 3-HP, thereby making 3-HP, wherein the fungus comprises:

an exogenous nucleic acid molecule encoding an aconitic acid exporter (aexA) protein comprising at least 60% sequence identity to SEQ ID NO: 2, 3, 4, or 5, operably linked to an exogenous promoter, thereby overexpressing the aexA in the fungus;

an endogenous or exogenous nucleic acid molecule encoding aspartate 1-decarboxylase (panD);

an endogenous or exogenous nucleic acid molecule encoding β-alanine-pyruvate aminotransferase (BAPAT); and an endogenous or exogenous nucleic acid molecule encoding 3-hydroxypropionate dehydrogenase (3-HPDH), and wherein the Riscaldati medium comprises 100 g/L glucose, 0.11 g/L $KH_2PO_4$, 2.36 g/L $(NH_4)_2SO_4$, 2.08 g/L $MgSO_4*7H_2O$, 0.074 g/L NaCl, 0.13 g/L $CaCl_2*2H_2O$, 0.0013 g/L $ZnSO_4*7H_2O$, 0.0055 g/L $FeSO_4*7H_2O$, 0.0002 g/L $CuSO_4*5H_2O$, and 0.0007 g/L $MnCl_2*4H_2O$, or wherein the modified Riscaldati medium comprises 100 g/L glucose, 0.11 g/L $KH_2PO_4$, 2.36 g/L $(NH_4)_2SO_4$, 2.08 g/L $MgSO_4*7H_2O$, 0.074 g/L NaCl, 0.13 g/L $CaCl_2*2H_2O$, 20 times 0.0013 g/L $ZnSO_4*7H_2O$, 20 times 0.0055 g/L $FeSO_4*7H_2O$, 20 times 0.0002 g/L $CuSO_4*5H_2O$, and 20 times 0.0007 g/L $MnCl_2*4H_2O$.

2. The method of claim 1, wherein the isolated recombinant *Aspergillus* fungus further comprises a genetically inactivated endogenous cis-aconitic acid decarboxylase (cadA) gene.

3. The method of claim 1, wherein the isolated recombinant *Aspergillus* fungus is *Aspergillus pseudoterreus* or *Aspergillus oryzae*.

4. The method of claim 1, wherein the isolated recombinant *Aspergillus* fungus is *Aspergillus niger*.

5. The method of claim 2, wherein the endogenous cadA gene is genetically inactivated by complete deletion of the cadA gene, partial deletion of the cadA gene, or by insertional mutation of the cadA gene.

6. The method of claim 2, wherein the cadA gene prior to its genetic inactivation encodes a protein having at least 80% sequence identity to SEQ ID NO: 7 or 9.

7. The method of claim 2, wherein the cadA gene prior to its genetic inactivation comprises a coding sequence having at least 80% sequence identity to SEQ ID NO: 6, 8, 10 or 11.

8. The method of claim 1, wherein the nucleic acid molecule encoding aexA comprises at least 60% sequence identity to SEQ ID NO: 1.

9. The method of claim 1, wherein the nucleic acid molecule encoding aexA encodes a protein comprising at least 90% sequence identity to SEQ ID NO: 2, 3, 4, or 5.

10. The method of claim 1, wherein the exogenous nucleic acid molecule encoding aexA operably linked to an exogenous promoter is part of a vector.

11. The method of claim 10, wherein the vector is a plasmid.

12. The method of claim 1, wherein the nucleic acid molecule encoding panD comprises:

at least 80% sequence identity to SEQ ID NO: 12 or 14, and/or encodes a panD protein comprising at least 80% sequence identity to SEQ ID NO: 13.

13. The method of claim 1, wherein the nucleic acid molecule encoding BAPAT comprises:

at least 80% sequence identity to SEQ ID NO: 15 or 17, and/or encodes a BAPAT protein comprising at least 80% sequence identity to SEQ ID NO: 16.

14. The method of claim 1, wherein the nucleic acid molecule encoding 3-HPDH comprises:

at least 80% sequence identity to SEQ ID NO: 18 or 20, and/or encodes a 3-HPDH protein comprising at least 80% sequence identity to SEQ ID NO: 19.

15. The method of claim 1, wherein the exogenous nucleic acid molecule encoding panD, the exogenous nucleic acid molecule encoding BAPAT, and the exogenous nucleic acid molecule encoding 3-HPDH are part of a single exogenous nucleic acid molecule.

16. The method of claim 1, further comprising isolating the 3-HP from culture media or from the fungus.

* * * * *

SEQUENCE LISTING

```
Sequence total quantity: 89
SEQ ID NO: 1            moltype = DNA   length = 1743
FEATURE                 Location/Qualifiers
misc_feature            1321..1322
                        note = n is a, c, g, or t
source                  1..1743
                        mol_type = genomic DNA
                        organism = Aspergillus pseudoterreus
SEQUENCE: 1
atgacgagag acgagcacga tgttacttcc tcgcggacct ccagcgacga agatgtgatc   60
tcctttggagg agcagccaac gcgcgacgac catgccaatg gagcgctaga aaagcagagc  120
acggtcgcct ccggactgtc gaggttggag agtcgcgcgc agtctgtaat ttcgcgcatc  180
cgcagccgcg agcctggtca aacgcgcgcgc tttacgcatc cgctgtcgca taccaaaacg  240
tcgcccgacg tgattgtgga ttttgacggg ccggacgatc catatcggcc tatgaactgg  300
actttcagga aaaaggccgt gacaactgtg ttgtatggct tgacaacaat gggcgccact  360
tgggcaagtt ccatgtatgt ctagccccc tctctcctac catttgcgaa ttgcgactca  420
ggtatactaa tgatgcgcag tttctcgaca ggcacgcagc aagtgagtaa acagtaccat  480
gtcggcgagg aggttggcac tctcggcacc actctacttc tactcggctt cggtaagtcg  540
ttccatcatg atgtcttcgg tgcatatgcg gactgatcac tcacatctca tcttgcgata  600
caggtctggg tcctctggtc tgggcccat tgtccgaggt atacggccgc aaaccggccg  660
tcttagcgcc ctactttatc gccgcgatat tctcgttcgg aaccgcaacc gctaaagata  720
tccaaaccat tatgatcacc cgtttcttca ccggattctt cggctcaggc ccgtcacca  780
acaccggtgg tgtgcttggc gatatctggt ccgccgaaga acggggcgcc gctatcgtcg  840
gatacgccat ggctgtcgtg ggcgggccag ttctgggccc cattgttggt ggcgccatcg  900
tacaaagcta cctgcgatgg cgatggacag aatacgtgcg taattcgaat cccccggcga  960
acacacgcca ccccggtca tcagatacta acttcgcccc ccgtacacag atcaccggca  1020
tcatgatgtt cttcttcctg ctcatggacg tcgtgttcct cgacgaaagc taccgcccg  1080
tcctcctcgt gtacaaagca cggcgcctgc gctacgacac gggcaactgg gccctgcacg  1140
cgaagcacga agaatgggac gtcaccttca aggagctcgg caacaagtac ctcatccgcc  1200
ccttcgccct cctcgccacg cccatctgct tcctcgtcgc cttgtacgcc tccttcgtct  1260
acggcatcct ctacctcagt ctggcctcct tccccgtcga gtttcaggaa gtgcgcggct  1320
nncccccgtcc ccgaggcccg cctccctccc atgatgctcg gctctgtcct cttcgccgca  1380
```

```
ggcctcttca tcttcggctg accggccgc ccggatatcc actggatcgg ccccatcatc    1440
ggcgccgtct ccatgggctt cggcttcttc acgatcttcc aggccgccct gaactatctc    1500
atcgatacct tccagaaggt cgcggccagc gctgtggccg ccaacacctt cctccgcagc    1560
gttttcgccg gtgcttccc gctgttcgcg acgatcatgt tccgcagact cggtgtcgac    1620
tgggcctcga gtgtgttggg gttcgtcgcc gtcgcgttga tcccgatccc gtacctgttc    1680
tatatcttcg gaaagcggat cagagcgaga gggaagtggt cacgcgcttc tgtttacggc    1740
tac                                                                  1743

SEQ ID NO: 2             moltype = AA    length = 513
FEATURE                  Location/Qualifiers
source                   1..513
                         mol_type = protein
                         organism = Aspergillus pseudoterreus
SEQUENCE: 2
MTRDEHDVTS SRTSSDEDVI SLEEQPTRDD HANGALEKQS TVASGLSRLE SRAQSVISRI     60
RSREPGQTAR FTHPLSHTKT SPDVIVDFDG PDDPYRPMNW TFRKKAVTTV LYGLTTMGAT    120
WASSIFSTGT QQVSKQYHVG EEVGTLGTTL LLLGFGLGPL VWAPLSEVYG RKPAVLAPYF    180
IAAIFSFGTA TAKDIQTIMI TRFFTGFFGS APVTNTGGVL GDIWSAEERG AAIVGYAMAV    240
VGGPVLGPIV GGAIVQSYLR WRWTEYVRNS NPPANTRHPR SSDTNFAPRT QITGIMMFFF    300
LLMDVVFLDE SYPPVLLVYK ARRLRYDTGN WALHAKHEEW DVTFKELGNK YLIRPFALLA    360
TPICFLVALK CAAXPVPEAR LPPMMLGSVL FAAGLFIFGW TGRPDIHWIG PIIGAVSMGF    420
GFFTIFQAAL NYLIDTFQKV AASAVAANTF LRSVFAGCFP LFATIMFRRL GVDWASSVLG    480
FVAVALIPIP YLFYIFGKRI RARGKWSRAS VYG                                 513

SEQ ID NO: 3             moltype = AA    length = 575
FEATURE                  Location/Qualifiers
source                   1..575
                         mol_type = protein
                         organism = Aspergillus terreus
SEQUENCE: 3
MTRDEHDVTS SRTSSDEDVI SLEEQPTRDD HANGALEKQS TVASGLSRLE SRAQSVISRI     60
RSREPGQTAR FTHPLSHTKT SPDVIVDFDG PDDPYRPMNW TFRKKAVTTV LYGLTTMGAT    120
WASSIFSTGT QQVSKQYHVG EEVGTLGTTL LLLGFGLGPL VWAPLSEVYG RKPAVLAPYF    180
IAAIFSFGTA TAKDIQTIMI TRFFTGFFGS APVTNTGGVL GDIWSAEERG AAIVGYAMAV    240
VGGPVLGPIV GGAIVQSYLR WRWTEYVRNS NPPANTRHPR SSDTNFAPRT QITGIMMFFF    300
LLMDVVFLDE SYPPVLLVYK ARRLRYDTGN WALHAKHEEW DVTFKELGNK YLIRPFALLA    360
TPICFLVALY ASFVYGILYL SLASFPVEFQ EVRGWNPVVG ALPFLAYLVG ILFGACVNLF    420
NQRFYIKRFK ANNNFPVPEA RLPPMMLGSV LFAAGLFIFG WTGRPDIHWI GPIIGAVSMG    480
FGFFTIFQAA LNYLIDTFQK VAASAVAANT FLRSVFAGCF PLFATIMFRR LGVDWASSVL    540
GFVAVALIPI PYLFYIFGKR IRARGKWSRA SVYGY                               575

SEQ ID NO: 4             moltype = AA    length = 1198
FEATURE                  Location/Qualifiers
source                   1..1198
                         mol_type = protein
                         organism = Aspergillus arachidicola
SEQUENCE: 4
MLKVGSWLYG KKAGANASTQ SLDSLVELRD LEDAMRAATL ILNDDVDGAE DGLSEGVSSF     60
HNLGRGVVAF IRATLGFEQE IMRQASERLN TAETSAASDQ NKAQHNSHAP NTYHSPIYSP    120
GTEFALCQAM AQLMSAVVGV LNESLTESIK GFYKMRKAYI TLDGILKMEQ AYMRSISGGV    180
SPADQGEASK PSPTATVEAK GLSQRLSDLS VSQDSTKSGE STEPSTPNPS DMLSHDPSD     240
IFKNQIDVFV HSGSNFCGI LLLVISMVPP AFSKLLSIIG FYGDKERGLR MLWQASKFNN    300
LIGALAAFAI LGYYNGFVRY CDIMPDPVPG DQGVQGYPQ KRLEALLAQM RQRFPKSQLW    360
LLEESRMEGA NKNLERSLEL LCGEERSPLK QVEALRVFER SLNAMYLHKY ELCAEAFLEC    420
VELNSWSRSL YYYIAGASHL SLYRSTIVTD PKKAEEHAEK ATEYFRTAPT FAGKKRFMAR    480
QLPFDVFVAR KIAKWEARAK EWGVPLVEAV GVDPIEEMIF FWNGHSRMTQ AQLDESMQKL    540
AWSESDENKK WSREGPEEKA ILQLLRAAVL RAMRKHDEAR QLLKESVLNH DKSLFTGHLK    600
DNWIHPVAHF EMAANLWMER PGYIAVHDAP ATEGKIANGE EVTQLERQQV RECKEYLEKA    660
ARWESYELDA RIGLKVTAAM EAVRKDEERS SSHSSLDDDG NSLELRHTTY DERPNATLEK    720
QSTAASALSV FEQRAQSVVS RIRSREPGQT ARFTHPLTHT KTSTDVIVDF DGPDDPYRPL    780
NWSFRKKAIT TLLYGLTTMG ATWASSIYST GTRQVDAEFG VGEEVGTLGT ALLLFGFGLG    840
PLVWAPLSEV YGRKPAVLAP YFIAAIFSFG TATAKDLQTV MITRFFTGFF GSAPVTNTGG    900
VLSDIWTAEQ RGAAIVGYAM AVVGGPVLGP IVGGAIVQSY LGWRWTEYLT GIMMMFFLAM    960
DVLFLDESYP PVLLVYKAQR LRFESGNWAL HARHEEWDVT FKELGNKYLI RPFQLLTTPI   1020
CFLVALYASF VYGIIYLSLA AFPVEFQEVR GWNQVVGALP FLGPPSPMML GSVFFAAGMF   1080
VFGWTGQPDI HWIGPVIGAV MMGFGFFTIF QAALNYLIDT FQKVSASAVA ANTFLRSVFA   1140
GCFPLFASIM FRKLGVPWAS SVLGFVSVAL IPIPYLFYIF GKRIRAAGKW SRASVYGD    1198

SEQ ID NO: 5             moltype = AA    length = 555
FEATURE                  Location/Qualifiers
source                   1..555
                         mol_type = protein
                         organism = Aspergillus avenaceus
SEQUENCE: 5
MTRDDADVHS TSLSSFDDDT NSLDERPTQH EGPNGALEK QSTAASGLSV FEQRAQSVVS      60
RIRSREPGQT ARFTHPLSHT KTTEDAIVDF DGPDDPYRPM NWGFKKKAMT TVLYGLTTMG    120
ATWSSSIYST GTKQIDSEFG VGEEVGTLGT ALLLFGFGLG PLIWAPLSEV YGRKPAVLAP    180
YFIAAIFSFG TATAKDLQTV MLTRFFTGFF GSAPVTNTGG VLSDIWTAEQ RGAAIVGYAM    240
AVVGGPVLGP IVGGAIVQSY LRWRWTEYIT GIMMMFFLTM DLLFLDESYP PVLLVYKARR    300
```

```
LRFNTGNWAL HARHEEWDVT LKELGNKYLI RPFQLLTTPI CFLVALYASF VYGILYLSLA  360
AFPVEFQEIR GWNPVIGALP FLAYLVGILF GACINLLNQK FYIKRFKANN NFPVPEARLP  420
PMMLGSILFA AGLFVFGWTG KPSIHWIGPI IGAVMMGFGF FTIFQAALNY LIDTFQSVSA  480
SAVAANTFLR SVFAGTFPLF ASIMFRRLGV NWAASILGFV AIALIPIPYL FYVFGKRIRA  540
RGKWSRASVY GDCGN                                                  555

SEQ ID NO: 6           moltype = DNA    length = 2206
FEATURE                Location/Qualifiers
source                 1..2206
                       mol_type = genomic DNA
                       organism = Aspergillus terreus
SEQUENCE: 6
gtgggtcttg aaatcgtatg ccacacttgc tccggatgaa acacattccg gagcgcgcat   60
cgatattgct acacagtata gacccaatgg tctgcagatg ccctaaatgg tagttctcac  120
tggcctgcat taagttctgg ttgcagatca ttgtcggcct aacatcagtg taggttacgg  180
tgtgagattt acttgcatag aagattccag accacaaggt tctagatcct ttgacggcgg  240
actcccctcg aggtgccggg cgccgacgtg tgcgttgctc cgggatttgt aggacgcagc  300
tcggataccct agccgttatg ggaatcggag gttgtagcga cgtaaacaca tggatagtta  360
aataatcgga tgtacaccca ctgttggaaa tgacggggc ctacaacacg agattatctg   420
atccaatttc tgttcgttgg cattctatca ttcgcagcga aaattgtcct attaaattga   480
ccatgaccaa acaatctgcg gacagcaacg caaagtcagg agttacgtcc gaaatatgtc   540
attgggcatc caacctggcc actgacgaca tcccttcgga cgtattagaa agagcaaaat   600
accttattct cgacggtatt gcatgtgcct gggttggtgc aagagtgcct tggtcagaga   660
agtatgttca ggcaacgatg agctttgagc cgccgggggc ctgcagggtg attggatatg   720
gacaggtaaa tttttattcac tctagacggt ccacaaagta tactgacgat ccttcgtata   780
gaaactgggg cctgttgcag cagccatgac caattccgct ttcatacagg ctacggagct   840
tgacgactac cacagcgaag ccccctaca ctctgcaagc attgtccttc ctgcggtctt    900
tgcagcaagt gaggtcttag ccgagcaggg caaaacaatt tccggtatag atgttattct   960
agccgccatt gtgggtttg aatctggccc acggatcggc aaagcaatct acggatcgga   1020
cctcttgaac aacggctggc attgtggagc tgtgtatggc gctccagcg gtgcgctggc   1080
cacaggaaag ctcctcggtc taactccaga ctccatggaa gatgctccg gaattgcgtg    1140
cacgcaagcc tgtggtttaa tgtcggcgca atacggaggc atggtaaagc gtgtgcaaca   1200
cggattcgca gcgcgtaatg tgcttcttgg gggactgttg gcccatggtg ggtacgaggc   1260
aatgaaaggt gtcctggaga gatcttacgg cggtttcctc aaagatgttca ccaagggcaa  1320
cggcagagag cctccctaca aagaggaga agtggtggct ggtctcggtt cattctggca    1380
taccttttact attcgcatca agctctatgc ctgctgcgga cttgtccatg tccagtcgga   1440
ggctatcgaa aaccttcagg ggagataccc cgagctcttg aatagagcca acctcagcaa   1500
cattcgccat gttcatgtac agcttcaac ggcctcgaac agtcactgtg gatggatacc    1560
agaggagaga cccatcagtt caatgcagg gcagatgagt gtcgcataca ttctcgccgt    1620
ccagctggtc gaccagcaat gtctttgtc ccagtttct gagtttgatg acaacctgga    1680
gaggccagaa gtttgggatc tggccaggaa ggttacttca tctcaaagcg aagagtttga   1740
tcaagacggc aactgtctca gtgcgggtcg cgtgaggatt gagttcaacg atggttcttc   1800
tattacggaa agtgtcgaga agcctcttgg tgtcaaagag cccatgccaa acgaacgat    1860
tctccacaaa taccgaaccc ttgctggtag cgtgacggac gaatcccggg tgaaagagat   1920
tgaggatctt gtcctcggcc tggacaggct caccgacatt agcccattgc tggagctgct   1980
gaattgcccc gtgaaatcgc cactggtata aatgggaagc gatatggaaa catttcatgt   2040
cacgggcaca aattctaggt catatcgtac ctggatggtg aaaccaccag cggtttagca   2100
gatagaagat agactccttc tgctctgcgt tgcgtcttga atttagttcg ttcactggct   2160
taagaactta gaatgcaata cagtctctct tatttcttat taaaat                 2206

SEQ ID NO: 7           moltype = AA    length = 490
FEATURE                Location/Qualifiers
source                 1..490
                       mol_type = protein
                       organism = Aspergillus terreus
SEQUENCE: 7
MTKQSADSNA KSGVTSEICH WASNLATDDI PSDVLERAKY LILDGIACAW VGARVPWSEK   60
YVVQATMSFEP PGACRVIGYG QKLGPVAAAM TNSAFIQATE LDDYHSEAPL HSASIVLPAV  120
FAASEVLAEQ GKTISGIDVI LAAIVGFESG PRIGKAIYGS DLLNNGWHCG AVYGAPAGAL   180
ATGKLLGLTP DSMEDALGIA CTQACGLMSA QYGGMVKRVQ HGFAARNGLL GGLLAHGGYE   240
AMKGVLERSY GGFLKMFTKG NGREPPYKEE EVVAGLGSFW HTFTIRIKLY ACCGLVHGPV   300
EAIENLQGRY PELLNRANLS NIRHVHVQLS TASNSHCGWI PEERPISSIA GQMSVAYILA   360
VQLVDQQCLL SQFSEFDDNL ERPEVWDLAR KVTSSQSEEF DQDGNCLSAG RVRIEFNDGS   420
SITESVEKPL GVKEPMPNER ILHKYRTLAG SVTDESRVKE IEDLVLGLDR LTDISPLLEL   480
LNCPVKSPLV                                                         490

SEQ ID NO: 8           moltype = DNA    length = 1862
FEATURE                Location/Qualifiers
source                 1..1862
                       mol_type = genomic DNA
                       organism = Aspergillus vadensis
SEQUENCE: 8
gttttctgtg tgtcttggg gggttataaa tagggtgtcg aatatctgga agatagggaa    60
ttccttctct ttcaatcaat caatcaagaa ttcttttagg gagtttctat actacatccg   120
atatggtcgc catcaccgct aaatctgaag cggcttctgc tacttcgccc attcctacca   180
attctaatac taccatgact actaccctca acggggtaga tggttcaaaa gagaaagaaa   240
aagaccagat accccaaac aaagaggaag gaacaaaagc agaagagaaa gaaaccgaag   300
catacaactc ctccaacggc gtcaccagcc aactctgcaa ctggatcgcc tctctccagc   360
tagaagacat tccagactct gtccgcaccc gcgccaagta ccctcttttctc gatggcatcg   420
```

```
                                                -continued
cctgcgcact cgtcggtgcg cgcgtcccat ggtcgcagaa ggcttttgat gcgatggctg    480
ttttcgagga gaagggaaag catgtggtta ttgggtatga agagcgcctt ggtgctatcg    540
ccgccgcaac cctcaacggc tcctggatcc aagcctgcga agtagacgac taccacagcg    600
tggcgcccct gcactcgcag gccgtggtca tccctcctct cttcgctgcc gccgtcagtg    660
cgccgaacca tccgaccgca ccgcgcatca tcgacgggcg aacacttctt ctccgcctcc    720
tggtagggtt cgaggttggt ccgcgcgtgg gcatggcgct acacggcacc gagatgctcg    780
cgaagggatg gcactgcggg tctgtgtttg gtggacccgc ggccgcaggc agttctgcaa    840
aactactcgt tttgtcggcg ggtcaagtcg aagacgcgat cggagtagca gcgacacaag    900
catgcggact catggcggcg cagtacgacg ggatggtgaa gcgatgcat catggcttcg    960
cggcaaggaa tggactgttg ggcacgatgt tagcgtgggg aggttatgaa gggatcaaga    1020
aggtgtttga gcggccgtat ggaggatttc tggcaatgtt tggcctaggg tcgaagcaca    1080
cgcctagttc gaagccggag gaggtggcaa aggatttggg gacgttctgg cacacggcg    1140
agtggattcg gttgaagttg catgcgtgct gtgggggat tcatggcacg attgagtgtt    1200
tggcgggagat gcaggagatg tatccagagc gatttggacg ggagaaacta ggagagatca    1260
aggagattcg gatccagttg agtgatgcgg tgtttcatca ttgtggatgg gcgccggaga    1320
cgaggccgtt gaccccgacg ggggcgcaga tgaatacggc gtttgtggcg gcctcgcagt    1380
tggtggatgg acaagtgttg ttggagcagt tctcgtcggg gaagttggat cgggatgagg    1440
tttgggaatt gattgggaag acgagttgta ttccatacgg cggatttggac aagccgaata    1500
ttggttgtgg tgcgttgatc tccatcacgt ttgcggatgg cagtcaggtt cagcattcgt    1560
tgttgaagcc gaaggggtg gatgaaccca tttgaatga ggagatcttg gagaagtttc    1620
gtcggttgac gggcggggttg attggggtgg agagcagga gaagattgaa aaggccgtgc    1680
tggggatgga ggagttgcag gatgtggatg agttgattga ttgctgagt gtgaatgtga    1740
tcaatccgtt gcagtagtat actagtcatc tgtttgatg cttctggcgt tggtcgtgtt    1800
gggatagtat ctcataattt tgaattaata aatcattcaa catggtgaaa atcatatttg    1860
tg                                                                  1862

SEQ ID NO: 9          moltype = AA length = 544
FEATURE               Location/Qualifiers
source                1..544
                      mol_type = protein
                      organism = Aspergillus vadensis
SEQUENCE: 9
MVAITAKSEA ASATSPIPTN SNTTMTTTLN GVDGSKEKEK DQIPPNKEEG TKAEEKETEA     60
YNSSNGVTSQ LCNWIASLQL EDIPDSVRTR AKYLFLDGIA CALVGARVPW SQKAFDAMAV    120
FEEKGKHVVI GYEERLGAIA AATLNGSWIQ ACEVDDYHSV APLHSQAVVI PPLFAAAVSA    180
RNHPTAPRII DGRTLLLASV VGFEVGPRVG MALHGTEMLA KGWHCGSVFG GPAAAGSSAK    240
LLGLSAGQVE DAIGVAATQA CGLMAAQYDG MVKRMHHGFA ARNGLLGTML AWGGYEGIKK    300
VFERPYGGFL AMFGLGSKHT PSSKPEEVAK DLGTFWHTAE WIRLKLHACC GGIHGTIECL    360
AEMQEMYPER FGREKLGEIK EIRIQLSDAV FHHCGWAPET RPLTPTGAQM NTAFVAASQL    420
VDGQVLLEQF SSGKLDRDEV WELIGKTSCI HTAELDKPNI GCGALISITF ADGSQVQHSL    480
LKPKGVDEPI SNEEILEKFR RLTGGLIGVE RQEKIEKAVL GMEELQDVDE LIELLSVNVV    540
NPLQ                                                                544

SEQ ID NO: 10         moltype = DNA length = 987
FEATURE               Location/Qualifiers
source                1..987
                      mol_type = genomic DNA
                      organism = Aspergillus pseudoterreus
SEQUENCE: 10
ggttgtagca gcgtaaacac atggatagtt aaataatcgg atgtacaccc actgttggaa     60
atgacgggg cctacaacac gagattatct gatccaattt ctgttcgttg gcattctatc    120
attcgcagcg aaaattgtcc tattaaattg accatgacca aacaatctgc ggacagcaac    180
gcaaagtcag gagttacgtc cgaaatatgt cattgggcat ccaacctggc cactgacgac    240
atcccttcgg acgtattaga aagagcaaaa taccttattc tcgacgggat tgcatgtgcc    300
tgggttggtg caagagtgcc ttggtcagag aagtatgttc aggcaacgat gagctttgaa    360
ccgccggggg cctgcagggt gattggatat ggacaggtaa atttattca ctctagacgg    420
tccacaaagt atactgacga tccttcgtat agaaactggg gcctgttgca gcagccatga    480
ccaattccgc tttcatacag gctacggagc ttgacgacta ccacagcgaa gcccccctac    540
actctgcaag cattgtcctt cctgcggtct ttgcagcaag tgaggtctta gccgagcagg    600
gcaaaacaat ttccggtata gatgttattc tagccgccat tgtgggtttt gaatctggcc    660
cacggatcgg caaagcaatc tacgatcggg acctcttgaa caacggctgg cattgtggag    720
ctgtgtatgg cgctccagcc ggtgcgctgg ccacaggaaa gctcctcggt ctaactccag    780
actccatgga agatgctctc ggaattgcgt gcacgcaagc ctgtggttta atgtcggcgc    840
aatacggagg catggtaaag cgtgtgcaac acgattcgc agcgcgtaat ggtcttcttg    900
ggggactgtt ggcccatggt gggtacgagg caatgaaagg tgtcctggag atcttacg    960
gcggtttcct caagatgttc accaagg                                        987

SEQ ID NO: 11         moltype = DNA length = 908
FEATURE               Location/Qualifiers
source                1..908
                      mol_type = genomic DNA
                      organism = Aspergillus pseudoterreus
SEQUENCE: 11
ctcagcaaca ttcgccatgt tcatgtacag ctttcaacgg cctgaacag tcactgtgga     60
tggataccag aggagagacc catcagttca atcgcagggc agatgagtgt cgcatacatt    120
ctcgccgtcc agctggtcga ccagcaatgt ctttttgtcc agttttctga gtttgatgac    180
aacctgggaga ggcagaagt ttgggatctg ccaggaagg ttacttcatc tcaaagcgaa    240
gagtttgatc aagacggcaa ctgtctcagt gcgggtcgcg tgaggattga gttcaacgat    300
ggttcttcta ttacggaaag tgtcgagaag cctcttggtg tcaaagagcc catgccaaac    360
```

```
gaacggattc tccacaaata ccgaacccct gctggtagcg tgacggacga atcccgggtg      420
aaagagattg aggatcttgt cctcggcctg gacaggctca ccgacattag cccattgctg      480
gagctgctga attgcccgt gaaatcgcca ctggtataaa tgggaagcga tatgaaaca       540
tttcatgtca cgggcacaaa ttctaggtca tatcgtacct ggatggtgaa accaccagcg      600
gtttagcaga tagaagatag actccttctg ctctgtgttg cgtcttgaat ttagttcgtt      660
cactggctta agaacttaga atgcaataca gtctctctta tttcttatta aaatcacgta      720
ttcccacatt cggcgactgg aggatacgaa agcagtgttg gtggtgctcc ccgtaatgga      780
tatgattttg ctgactggac tattctatga ccattccctc caacggagat cctttctcga      840
cactttagat gttgacgctg tctggaggaa ctactttgc gctgcaaaga ctatgagcag       900
tggagctg                                                               908

SEQ ID NO: 12          moltype = DNA   length = 1797
FEATURE                Location/Qualifiers
source                 1..1797
                       mol_type = genomic DNA
                       organism = Tribolium castaneum
CDS                    41..1663
SEQUENCE: 12
acttgtgaat cagtcgtgcc cccacgagga tccacacacg atgccggcca caggcgaaga       60
ccaagacctg gtcaagacc tcatcgagga gcccgccacc ttcagcgacg ccgtcctctc      120
ctccgacgag gaactcttcc accagaagtg ccccaaaccc gcccccattt actcccggt      180
ctcgaaaccg gtctccttcg agagcctccc caacaggccg ctccacgagg agttcctccg      240
cagctcggtg gacgtcctcc tccaggagcc ggtgttcgag ggaacgaacc gcaagaaccg      300
ggtgctgcaa tggcgggagc cggaggagtt gaggcgtctg atggactttg gggtgcggag      360
tgcgccctcc acgcacgagg agttgttgga ggtgttgaag aaggttgtaa cttattcggt      420
taaaaccgga catccgtact tcgtgaacca gttgttctcg gcggtggatc cgtacggttt      480
ggtggcacaa tgggccacgg atgcgctcaa tccgagtgtt tacacctacg aggttttcgcc      540
ggttttttgtt ctgatggagg aagtggtttt gagggagatg agggccattg tggggttcga      600
ggggggaaag ggcgatggga ttttttgccc aggagggtcc attgccaatg gatatgccat      660
cagttgtgcc agatacaggt ttatgcccga tattaagaaa aaaggcctcc actctctccg      720
ccgtttggtc ctcttcacct ctgaagatgc ccactattcc atcaaaaaac tcgcctcttt      780
ccaaggcatc ggcaccgaca acgtctactt gatacgaacg gacgcccgag gtcgcatgga      840
cgtctcgcac ctggtggagg aaatcgagcg ttcgctccgt gaaggcgccg ctcctttcat      900
ggtcagtgcc accgctgaa ccacagtgat tggtgccttt gacccgatcg aaaaaatcgc      960
agatgtgtgc caaaaatacaactggtt gcacgtggat gccgctggg gaggtggccg       1020
gcttgtctct gccaaacacc gccacctcct caaagggatt gagagggccg actcggtcac      1080
ctggaaccct cacaaactcc taacagcccc ccagcaatgt tccacacttt tactgcgaca      1140
tgagggtgtc ctcgccgagg cgcattccac gaacgccgct tacctcttcc aaaaagacaa      1200
attctacgac accaaaatcg acacgggcga caagcacatc cagtgcggcc cagggccga       1260
cgtcctcaag ttctggttca tgtggaaggc gaagggaaca tcaggggttgg agaaacacgt      1320
cgataaagtg ttcgaaaatg cgagattttt cacggattgt ataaaaaatc gggaagggtt      1380
tgaaatggtg atagcggagc ccgaatacac aaacatctgc ttttggtacg tgccaagaag      1440
tctgagggg cgcaaggacg aagcggatta caaagacaag ctgcataagg tggccccag        1500
gattaaggag aggatgatga aggagggctc catgatggtc acgtaccagg cgcaaaaggg      1560
acacccgaat ttttttcagga ttgtgttcca gaattcgggg cttgacaagg ctgatatggt      1620
gcaccttgtt gaggagattg agcggttggg gagcgatctt taaggccttg aatggtgcta      1680
gttgtagatt gtgtaattaa tgtaaaaagt attatttaaa aaatgtaaat tttgatgtat      1740
ttattctcat tagttgtagt ttattcaaat aaaagtttaaa aaaaaaaaa aaaaaaa        1797

SEQ ID NO: 13          moltype = AA    length = 540
FEATURE                Location/Qualifiers
source                 1..540
                       mol_type = protein
                       organism = Tribolium castaneum
SEQUENCE: 13
MPATGEDQDL VQDLIEEPAT FSDAVLSSDE ELFHQKCPKP APIYSPVSKP VSFESLPNRR       60
LHEEFLRSSV DVLLQEAVFE GTNRKNRVLQ WREPEELRRL MDFGVRSAPS THEELLEVLK      120
KVVTYSVKTG HPYFVNQLFS AVDPYGLVAQ WATDALNPSV YTYEVSPVFV LMEEVVREM      180
RAIVGFEGGK GDGIFCPGGS IANGYAISCA RYRFMPDIKK KGLHSLPRLV LFTSEDAHYS      240
IKKLASFQGI GTDNVYLIRT DARGRMDVSH LVEEIERSLR EGAAPFMVSA TAGTTVIGAF      300
DPIEKIADVC QKYKLWLHVD AAWGGGALVS AKHRHLLKGI ERADSVTWNP HKLLTAPQQC      360
STLLLRHEGV LAEAHSTNAA YLFQKDKFYD TKYDTGDKHI QCGRRADVLK FWFMWKAKGT      420
SGLEKHVDKV FENARFFTDC IKNREGFEMV IAEPEYTNIC FWYVPKSLRG RKDEADYKDK      480
LHKVAPRIKE RMMKEGSMMV TYQAQKGHPN FFRIVFQNSG LDKADMVHLV EEIERLGSDL      540

SEQ ID NO: 14          moltype = DNA   length = 1617
FEATURE                Location/Qualifiers
misc_feature           1..1617
                       note = Synthetic nucleic acid
source                 1..1617
                       mol_type = other DNA
                       organism = synthetic construct
SEQUENCE: 14
cccgccaccg gcgaggacca ggacctggtg caggacctga tcgaggaacc cgccaccttc       60
tccgacgccg tcctgtcctc cgacgaggaa ctgttccacc agaagtgccc caagccggct      120
ccgatctaca gccccgtcag caagcccgtc agcttcgagt ccctgccgaa ccgccgcctg      180
cacgaagagt tcctccgctc ctccgtcgac gtcctgctgc aagaggccgt gttcgaggc       240
accaaccgca gaaccgcgt cctgcagtgg cgcgagcccg aagaactgcg ccgcctgatg      300
gacttcggcg tccgcagcgc cccgtccacg catgaggaac tgctcgaggt cctgaagaag      360
```

```
gtcgtcacct actccgtcaa gaccggccat ccgtacttcg tcaaccagct gttctccgcc  420
gtcgatccct acggcctggt cgcccagtgg gccaccgacg cgctgaaccc ctccgtctac  480
acctacgagg tcagccccgt gttcgtcctg atggaagagg tcgtcctgcg cgagatgcgc  540
gccatcgtcg gcttcgaagg cggcaaaggc gacggcatct tctgccctgg cggctcgatc  600
gccaacggct acgccatcag ctgcgcccgc taccgcttca tgcccgacat caagaagaag  660
ggcctgcact ccctgccgcg cctggtcctg ttcacctccg aggacgccca ctactcgatc  720
aagaagctgg cctcgttcca aggcatcggc accgacaacg tctacctgat ccgcaccgac  780
gctcgcggtc gcatggacgt cagccacctg gtcgaagaga tcgagcgctc cctccgcgag  840
ggcgctgccc cgttcatggt cagcgccacc gccggcacca ccgtcatcgg cgccttcgat  900
cccatcgaga agatcgccga cgtctgccag aagtacaagc tctggctgca cgtcgacgcc  960
gcctggggcg gaggcgctct ggtgtccgcc aagcaccgcc atctgctgaa gggcatcgag  1020
cgcgccgact ccgtcacctg gaatccccac aagctgctga ccgctccgca gcagtgcagc  1080
accctgctgc tgcgccacga gggcgtcctg gccgaggcgc actccaccaa cgccgcctac  1140
ctgttccaga aggacaagtt ctacgacacc aagtacgaca ccggcgacaa gcacatccag  1200
tgcggccgtc gcgccgacgt gctgaagttc tggttcatgt ggaaggccaa gggcacctcc  1260
ggcctcgaga agcacgtgga caaggtgttc gagaacgccc gcttcttcac cgactgcatc  1320
aagaaccgtg agggcttcga gatggtgatc gccgagcctg agtacaccaa catctgtttc  1380
tggtacgtcc ccaagagcct gcgcggacgc aaggacgagg ccgactacaa ggacaagctg  1440
cacaaggtcg cccctcgcat caaagaacgc atgatgaagg aaggctccat gatggtcacc  1500
taccaggcgc agaagggcca tccgaatttc ttccgcatcg tctttcagaa ctccggcctg  1560
gacaaggccg acatggtcca tctggtcgag gaaatcgaac gcctgggctc cgacctc     1617

SEQ ID NO: 15          moltype = DNA  length = 1356
FEATURE                Location/Qualifiers
source                 1..1356
                       mol_type = genomic DNA
                       organism = Bacillus cereus
SEQUENCE: 15
ttaaagttga gctaaacatt ctttcattgt tttaacgata aaagtaaagt cttcctctgt  60
gatgcttaat ggaggtgcaa gctgcaaaat attattgtaa cctgcaacag tgtcaccatt  120
tttaccaata attagacctt tttctttaca agcattgatg actttgttca tcttttcaat  180
ggaagccggt tcttttgttt gcttatcttc cactagttca atacctaaaa gaaggccttt  240
tccgcgaaca tctcctacgt ttggatgctc ttttacatct tctagttcat ataacagtcg  300
ttcacccaat tctttggaac gttcaatgag tttctcattc tccataattt ctaaattctt  360
caaagctaag gcgcaagcag caggatttcc tccaaacgta tttacatggc ggaagcgatc  420
ataatcatca ctgcctacga atgcctcata aacctctcgt ctaactgctg ttgctgacaa  480
aggaagatac gcacttgtaa taccttttgc cattgtaatg atatctggtt tgacgccata  540
attcataaat ccaaacggct tccctgttcg tccaaatcca catataactt catcacaaat  600
gagcaacgca ccatgcttct cgcaaatttc ttttactttt tccatatatc catcaggagg  660
cattaaaatt ccgcccccag taatgatttgg ctccataatc acaccggcta ctgtttggct  720
taactcccat gtcatgacac gatcgatttc ctcagcactt gccagtgtat gaacatcctc  780
tggattgcga tacgtatcag gcggtgctac atgcaaaaaa ccttgtccta atggctcata  840
tttatacttt ctttgtgctt gccctgttgc tgcaagagca cccattgagt taccgtgata  900
agcgcggtag cgggaaataa acttatagcg tccatgatca cctttttgct gatgatattg  960
acgagcaatt ttaaatgctg tttcatttgc ttctgatcca ctgttagaaa agaaaatgac  1020
gtattcatca tccagccatt cattcaattt ctctgctaat ttaatggcag gaacatgact  1080
ttgtgtcaga gggaaatatg gcatttcttc aagttgctca aatgccgctc ttgcaagctc  1140
ttttcggccg tatccaacat tcacacacca aagaccagac ataccgtcta aataacggtt  1200
tccatcaata tccgtcaccc atgccccttc tgcttttgtg ataattaaat tcgttggact  1260
aggggccgct cctctcatcg catgccaaag gtacttttca tctgtttttt tcaaactttg  1320
tgtttgctct gtcacttgca caatcatcag ctccat                            1356

SEQ ID NO: 16          moltype = AA  length = 451
FEATURE                Location/Qualifiers
source                 1..451
                       mol_type = protein
                       organism = Bacillus cereus
SEQUENCE: 16
MELMIVQVTE QTQSLKKTDE KYLWHAMRGA APSPTNLIIT KAEGAWVTDI DGNRYLDGMS  60
GLWCVNVGYG RKELARAAFE QLEEMPYFPL TQSHVPAIKL AEKLNEWLDD EYVIFFSNSG  120
SEANETAFKI ARQYHQQKGD HGRYKFISRY RAYHGNSMGA LAATGQAQRK YKYEPLGQGF  180
LHVAPPDTYR NPEDVHTLAS AEEIDRVMTW ELSQTVAGVI MEPIITGGGI LMPPDGYMEK  240
VKEICEKHGA LLICDEVICG FGRTGKPFGF MNYGVKPDII TMAKGITSAY LPLSATAVRR  300
EVYEAFVGSD DYDRFRHVNT FGGNPAACAL ALKNLEIMEN EKLIERSKEL GERLLYELED  360
VKEHPNVGDV RGKGLLLGIE LVEDKQTKEP ASIEKMNKVI NACKEKGLII GKNGDTVAGY  420
NNILQLAPPL SITEEDFTFI VKTMKECLAQ L                                 451

SEQ ID NO: 17          moltype = DNA  length = 1350
FEATURE                Location/Qualifiers
misc_feature           1..1350
                       note = Synthetic nucleic acid
source                 1..1350
                       mol_type = other DNA
                       organism = synthetic construct
SEQUENCE: 17
gagctgggcc agacattcct tcatagtctt gacgatgaag gtgaagtcct cttcggtgat  60
ggacagcgga ggggcgagct gcaggatgtt gttgtagccg gccacggtgt cgccgttctt  120
gccgatgatc agacccttct ctttgcaggc gttgatgacc ttgttcatct tttcgatgga  180
ggcgggctct ttggtctgct tatcctcgac gagttcgata cccagcagga ggcccttgcc  240
```

```
gcggacgtcc ccgacgttgg ggtgctcttt gacgtcctcc aactcgtaca gcaggcgctc      300
gcccagttct ttggaccgct cgatgagctt ctcgttttcc atgatctcga ggttcttcag      360
ggccagcgcg caggcggcag ggttgccgcc gaaggtgttg acatggcgga agcggtcgta      420
gtcgtcggag ccgacgaagg cctcgtagac ctcgcggcgg accgcggtgg cagacagcgg      480
caggtcggcc gaggtgatac cctttggcca ggtgataatg tcgggcttga cgccgtagtt      540
catgaagccg aagggcttgc cggtgcgacc gaagccgcag atgacctcgt cgcagatcag      600
cagggcgccg tgcttttcgc agatctcttt gaccttttcc atgtagccgt ccggcggcat      660
caggatgcca ccaccggtga tgatgggttc catgatgacg ccggcgacgg tctgggacag      720
ctcccaggtc atgacgcggt cgatttcttc ggcggaggcc agggtgtgca cgtcctcggg      780
gttgcgatag gtgtccggag gggcacgtg caggaagccc tgaccgaggg gctcgtactt      840
gtacttgcgc tgggcctgac cggtcgcggc cagggcaccc atggagttgc cgtggtaggc      900
gcggtagcga gagatgaact gtagcggcc gtggtcaccc ttctgctggt ggtactggcg      960
ggcgatcttg aaggcggttt cgttggcctc cgagccggag ttggagaaga agatgacgta     1020
ctcgtcgtcc agccactcgt tcagcttctc ggccagcttg atggcggga cgtgcgactg     1080
cgtcagcggg aagtacggca tctcttccag ctgctcgaag gcagcgcgag ccagctcttt     1140
gcggccgtag ccgacgttga cgcaccacag gccggacatg ccgtccaggt agcggttgcc     1200
gtcgatgtcg gtgacccacg cgccttcggc cttggtgatg atcaggttgg tcggactcgg     1260
agcggcaccg cgcatggcgt gccacaggta cttctcgtcg gttttcttca ggctctgggt     1320
ctgctcggtg acctggacga tcatcagttc                                      1350

SEQ ID NO: 18          moltype = DNA   length = 747
FEATURE                Location/Qualifiers
source                 1..747
                       mol_type = genomic DNA
                       organism = Escherichia coli
SEQUENCE: 18
atgatcgttt tagtaactgg agcaacggca ggttttggtg aatgcattac tcgtcgtttt       60
attcaacaag gcataaaagt tatcgccact ggccgtcgcc aggagcggtt gcaggagtta      120
aaagacgaac tgggagataa tctgtatatc gcccaactgg acgttcgcaa ccgcgccgct      180
attgaagaga tgctggcatc gcttcctgcc gagtggtgca atattgatat cctggtaaat      240
aatgccggct tggcgttggg catggagcct gcgcataaag ccagcgttga agactgggaa      300
acgatgatta taccaacaa caaaggcctg tatatatga cgcgcgccgt cttaccgggt      360
atggttgaac gtaatcatgg tcatattatt aacattggct caacggcagg tagctggccg      420
tatgccggtg gtaacgttta cggtgcgacg aaagcgtttg ttcgtcagtt tagcctgaat      480
ctgcgtacgg atctgcatgg tacggcggtg cgcgtcaccg acatcgaacc gggtctggtg      540
ggtggcaccg agttttccaa tgtccgcttt aaaggcgatg acggtaaagc ggaaaaaacc      600
tatcaaaata ccgttgcatt gacgccagaa gatgtcagcg aagccgtctg gtgggtgtca      660
acgctgcctg ctcacgtcaa tatcaatacc ctggaaatga tgccggttac ccaaagctat      720
gccggactga atgtccaccg tcagtaa                                          747

SEQ ID NO: 19          moltype = AA   length = 248
FEATURE                Location/Qualifiers
source                 1..248
                       mol_type = protein
                       note = Enterobacteriaceae
                       organism = unidentified
SEQUENCE: 19
MIVLVTGATA GFGECITRRF IQQGHKVIAT GRRQERLQEL KDELGDNLYI AQLDVRNRAA       60
IEEMLASLPA EWCNIDILVN NAGLALGMEP AHKASVEDWE TMIDTNNKGL VYMTRAVLPG      120
MVERNHGHII NIGSTAGSWP YAGGNVYGAT KAFVRQFSLN LRTDLHGTAV RVTDIEPGLV      180
GGTEFSNVRF KGDDGKAEKT YQNTVALTPE DVSEAVWWVS TLPAHVNINT LEMMPVTQSY      240
AGLNVHRQ                                                              248

SEQ ID NO: 20          moltype = DNA   length = 741
FEATURE                Location/Qualifiers
misc_feature           1..741
                       note = codon optimized synthetic cDNA of E. coli HPDH
source                 1..741
                       mol_type = other DNA
                       organism = synthetic construct
SEQUENCE: 20
atcgtgctgg tcacgggcgc gaccgccggt ttcggcgagt gcatcacccg ccgcttcatc       60
cagcagggcc acaaggtgat cgctaccgga cgccgcaag agcgcctcca agagctgaag      120
gatgagctgg gcgacaacct gtacattgcc cagctgacg tgcgcaaccg cgctgccatc      180
gaagaaatgc tcgcctcgct gccgccgag tggtgcaaca tcgacatcct ggtcaacaac      240
gccggtctgg ccctcggcat ggaaccgcg cacaaggcca gcgtcgagga ctgggaaacc      300
atgatcgaca ccaacaacaa gggactcgtc tacatgaccc gcgctgtgct gcccggcatg      360
gtcgagcgca accacggcca tcatcaac atcggctcca ccgctggcag ctggccctac      420
gctggcggca acgtctatgg gcgcaccaag gcgttcgtcc cctgaacctg            480
cgcaccgacc tgcacggcac cgccgtccgc gtgaccgaca ttgagccggg tctggtcggc      540
ggcaccgagt tcagcaacgt ccgcttcaag ggcgacgacg gcaaggccga gaaacctac      600
cagaacaccg tcgctctgac ccctgaggat gtcagcgagg ccgtctggtg ggtcagcact      660
ctgccccgcgc acgtcaacat caacaccctc gagatgatgc ccgtcacgca gtcctacgcc      720
ggcctgaacg tccaccgcca a                                                741

SEQ ID NO: 21          moltype = DNA   length = 8478
FEATURE                Location/Qualifiers
misc_feature           1..8478
                       note = Synthetic nucleic acid
```

| source | 1..8478 |
| | mol_type = other DNA |
| | organism = synthetic construct |

SEQUENCE: 21

```
tgcagccgg gggatccact agttctagag cggccgccac cgcgtggag ctccagcttt    60
tgttcccttt agtgagggtt aattgcgcgc ttggcgtaat catggtcata gctgtttcct   120
gtgtgaaatt gttatccgct cacaattcca cacaacatac gagccggaag cataaagtgt   180
aaagcctggg gtgcctaatg agtgagctaa ctcacattaa ttgcgttgcg ctcactgccc   240
gctttccagt cgggaaacct gtcgtgccag ctgcattaat gaatcggcca acgcgcgggg   300
agaggcggtt tgcgtattgg gcgctcttcc gcttcctcgc tcactgactc gctgcgctcg   360
gtcgttcggc tgcggcgagc ggtatcagct cactcaaagg cggtaatacg gttatccaca   420
gaatcagggg ataacgcagg aaagaacatg tgagcaaaag gccagcaaaa ggccaggaac   480
cgtaaaaagg ccgcgttgct ggcgtttttc cataggctcc gcccccctga cgagcatcac   540
aaaaatcgac gctcaagtca gaggtggcga acccgacagg actataaaga taccaggcg   600
tttccccctg gaagctccct cgtgcgctct cctgttccga ccctgccgct taccggatac   660
ctgtccgcct ttctcccttc gggaagcgtg gcgctttctc atagctcacg ctgtaggtat   720
ctcagttcgg tgtaggtcgt tcgctccaag ctgggctgtg tgcacgaacc cccgttcag   780
cccgaccgct gcgccttatc cggtaactat cgtcttgagt ccaacccggt aagacacgac   840
ttatcgccac tggcagcagc cactggtaac aggattagca gagcgaggta tgtaggcggt   900
gctacagagt tcttgaagtg gtggcctaac tacggctaca ctagaaggac agtatttggt   960
atctgcgctc tgctgaagcc agttaccttc ggaaaaagag ttggtagctc ttgatccggc  1020
aaacaaacca ccgctggtag cggtggtttt tttgtttgca agcagcagat tacgcgcaga  1080
aaaaaaggat ctcaagaaga tcctttgatc ttttctacgg gtctgacgc tcagtggaac  1140
gaaaactcac gttaagggat tttggtcatg agattatcaa aaaggatctt cacctagatc  1200
cttttaaatt aaaaatgaag ttttaaatca atctaaagta tatatgagta aacttggtct  1260
gacagttacc aatgcttaat cagtgaggca cctatctcag cgatctgtct atttcgttca  1320
tccatagttg cctgactccc cgtcgtgtag ataactacga tacggagggg cttaccatct  1380
ggccccagtg ctgcaatgat accgcgagac ccacgctcac cggctccaga tttatcagca  1440
ataaaccagc cagccggaag ggccgagcgc agaagtggtc ctgcaacttt atccgcctcc  1500
atccagtcta ttaattgttg ccgggaagct agagtaagta gttcgccagt taatagtttg  1560
cgcaacgttg ttgccattgc tacaggcatc gtggtgtcac gctcgtcgtt tggtatggct  1620
tcattcagct ccggttccca acgatcaagg cgagttacat gatccccat gttgtgcaaa  1680
aaagcggtta gctccttcgg tcctccgatc gttgtcagaa gtaagttggc cgcagtgtta  1740
tcactcatgg ttatggcagc actgcataat tctcttactg tcatgccatc cgtaagatgc  1800
ttttctgtga ctggtgagta ctcaaccaag tcattctgag aatagtgtat gcggcgaccg  1860
agttgctctt gcccggcgtc aatacggat aataccgcgc cacatagcag aactttaaaa  1920
gtgctcatca ttggaaaacg ttcttcgggg cgaaaactct caaggatctt accgctgttg  1980
agatccagtt cgatgtaacc cactcgtgca cccaactgat cttcagcatc ttttactttc  2040
accagcgttt ctgggtgagc aaaaacagga aggcaaaatg ccgcaaaaaa ggggaataagg   2100
gcgacacgga aatgttgaat actcatactc ttcctttttc aatattattg aagcatttat   2160
cagggttatt gtctcatgag cggatacata tttgaatgta tttagaaaaa taaacaaata   2220
ggggttccgc gcacatttcc ccgaaaagtg ccacctgacg cgcctgtag cggcgcatta   2280
agcgcggcgg gtgtggtggt tacgcgcagc gtgaccgcta cacttgccag cgccctagcg   2340
cccgctcctt tcgctttctt cccttccttt ctcgccacgt tcgccggctt tccccgtcaa   2400
gctctaaatc gggggctccc tttagggttc cgatttagtg ctttacggca cctcgacccc   2460
aaaaaacttg attagggtga tggttcacgt agtgggccat cgccctgata cggttttt   2520
cgccctttga cgttggagtc cacgttcttt aatagtggac tcttgttcca aactggaaca   2580
acactcaacc ctatctcggt ctattctttt gatttataag gattttgcc gatttcggcc   2640
tattggttaa aaaatgagct gatttaacaa aatttaacg cgaattttaa caaaatatta   2700
acgcttacaa ttttccattcg ccattcaggc tgcgcaactg ttgggaaggg cgatcggtgc   2760
gggcctcttc gctattacgc cagctggcga aggggggatg tgctgcaagg cgattaagtt   2820
gggtaacgcc agggttttcc cagtcacgac gttgtaaaac gacggccagt gagcgcgcgt   2880
aatacgactc actatagggc gaattgggta ccgggccccc cctcgaggtc gacggtatcg   2940
atagtttaaa cgttgaccta gctgattctg gagtgaccca gagggtcatg acttgagcct   3000
aaaatccgcc gcctccacca tttgtagaaa aatgtgacga actcgtgagc tctgtacagt   3060
gaccggtgac tctttctggc atgcggagag acgacggac gcagagagaa gggctgagta   3120
ataagccact ggccagacag ctctggcggc tctgaggtgc agtggatgat tattaatccg   3180
ggaccggccg cccctccgcc ccgaagtgga aaggctggtg tgccctcgt tgaccaagaa   3240
tctattgcat catcggagaa tatggagctt catcgaatca ccggcagtaa gcgaaggaga   3300
atgtgaagcc aggggtgtat agccgtcggc gaaatagcat gccattaacc taggtacaga   3360
agtccaattg cttccgatct ggtaaaagat tcacgagata gtaccttctc cgaagtaggt   3420
agagcgagta cccggcgcgt aagctcccta attggcccat ccggcatctg tagggcgtcc   3480
aaatatcgtg cctctcctgc tttgcccggt gtatgaaacc ggaaaggccg ctcaggagct   3540
ggccagcggc gcagaccggg aacacaagct gcagtcgac ccatccggtg ctctgcactc   3600
gacctgctga ggtccctcag tccctggtag gcagctttgc cccgtctgtc cgcccggtag   3660
gtcggcgggg ttgacaaggt cgttgcgtca gtccaacatt tgttgccata ttttcctgct   3720
ctccccacca gctgctcttt tcttttctct ttcttttccc atcttcagta tattcatctt   3780
cccatccaag aacctttatt tcccctaagt aagtactttg ctacatccat actccatcct   3840
tcccatccct tattccttg aacctttcag ttcgagcttt cccacttcat cgcagcttga   3900
ctaacagcta ccccgcttga gcagacatca ccatgacgag agacgagcac gatgttactt   3960
cctcgcggac ctcagcgac gaagatgtga tctccttgga ggagcagcca acgcgcgacg   4020
accatgccaa tggagcgcta gaaaagcaga gcacggtcgc ctccgactg tcgaggttgg   4080
agagtcgcgc gcagtctgta attcgcgca tccgcagccg cgagcctggt caaacggcgc   4140
gctttacgca tccgctgtcg cataccaaaa cgtgcgtgta cgtgattgtg gattttgacg   4200
ggccggacga tccatatcgg cctatgaact ggactttcag gaaaaaggcc gtgacaactg   4260
tgttgtatgg cttgacaaca atgggcgcca cttgggcaag ttccatgtat gtctagcccc   4320
cctctctcct accatttgcg aattgcgact caggtatact aatgatgcgc agtttctcga   4380
caggcacgca gcaagtgagt aaacagtacc atgtcggcga ggaggttggc actctcggca   4440
ccactctact tctactcggc ttcggtaagt cgttccatca tgatgtcttc ggtgcatatg   4500
```

```
cggactgatc actcacatct catcttgcga tacaggtctg ggtcctctgg tctgggcccc    4560
attgtccgag gtatacggcc gcaaaccggc cgtcttagcg ccctacttta tcgccgcgat    4620
attctcgttc ggaaccgcaa ccgctaaaga tatccaaacc attatgatca cccgtttctt    4680
caccggattc ttcggctcag cccccgtcac caacaccggt ggtgtgcttg gcgatatctg    4740
gtccgccgaa gaacggggcg ccgctatcgt cggatacgcc atggctgtcg tgggcgggcc    4800
agttctgggc cccattgttg gtggcgccat cgtacaaagc tacctgcgat ggcgatggac    4860
agaatacgtg cgtaattcga atccccggc gaacacacgc caccccggt catcagatac     4920
taacttcgcc ccccgtacac agatcaccgg catcatgatg ttcttcttcc tgctcatgga    4980
cgtcgtgttc ctcgacgaaa gctacccgcc cgtcctcctc gtgtacaaag cacggcgcct    5040
gcgctacgac acgggcaact gggccctgca cgcgaagcac gaagaatggg acgtcaccttt   5100
caaggagctc ggcaacaagt acctcatccg ccccttcgcc ctcctcgcca cgcccatctg    5160
cttcctcgtc gccttgtacg cctccttcgt ctacggcatc ctctacctca gtctggcctc    5220
cttccccgtc gagtttcagg aagtgcgcgg cttttcccgt cccgaggcc cgcctccctc     5280
ccatgatgct cggctctgtc ctcttcgccg caggcctctt catcttccgc tggaccggcc    5340
gcccggatat ccactggatc ggccccatca tcggcgccgt ctccatgggc ttcggcttct    5400
tcacgatctt ccaggccgcc ctgaactatc tcatcgatac cttccagaag gtcgcggcca    5460
gcgctgtggc cgccaacacc ttcctccgca gcgttttcgc cgggtgcttc ccgctgttcg    5520
cgacgatcat gttccgcaga ctcggtgtcg actgggcctc gagtgtgttg gggttcgtcg    5580
ccgtcgcgtt gatcccgatc ccgtacctgt tctatatctt cggaaagcgg atcagagcga    5640
gagggaagtg gtcacgcgct tctgtttacg gctactgaag tagatgccga ccgcgggatc    5700
cacttaacgt tactgaaatc atcaaacagc ttgacgaatc tggatataag atcgttggtg    5760
tcgatgtcag ctccggagtt gagacaaatg gtgttcagga tctcgataag atacgttcat    5820
ttgtccaagc agcaaagagt gccttctagt gatttaatag ctccatgtca acaagaataa    5880
aacgcgtttt cgggtttacc tcttccagat acagctcatc tgcaatgcat taatgcattg    5940
actgcaacct agtaacgcct ttcaggctcc ggcgaagaga agaatagctt agcagagcta    6000
ttttcatttt cgggagacga gatcaagcag atcaacgctg gctcaagagac ctacgagact   6060
gaggaatccg ctcttggctc cacgcgacta tatatttgtc tctaattgta ctttgacatg    6120
ctcctcttct ttactctgat agcttgacta tgaaaattcc gtcaccagct cctgggttcg    6180
caaagataat tgcatgtttc ttccttgaac tctcaagcct acaggacaca cattcatcgt    6240
aggtataaac ctcgaaatca tttcctacta agatggtaa caatagtaac catgcatgt     6300
tgcctagtga atgctccgta cacccaata cgccggccga aacttttta caactctcct     6360
atgagtcgtt tacccagaat gcacaggtac acttgtttag aggtaatcct tctttctaga    6420
agtcctcgtg tactgtgtaa gcgcccactc cacatctcca ctcgatctga cagacgggca    6480
attgattacg ggatcccatt ggtaacgaaa tgtaaaagct aggagatcgt ccgccgatgt    6540
caggatgatt tcacttgttt cttgtccggc tcaccggtca aagctaaaga ggagcaaaag    6600
gaacggatag aatcgggtgc cgctgatcta tacggtatag tgcccttatc acgttgactc    6660
aacccatgct atttaactca accctcctt ctgaacccca ccatcttctt cctttttcctc    6720
tcatcccaca caattctcta tctcagattt gaattccaaa agtcctcgga cgaaactgaa    6780
caagtcttcc tccccttcgat aaacctttgg tgattggaat aactgaccat cttctatagt    6840
tcccaaaacca accgacaatg taaatacact cctcgattag ccctctagag ggcatacgat    6900
ggaagtcatg gaatactttt ggctggactc tcacaatgat caaggtatct taggtaacgt    6960
cttttggcgtg ggccggtgtt cgttcccagt catcgatgca ttcacatgcc ctccctaagc    7020
tgggccctag actctaggat cctagtctag aaggacatgg catcgatgg ctgggttcgt     7080
tctgagatta tacggctaaa acttgatctg gataatacca gcgaaaaggg tcatgccttc    7140
tctcgttctt cctgttgatg gaatggctaa cagatgatag tcattgcaac ttgaaacatg    7200
tctcctccag ctgccatcta cgaacccact gtggccgcta ccggcctcaa gggtaaggtc    7260
gtggttctg agaccgtccc cgttgaggga gcttctcaga ccaagctgtt ggaccatttc    7320
ggtggcaagt gggacgagtt caagttcgcc cctatccgcg aaagccaggt ctctcgtgcc    7380
atgaccagac gttactttga ggacctggac aagtacgctg aaagtgacgt tgtcattgtt    7440
ggtgctggtt cctgcggtct gagcactgcg tacgtcttgg ccaaggctcg tccggacctg    7500
aagattgcta tcgtcgaggc cagcgtctct cctggtcagt agtccatgat ggattgcctt    7560
gcactcagct ttccggaact aacgtgcaat aggtggcggt gcctggttgg gtggccaact    7620
cttttctgct atggtcatgc gccgtcccgc ggaagtcttc ctgaacgagc tgggtgttcc    7680
ttacgaagag gacgcaaacc ccaactacgt tgtcgtcaag cacgcctccc tgtttacctc    7740
gacactcatg tcgaaggttc tctccttccc caatgtcaac ctcttcaatg ctaccgctgt    7800
tgaggacttg atcacccgtc cgaccgagaa cggcaacccc cagattgctg gtgttgtcgt    7860
caactggacg ctggtcaccc ttcaccacga tgatcactcc tgcatggacc ccaacactat    7920
caacgctcct gtcatcatca gtaccactgg tcacgatggg ccattcggcg ccttctgtgc    7980
gaagcgcttg gtgtccatgg gcagcgtcga caagctaggt ggcatgcgtg gtctcgacat    8040
gaactcggcc gaggatgcca tcgtcaagaa cacccgcgag gttactaagg gcttgataat    8100
cggcggtatg gagctgtctg aaattgatgg ctttaaccgc atgggcccta ccttcggtgc    8160
catggttctc agtggtgtca aggctgccga ggaggcattg aaggtgttcg acgagcgtca    8220
gcgcgagtgt gctgagtaaa tgactcacta cccgaatggg ttcagtgcat gaaccggatt    8280
tgtcttacgg tctttgacga taggggaatg atgattatgt gatagttctg agatttgaat    8340
gaactcgtta gctcgtaatc cacatgcata tgtaaatggc tgtgtcccgt atgtaacggt    8400
ggggcattct agaataatta tgtgtaacaa gaaagacagt ataatacaaa caaagatgca    8460
agagcggctc gtttaaac                                                   8478
```

```
SEQ ID NO: 22           moltype = DNA   length = 20
FEATURE                 Location/Qualifiers
misc_feature            1..20
                        note = Synthetic nucleic acid
source                  1..20
                        mol_type = other DNA
                        organism = synthetic construct
SEQUENCE: 22
ctccagtaac agaaccgacc                                                 20

SEQ ID NO: 23           moltype = DNA   length = 20
```

```
FEATURE                 Location/Qualifiers
misc_feature            1..20
                        note = Synthetic nucleic acid
source                  1..20
                        mol_type = other DNA
                        organism = synthetic construct
SEQUENCE: 23
gaacttcact gccgcattgg                                               20

SEQ ID NO: 24           moltype = DNA  length = 21
FEATURE                 Location/Qualifiers
misc_feature            1..21
                        note = Synthetic nucleic acid
source                  1..21
                        mol_type = other DNA
                        organism = synthetic construct
SEQUENCE: 24
ggacactcca agaggataag g                                             21

SEQ ID NO: 25           moltype = DNA  length = 20
FEATURE                 Location/Qualifiers
misc_feature            1..20
                        note = Synthetic nucleic acid
source                  1..20
                        mol_type = other DNA
                        organism = synthetic construct
SEQUENCE: 25
gctcatcaca ttgtttgccg                                               20

SEQ ID NO: 26           moltype = DNA  length = 50
FEATURE                 Location/Qualifiers
misc_feature            1..50
                        note = Synthetic nucleic acid
source                  1..50
                        mol_type = other DNA
                        organism = synthetic construct
SEQUENCE: 26
tgacctccac tagctccagc ggtcaattta agaggacgat cttcgctgcg              50

SEQ ID NO: 27           moltype = DNA  length = 50
FEATURE                 Location/Qualifiers
misc_feature            1..50
                        note = Synthetic nucleic acid
source                  1..50
                        mol_type = other DNA
                        organism = synthetic construct
SEQUENCE: 27
aatagagtag atgccgaccg tcagcctgga caggctcacc gacattagcc              50

SEQ ID NO: 28           moltype = DNA  length = 50
FEATURE                 Location/Qualifiers
misc_feature            1..50
                        note = Synthetic nucleic acid
source                  1..50
                        mol_type = other DNA
                        organism = synthetic construct
SEQUENCE: 28
cgcagcgaag atcgtcctct taaattgacc gctggagcta gtggaggtca              50

SEQ ID NO: 29           moltype = DNA  length = 50
FEATURE                 Location/Qualifiers
misc_feature            1..50
                        note = Synthetic nucleic acid
source                  1..50
                        mol_type = other DNA
                        organism = synthetic construct
SEQUENCE: 29
ggctaatgtc ggtgagcctg tccaggctga cggtcggcat ctactctatt              50

SEQ ID NO: 30           moltype = DNA  length = 813
FEATURE                 Location/Qualifiers
source                  1..813
                        mol_type = genomic DNA
                        organism = Aspergillus niger
SEQUENCE: 30
ctactatgaa agaccgcgat gggccgatag tagtagttac ttccattaca tcatctcatc   60
cgcccggttc ctcgcctccg cggcagtcta cgggtaggat cgtagcaaaa acccggggga  120
tagcccgtcg tcccgagct ggagttccgt ataacctagg tagaaggtat caattgaacc   180
cgaacaactg gcaaaacatt ctcgagatcg taggagtgag tacccggcgt gatggagggg  240
```

```
gagcacgctc attggtccgt acggcagctg ccgaggggga gcaggagatc caaatatcgt   300
gagtctcctg ctttgcccgg tgtatgaaac cggaaaggac tgctgggaa  ctggggagcg   360
gcgcaagccg ggaatcccag ctgacaattg acccatcctc atgccgtggc agagcttgag   420
gtagcttttg ccccgtctgt ctcccggtg  tgcgcattcg actgggcgcg gcatctgtgc   480
ctcctccagg agcggaggac ccagtagtaa gtaggcctga cctggtcgtt ggtcagtcc    540
agaggttccc tccccaccc  tttttctact tccctcccc  cgccgctcaa cttttcttc    600
cctttactt  tctctctctc ttcctcttca tccatcctct cttcatcact tccctcttcc   660
cttcatccaa ttcatcttcc aagtgagtct tcctccccat ctgtccctcc atctttccca   720
tcatcatctc ccttcccagc tcctcccctc ctctcgtctc ctcacgaagc ttgactaacc   780
attacccgc  cacatagaca catctaaaca atg                                813

SEQ ID NO: 31            moltype = DNA  length = 1040
FEATURE                  Location/Qualifiers
source                   1..1040
                         mol_type = genomic DNA
                         organism = Aspergillus niger
SEQUENCE: 31
tgatgggtg  gatgacgatg acttcatgtg attttgttat ttagaatatt ttatatttcc    60
tttcttctt  ctcaccaccg atcccttaa  cactcttgct tcatttgctt cagatttctc   120
ggtttcttct tttttcttct cccagttat  ccactatatc tttgctagac cggcctgcgc   180
cctggcatgc atcataaaat catgtccgtt ggtcatcatc tgttttgtat atccgtcata   240
taaagtattc ttttattccc tccccctcg  gtcgtctttc gctgtcccgc ttcctacctc   300
cggtttatag agcatggttc atctcttccg tacatttccg ttggtactag catttatgtc   360
ttcagctagt atagaagctg ccgcagttgt tcgcttacta cctgcctaag tccttaactt   420
tttaaagtgt ttaacctata cgtagtgtta acgagtact  gggaggtggt gaggtagaaa   480
atgttctgca cgggcagtgg gtatttggta gtgtgtaagg ggttattta  tcaggctgtc   540
gctaaagact tctatgggag cagtatggga tcgcggctca tagaagtaca caaaatctaa   600
gagtcgtttg ataattaatt gattcccggc agggtcttct tggattgag  agaactggtt   660
actttgattt gagatattgt aaagcttaag gctcttaaca cgtacgagcg aaacagcagg   720
ggggaaatcg ggaaaagggg cgtggggtga ataaaaagt  tgaaataaga cactgtatct   780
tgctgggggt gaataaagag agaataaaag agaggtaaat tccactcagc cccttttctt   840
cgctctccaa acatcaaact ccgccggccg acccacagga tcccgaacaa gtggaagata   900
tgtgccggtc cagaccctc  gcacagctaa agcagacct  tcataagcgt ttccgggtag   960
tattcgcaca cctgaactgg cacgtcgggg acacaactgt ttttgataca caagaacaca  1020
caccacccat ctaggactca                                              1040

SEQ ID NO: 32            moltype = DNA  length = 704
FEATURE                  Location/Qualifiers
source                   1..704
                         mol_type = genomic DNA
                         organism = Aspergillus niger
SEQUENCE: 32
catgttgatg gactggaggg ggatgagtta tggatcagtg aaactgggag aaaacaaaga    60
tggcaaaggg agaacatggc ccagatatag gaaaaacgg  aggaggcaaa aatgtaagcg   120
ctccggactt gctgtttcgg tgtgcactag cagcagcggg ggggaaggtg gtgagtgttc   180
accgaggacc caaaaagaat gagcggatgg cggatgagtg acggagaagg gaaggacggg   240
ggggaatta  gaggtggaga ggtccgatcc atcaaataga ccaggctcgg cacagccaag   300
tttcccaaat gatcaactaa tcaatggac  ttggtgctaa atccggagat gccagatcat   360
tgatagacag acaggatgga gtgatggcat atagacagga ggatggatgg atggatagat   420
ggaggggtca agcacaacat ggtgggatga tggcggggtc atgactagca gctaagagga   480
agaagaggag gatgaaatgg acagagaag  atgggagggg tgataaaatg agtatatggg   540
acaagtcata cttacaggac cttgaagatg gtggttgtac tatctaagaa aggctttttt   600
tgagagtact cttaacacaa gaggaggagg aggaggggg  aagtagtaga taaataataa   660
acacgaccac agacttgcta caggctactt cttgtaagct cgag                    704

SEQ ID NO: 33            moltype = DNA  length = 885
FEATURE                  Location/Qualifiers
source                   1..885
                         mol_type = genomic DNA
                         organism = Aspergillus nidulans
SEQUENCE: 33
tctgtacagt gaccggtgac tctttctggc atgcggagag acggacggac gcagagagaa    60
gggctgagta ataagccact ggccagacag ctctggcggc tctgaggtgc agtggatgat   120
tattaatccg ggaccggccg cccctccgcc ccgaagtgga aaggctggtg tgccccctcgt  180
tgaccaagaa tctattgcat catcggaaa  tatggagctt catcgaatca ccggcagtaa   240
gcgaaggaga atgtgaagcc agggtgtat  agccgtcggc gaaatagcat gccattaacc   300
taggtacaga agtccaattg cttccgatct ggtaaaagat tcacgagata gtaccttctc   360
cgaagtaggt agagcgagta cccggcgcgt aagctcccta attgcccat  ccggcatctg   420
tagggcgtcc aaatatcgtg cctctcctgc tttgcccgt  gtatgaaacc ggaaaggccg   480
ctcaggagct ggccagcggc gcagaccggg aacacaagct ggcagtcgac ccatccggtg   540
ctctgcactc gacctgctga ggtccctcag tccctggtag gcagctttgc cccgtctgtc   600
cgcccggtgt gtcggcgggg ttgacaaggt cgttgcgtca gtccaacatt tgttgccata   660
ttttcctgct ctccccacca gctgctcttt tcttttctct ttcttttccc atcttcagta   720
tattcatctt cccatccaag aacctttatt tcccctaagt aagtactttg ctacatccat   780
actccatcct tcccatccct tattcctttg aacctttcag ttcgagcttt cccacttcat   840
cgcagcttga ctaacagcta cccgcttga  gcagacatca ccatg                   885

SEQ ID NO: 34            moltype = DNA  length = 45
FEATURE                  Location/Qualifiers
```

```
misc_feature              1..45
                          note = Synthetic nucleic acid
source                    1..45
                          mol_type = other DNA
                          organism = synthetic construct
SEQUENCE: 34
aggtcgacgg tatcgatagt ttaaacgtga aagagattga ggatc              45

SEQ ID NO: 35             moltype = DNA   length = 29
FEATURE                   Location/Qualifiers
misc_feature              1..29
                          note = Synthetic nucleic acid
source                    1..29
                          mol_type = other DNA
                          organism = synthetic construct
SEQUENCE: 35
gtctgtcaga ccaatagata ccaatgagg                                29

SEQ ID NO: 36             moltype = DNA   length = 29
FEATURE                   Location/Qualifiers
misc_feature              1..29
                          note = Synthetic nucleic acid
source                    1..29
                          mol_type = other DNA
                          organism = synthetic construct
SEQUENCE: 36
tatctattgg tctgacagac gggcaattg                                29

SEQ ID NO: 37             moltype = DNA   length = 30
FEATURE                   Location/Qualifiers
misc_feature              1..30
                          note = Synthetic nucleic acid
source                    1..30
                          mol_type = other DNA
                          organism = synthetic construct
SEQUENCE: 37
cattgcagag gagccgctct tgcatctttg                               30

SEQ ID NO: 38             moltype = DNA   length = 30
FEATURE                   Location/Qualifiers
misc_feature              1..30
                          note = Synthetic nucleic acid
source                    1..30
                          mol_type = other DNA
                          organism = synthetic construct
SEQUENCE: 38
agagcggctc ctctgcaatg gatggccttc                               30

SEQ ID NO: 39             moltype = DNA   length = 43
FEATURE                   Location/Qualifiers
misc_feature              1..43
                          note = Synthetic nucleic acid
source                    1..43
                          mol_type = other DNA
                          organism = synthetic construct
SEQUENCE: 39
gatccccggg gctgcagttt aaacgtggcg aggtgaacat ctc                43

SEQ ID NO: 40             moltype = DNA   length = 45
FEATURE                   Location/Qualifiers
misc_feature              1..45
                          note = Synthetic nucleic acid
source                    1..45
                          mol_type = other DNA
                          organism = synthetic construct
SEQUENCE: 40
aggtcgacgg tatcgatagt ttaaaccagt ccaacagtg gagtg               45

SEQ ID NO: 41             moltype = DNA   length = 29
FEATURE                   Location/Qualifiers
misc_feature              1..29
                          note = Synthetic nucleic acid
source                    1..29
                          mol_type = other DNA
                          organism = synthetic construct
SEQUENCE: 41
gtctgtcaga ggatacccat cgtgggatg                                29

SEQ ID NO: 42             moltype = DNA   length = 29
```

```
FEATURE                 Location/Qualifiers
misc_feature            1..29
                        note = Synthetic nucleic acid
source                  1..29
                        mol_type = other DNA
                        organism = synthetic construct
SEQUENCE: 42
atgggtatcc tctgacagac gggcaattg                                            29

SEQ ID NO: 43           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 43
catcccgcac gagccgctct tgcatctttg                                           30

SEQ ID NO: 44           moltype = DNA  length = 28
FEATURE                 Location/Qualifiers
misc_feature            1..28
                        note = Synthetic nucleic acid
source                  1..28
                        mol_type = other DNA
                        organism = synthetic construct
SEQUENCE: 44
agagcggctc gtgcgggatg gggtgtga                                             28

SEQ ID NO: 45           moltype = DNA  length = 44
FEATURE                 Location/Qualifiers
misc_feature            1..44
                        note = Synthetic nucleic acid
source                  1..44
                        mol_type = other DNA
                        organism = synthetic construct
SEQUENCE: 45
ggatccccg gctgcagtt taaacactgt cccagaggtc cgtc                             44

SEQ ID NO: 46           moltype = DNA  length = 44
FEATURE                 Location/Qualifiers
misc_feature            1..44
                        note = Synthetic nucleic acid
source                  1..44
                        mol_type = other DNA
                        organism = synthetic construct
SEQUENCE: 46
aggtcgacgg tatcgatagt ttaaacggta atctcggaat tcgc                           44

SEQ ID NO: 47           moltype = DNA  length = 29
FEATURE                 Location/Qualifiers
misc_feature            1..29
                        note = Synthetic nucleic acid
source                  1..29
                        mol_type = other DNA
                        organism = synthetic construct
SEQUENCE: 47
gtctgtcaga aggaggacat tgtgagtag                                            29

SEQ ID NO: 48           moltype = DNA  length = 29
FEATURE                 Location/Qualifiers
misc_feature            1..29
                        note = Synthetic nucleic acid
source                  1..29
                        mol_type = other DNA
                        organism = synthetic construct
SEQUENCE: 48
atgtcctcct tctgacagac gggcaattg                                            29

SEQ ID NO: 49           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 49
tgaaccagac gagccgctct tgcatctttg                                           30
```

| SEQ ID NO: 50 | moltype = DNA  length = 31 |
| --- | --- |
| FEATURE | Location/Qualifiers |
| misc_feature | 1..31 |
| | note = Synthetic nucleic acid |
| source | 1..31 |
| | mol_type = other DNA |
| | organism = synthetic construct |

SEQUENCE: 50
agagcggctc gtctggttca agtgaagctt g           31

| SEQ ID NO: 51 | moltype = DNA  length = 45 |
| --- | --- |
| FEATURE | Location/Qualifiers |
| misc_feature | 1..45 |
| | note = Synthetic nucleic acid |
| source | 1..45 |
| | mol_type = other DNA |
| | organism = synthetic construct |

SEQUENCE: 51
ggatcccccg ggctgcagtt taaacctcct cgagagctgg agaac           45

| SEQ ID NO: 52 | moltype = DNA  length = 44 |
| --- | --- |
| FEATURE | Location/Qualifiers |
| misc_feature | 1..44 |
| | note = Synthetic nucleic acid |
| source | 1..44 |
| | mol_type = other DNA |
| | organism = synthetic construct |

SEQUENCE: 52
aggtcgacgg tatcgatagt ttaaacgcac gacacaacac agtc           44

| SEQ ID NO: 53 | moltype = DNA  length = 30 |
| --- | --- |
| FEATURE | Location/Qualifiers |
| misc_feature | 1..30 |
| | note = Synthetic nucleic acid |
| source | 1..30 |
| | mol_type = other DNA |
| | organism = synthetic construct |

SEQUENCE: 53
gtctgtcaga tcgacggcat gttcaagttg           30

| SEQ ID NO: 54 | moltype = DNA  length = 29 |
| --- | --- |
| FEATURE | Location/Qualifiers |
| misc_feature | 1..29 |
| | note = Synthetic nucleic acid |
| source | 1..29 |
| | mol_type = other DNA |
| | organism = synthetic construct |

SEQUENCE: 54
atgccgtcga tctgacagac gggcaattg           29

| SEQ ID NO: 55 | moltype = DNA  length = 30 |
| --- | --- |
| FEATURE | Location/Qualifiers |
| misc_feature | 1..30 |
| | note = Synthetic nucleic acid |
| source | 1..30 |
| | mol_type = other DNA |
| | organism = synthetic construct |

SEQUENCE: 55
aacgcaccag gagccgctct tgcatctttg           30

| SEQ ID NO: 56 | moltype = DNA  length = 28 |
| --- | --- |
| FEATURE | Location/Qualifiers |
| misc_feature | 1..28 |
| | note = Synthetic nucleic acid |
| source | 1..28 |
| | mol_type = other DNA |
| | organism = synthetic construct |

SEQUENCE: 56
agagcggctc ctggtgcgtt gatggagc           28

| SEQ ID NO: 57 | moltype = DNA  length = 45 |
| --- | --- |
| FEATURE | Location/Qualifiers |
| misc_feature | 1..45 |
| | note = Synthetic nucleic acid |
| source | 1..45 |
| | mol_type = other DNA |
| | organism = synthetic construct |

SEQUENCE: 57
gatccccgg gctgcagttt aaacctcttg actatcgcgt atcac           45

| SEQ ID NO: 58 | moltype = DNA length = 45 |
| --- | --- |
| FEATURE | Location/Qualifiers |
| misc_feature | 1..45 |
| | note = Synthetic nucleic acid |
| source | 1..45 |
| | mol_type = other DNA |
| | organism = synthetic construct |

SEQUENCE: 58
aggtcgacgg tatcgatagt ttaaacagac gcattgctgt tctac                45

| SEQ ID NO: 59 | moltype = DNA length = 28 |
| --- | --- |
| FEATURE | Location/Qualifiers |
| misc_feature | 1..28 |
| | note = Synthetic nucleic acid |
| source | 1..28 |
| | mol_type = other DNA |
| | organism = synthetic construct |

SEQUENCE: 59
gtctgtcaga tcgtgctcgt ctctcgtc                                   28

| SEQ ID NO: 60 | moltype = DNA length = 29 |
| --- | --- |
| FEATURE | Location/Qualifiers |
| misc_feature | 1..29 |
| | note = Synthetic nucleic acid |
| source | 1..29 |
| | mol_type = other DNA |
| | organism = synthetic construct |

SEQUENCE: 60
acgagcacga tctgacagac gggcaattg                                  29

| SEQ ID NO: 61 | moltype = DNA length = 30 |
| --- | --- |
| FEATURE | Location/Qualifiers |
| misc_feature | 1..30 |
| | note = Synthetic nucleic acid |
| source | 1..30 |
| | mol_type = other DNA |
| | organism = synthetic construct |

SEQUENCE: 61
caacatgctc gagccgctct tgcatctttg                                 30

| SEQ ID NO: 62 | moltype = DNA length = 28 |
| --- | --- |
| FEATURE | Location/Qualifiers |
| misc_feature | 1..28 |
| | note = Synthetic nucleic acid |
| source | 1..28 |
| | mol_type = other DNA |
| | organism = synthetic construct |

SEQUENCE: 62
agagcggctc gagcatgttg aatgttgc                                   28

| SEQ ID NO: 63 | moltype = DNA length = 44 |
| --- | --- |
| FEATURE | Location/Qualifiers |
| misc_feature | 1..44 |
| | note = Synthetic nucleic acid |
| source | 1..44 |
| | mol_type = other DNA |
| | organism = synthetic construct |

SEQUENCE: 63
ggatcccccg ggctgcagtt taaacaagtc ctcgacatgg tctg                 44

| SEQ ID NO: 64 | moltype = DNA length = 45 |
| --- | --- |
| FEATURE | Location/Qualifiers |
| misc_feature | 1..45 |
| | note = Synthetic nucleic acid |
| source | 1..45 |
| | mol_type = other DNA |
| | organism = synthetic construct |

SEQUENCE: 64
ggtcgacggt atcgatagtt taaaccctgg tgatcttgta agcag                45

| SEQ ID NO: 65 | moltype = DNA length = 30 |
| --- | --- |
| FEATURE | Location/Qualifiers |
| misc_feature | 1..30 |
| | note = Synthetic nucleic acid |
| source | 1..30 |
| | mol_type = other DNA |
| | organism = synthetic construct |

SEQUENCE: 65

```
gtctgtcaga gggagatcat ggtctggatg                                             30

SEQ ID NO: 66           moltype = DNA   length = 29
FEATURE                 Location/Qualifiers
misc_feature            1..29
                        note = Synthetic nucleic acid
source                  1..29
                        mol_type = other DNA
                        organism = synthetic construct
SEQUENCE: 66
atgatctccc tctgacagac gggcaattg                                              29

SEQ ID NO: 67           moltype = DNA   length = 30
FEATURE                 Location/Qualifiers
misc_feature            1..30
                        note = Synthetic nucleic acid
source                  1..30
                        mol_type = other DNA
                        organism = synthetic construct
SEQUENCE: 67
tccccgatgg gagccgctct tgcatctttg                                             30

SEQ ID NO: 68           moltype = DNA   length = 29
FEATURE                 Location/Qualifiers
misc_feature            1..29
                        note = Synthetic nucleic acid
source                  1..29
                        mol_type = other DNA
                        organism = synthetic construct
SEQUENCE: 68
agagcggctc ccatcgggga tggcctaag                                              29

SEQ ID NO: 69           moltype = DNA   length = 43
FEATURE                 Location/Qualifiers
misc_feature            1..43
                        note = Synthetic nucleic acid
source                  1..43
                        mol_type = other DNA
                        organism = synthetic construct
SEQUENCE: 69
ggatccccg ggctgcagtt taaactccac acgactgtcg aag                               43

SEQ ID NO: 70           moltype = DNA   length = 44
FEATURE                 Location/Qualifiers
misc_feature            1..44
                        note = Synthetic nucleic acid
source                  1..44
                        mol_type = other DNA
                        organism = synthetic construct
SEQUENCE: 70
aggtcgacgg tatcgatagt ttaaacgcga gagactagtc gttg                             44

SEQ ID NO: 71           moltype = DNA   length = 20
FEATURE                 Location/Qualifiers
misc_feature            1..20
                        note = Synthetic nucleic acid
source                  1..20
                        mol_type = other DNA
                        organism = synthetic construct
SEQUENCE: 71
gtgatgccat tacacggtag                                                        20

SEQ ID NO: 72           moltype = DNA   length = 39
FEATURE                 Location/Qualifiers
misc_feature            1..39
                        note = Synthetic nucleic acid
source                  1..39
                        mol_type = other DNA
                        organism = synthetic construct
SEQUENCE: 72
ctaccgtgta atggcatcac tctgacagac gggcaattg                                   39

SEQ ID NO: 73           moltype = DNA   length = 30
FEATURE                 Location/Qualifiers
misc_feature            1..30
                        note = Synthetic nucleic acid
source                  1..30
                        mol_type = other DNA
                        organism = synthetic construct
```

```
SEQUENCE: 73
cggcagtcct gagccgctct tgcatctttg                              30

SEQ ID NO: 74           moltype = DNA  length = 29
FEATURE                 Location/Qualifiers
misc_feature            1..29
                        note = Synthetic nucleic acid
source                  1..29
                        mol_type = other DNA
                        organism = synthetic construct
SEQUENCE: 74
agagcggctc aggactgccg gagttgttg                               29

SEQ ID NO: 75           moltype = DNA  length = 43
FEATURE                 Location/Qualifiers
misc_feature            1..43
                        note = Synthetic nucleic acid
source                  1..43
                        mol_type = other DNA
                        organism = synthetic construct
SEQUENCE: 75
ggatccccg ggctgcagtt taaacctcat ccaacgcaac ggc                43

SEQ ID NO: 76           moltype = DNA  length = 44
FEATURE                 Location/Qualifiers
misc_feature            1..44
                        note = Synthetic nucleic acid
source                  1..44
                        mol_type = other DNA
                        organism = synthetic construct
SEQUENCE: 76
aggtcgacgg tatcgatagt ttaaacccgg gtattagatg tgcg              44

SEQ ID NO: 77           moltype = DNA  length = 28
FEATURE                 Location/Qualifiers
misc_feature            1..28
                        note = Synthetic nucleic acid
source                  1..28
                        mol_type = other DNA
                        organism = synthetic construct
SEQUENCE: 77
gtctgtcaga ctgtggacat tgtgcggg                                28

SEQ ID NO: 78           moltype = DNA  length = 29
FEATURE                 Location/Qualifiers
misc_feature            1..29
                        note = Synthetic nucleic acid
source                  1..29
                        mol_type = other DNA
                        organism = synthetic construct
SEQUENCE: 78
atgtccacag tctgacagac gggcaattg                               29

SEQ ID NO: 79           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 79
ggacatggaa gagccgctct tgcatctttg                              30

SEQ ID NO: 80           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 80
agagcggctc ttccatgtcc atctatcatg                              30

SEQ ID NO: 81           moltype = DNA  length = 43
FEATURE                 Location/Qualifiers
misc_feature            1..43
                        note = Synthetic nucleic acid
source                  1..43
                        mol_type = other DNA
```

```
                                organism = synthetic construct
SEQUENCE: 81
ggatcccccg ggctgcagtt taaacggttc atgacaatgg atg                      43

SEQ ID NO: 82           moltype = DNA  length = 41
FEATURE                 Location/Qualifiers
misc_feature            1..41
                        note = Synthetic nucleic acid
source                  1..41
                        mol_type = other DNA
                        organism = synthetic construct
SEQUENCE: 82
cgaggtcgac ggtatcgata gtttaaacgt tgacctagct g                        41

SEQ ID NO: 83           moltype = DNA  length = 28
FEATURE                 Location/Qualifiers
misc_feature            1..28
                        note = Synthetic nucleic acid
source                  1..28
                        mol_type = other DNA
                        organism = synthetic construct
SEQUENCE: 83
ctctcgtcat ggtgatgtct gctcaagc                                       28

SEQ ID NO: 84           moltype = DNA  length = 28
FEATURE                 Location/Qualifiers
misc_feature            1..28
                        note = Synthetic nucleic acid
source                  1..28
                        mol_type = other DNA
                        organism = synthetic construct
SEQUENCE: 84
agacatcacc atgacgagag acgagcac                                       28

SEQ ID NO: 85           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 85
ggcatctact tcagtagccg taaacagaag                                     30

SEQ ID NO: 86           moltype = DNA  length = 28
FEATURE                 Location/Qualifiers
misc_feature            1..28
                        note = Synthetic nucleic acid
source                  1..28
                        mol_type = other DNA
                        organism = synthetic construct
SEQUENCE: 86
cggctactga agtagatgcc gaccgcgg                                       28

SEQ ID NO: 87           moltype = DNA  length = 30
FEATURE                 Location/Qualifiers
misc_feature            1..30
                        note = Synthetic nucleic acid
source                  1..30
                        mol_type = other DNA
                        organism = synthetic construct
SEQUENCE: 87
gtctgtcaga tcgagtggag atgtggagtg                                     30

SEQ ID NO: 88           moltype = DNA  length = 29
FEATURE                 Location/Qualifiers
misc_feature            1..29
                        note = Synthetic nucleic acid
source                  1..29
                        mol_type = other DNA
                        organism = synthetic construct
SEQUENCE: 88
ctccactcga tctgacagac gggcaattg                                      29

SEQ ID NO: 89           moltype = DNA  length = 44
FEATURE                 Location/Qualifiers
misc_feature            1..44
                        note = Synthetic nucleic acid
source                  1..44
```

```
                    mol_type = other DNA
                    organism = synthetic construct
SEQUENCE: 89
agtggatccc ccgggctgca gtttaaacga gccgctcttg catc                    44
```